US012702425B2

(12) United States Patent
Smith et al.

(10) Patent No.: US 12,702,425 B2
(45) Date of Patent: Aug. 11, 2026

(54) DEVICES AND SYSTEMS TO MITIGATE TRAUMATIC BRAIN AND OTHER INJURIES CAUSED BY CONCUSSIVE OR BLAST FORCES

(71) Applicants: TBI Innovations, LLC, Richmond, IN (US); Thornhill Research, Inc., Toronto (CA)

(72) Inventors: David W. Smith, Richmond, IN (US); Kevin John Vititoe, Westerville, OH (US); Jamison Joseph Float, Galloway, OH (US); Chad Michael Leeder, New Albany, OH (US); Joseph A. Fisher, Thornhill (CA); John Stites, Sallisaw, OK (US)

(73) Assignees: TBI INNOVATIONS, LLC, West Chester, OH (US); THORNHILL RESEARCH, INC., Toronto (CA)

( * ) Notice: Subject to any disclaimer, the term of this patent is extended or adjusted under 35 U.S.C. 154(b) by 362 days.

(21) Appl. No.: 15/151,948

(22) Filed: May 11, 2016

(65) Prior Publication Data

US 2016/0317160 A1 Nov. 3, 2016

Related U.S. Application Data

(60) Division of application No. 14/317,282, filed on Jun. 27, 2014, now Pat. No. 10,842,502, which is a (Continued)

(51) Int. Cl.

*A61B 17/132* (2006.01)
*A61B 17/135* (2006.01)
(Continued)

(52) U.S. Cl.

CPC ...... *A61B 17/1325* (2013.01); *A61B 17/1327* (2013.01); *A61B 17/135* (2013.01);
(Continued)

(58) Field of Classification Search

CPC ......... Y10S 2/916; A41D 27/16; A41D 27/18; A41D 13/0512; A41D 13/0587;
(Continued)

(56) References Cited

U.S. PATENT DOCUMENTS

| | | |
|---|---|---|
| 428,926 A | 5/1890 | Martin |
| 519,894 A | 5/1894 | Schutz |

(Continued)

FOREIGN PATENT DOCUMENTS

| | | |
|---|---|---|
| CA | 2823184 A1 | 4/2012 |
| CA | 2823184 | 9/2015 |

(Continued)

OTHER PUBLICATIONS

AU, 2015279773 Examination Report No. 2, Mar. 9, 2018.

(Continued)

*Primary Examiner* — Kathleen S Holwerda

(74) *Attorney, Agent, or Firm* — Ruggiero McAllister & McMahon LLC

(57) ABSTRACT

A system for reducing the damaging effects of radiant energy, blast, or concussive events includes applying pressure to at least one jugular vein to reduce the egress of blood from the cranial cavity during or before the incidence of the imparting event. Reducing blood outflow from the cranial cavity increases intracranial volume and/or pressure of the cerebrospinal fluid to reduce the risk of traumatic brain injury and injuries to the spinal column. Reducing blood outflow further increases the intracranial pressure and volume, and thereby increases the pressure and volume of the cochlear fluid, the vitreous humor and the cerebrospinal (Continued)

fluid to thereby reduce the risk of injury to the inner ear, internal structure of the eye and of the spinal column. In addition, increasing intracranial pressure and volume reduces the likelihood of brain injury and any associated loss of olfactory function

13 Claims, 26 Drawing Sheets

Related U.S. Application Data continuation-in-part of application No. 13/842,273, filed on Mar. 15, 2013, now Pat. No. 9,173,660, which is a continuation-in-part of application No. 13/489,536, filed on Jun. 6, 2012, now Pat. No. 10,004,515, which is a continuation of application No. PCT/US2011/055783, filed on Oct. 11, 2011, and a continuation-in-part of application No. 12/931,415, filed on Feb. 1, 2011, now Pat. No. 9,168,045, which is a continuation-in-part of application No. 12/807, 677, filed on Sep. 10, 2010, now Pat. No. 8,985,120.

(60) Provisional application No. 61/518,117, filed on Apr. 29, 2011, provisional application No. 61/260,313, filed on Nov. 11, 2009, provisional application No. 61/241,625, filed on Sep. 11, 2009.

(51) Int. Cl.
*A61H 39/04* (2006.01)
*F41H 1/00* (2006.01)
*A61B 17/00* (2006.01)

(52) U.S. Cl.
CPC ............... *A61H 39/04* (2013.01); *F41H 1/00* (2013.01); *A61B 2017/00017* (2013.01); *A61B 2017/00221* (2013.01); *A61B 2017/00778* (2013.01)

(58) Field of Classification Search
CPC ................ A41D 13/00; A41D 13/0002; A41D 13/0012; A41D 1/02; A41D 1/04; A41D 13/0051; A41D 13/018; A41D 13/05; A41D 13/0518; A41D 13/0015; A41D 13/055; A61B 17/1325; A61B 17/1327; A61B 17/135; A61F 5/012; A61F 5/055; A63B 71/1291; F41H 1/02; A61H 39/04
USPC ............................................ 606/201–204.15
See application file for complete search history.

(56) References Cited

U.S. PATENT DOCUMENTS 1,123,873 A 1/1915 Heflin
1,280,742 A 10/1918 Hurd
1,473,041 A 11/1923 Henderson
1,481,354 A 1/1924 Dingfeld
1,592,496 A 7/1926 Madden
1,691,856 A 11/1928 Robbins
2,091,276 A 8/1937 Gilbert
2,271,927 A 2/1942 Saighman
2,284,205 A 5/1942 Hansen
2,320,183 A 5/1943 Martin
2,385,638 A 9/1945 Norwood
2,676,586 A 4/1954 Coackwell
2,715,994 A 8/1955 Steinacker
3,008,464 A 11/1961 Atkins
3,078,844 A 2/1963 Scholz
3,171,409 A 3/1965 Cetrone
3,477,425 A 11/1969 Grassi
3,490,448 A 1/1970 Grubb
3,497,872 A 3/1970 Mitchell
3,500,472 A * 3/1970 Castellani ................ A42B 3/12
2/462
3,595,225 A 7/1971 Beeman
3,628,536 A 12/1971 Glense
3,657,739 A 4/1972 Holmes, Sr.
3,765,412 A 10/1973 Ommaya et al.
3,850,164 A 11/1974 Hare
3,901,230 A 8/1975 Henkin
3,945,042 A 3/1976 Lobo
4,121,582 A 10/1978 Masso Remiro
4,159,020 A 6/1979 von Soiron et al.
4,188,946 A 2/1980 Watson et al.
4,243,028 A 1/1981 Puyana
4,272,011 A 6/1981 Nagatomo et al.
4,308,861 A 1/1982 Kelly
4,336,807 A * 6/1982 Benckhuijsen .......... A41D 1/04
607/108
4,343,303 A 8/1982 Williams
4,377,159 A 3/1983 Hansen
4,479,495 A 10/1984 Isaacson
4,576,150 A 3/1986 Auracher
4,628,926 A 12/1986 Duncan et al.
4,646,728 A 3/1987 Takeda
4,716,898 A 1/1988 Chauve et al.
4,817,595 A 4/1989 Maass
4,991,576 A 2/1991 Henkin
4,997,438 A 3/1991 Nipper
5,078,728 A 1/1992 Giarratano
5,152,302 A 10/1992 Fareed
5,255,675 A 10/1993 Kolobow
5,295,949 A 3/1994 Hathaway
5,295,996 A 3/1994 Blair
5,302,806 A * 4/1994 Simmons ........... A41D 13/0051
219/211
5,312,350 A 5/1994 Jacobs
5,320,093 A 6/1994 Raemer
5,338,290 A 8/1994 Aboud
5,375,261 A * 12/1994 Lipke ................ A41D 13/0051
2/103
5,381,558 A 1/1995 Lo
5,398,675 A 3/1995 Henkin et al.
5,403,266 A 4/1995 Bragg et al.
5,497,767 A 3/1996 Olsson et al.
5,501,697 A 3/1996 Fisher
5,507,280 A 4/1996 Henkin et al.
5,507,721 A 4/1996 Shippert
D369,660 S 5/1996 Myoga
5,582,585 A 12/1996 Nash-Morgan
5,584,853 A 12/1996 McEwen
5,601,598 A 2/1997 Fisher
5,643,315 A 7/1997 Daneshvar
5,690,610 A * 11/1997 Ito ...................... A61F 13/0203
602/56
5,695,520 A 12/1997 Bruckner et al.
5,709,647 A 1/1998 Ferber
5,752,927 A 5/1998 Rogachevsky
5,776,123 A 7/1998 Goerg et al.
5,792,176 A 8/1998 Chang
5,806,093 A 9/1998 Summers
5,817,218 A 10/1998 Hayashi et al.
5,848,981 A 12/1998 Herbranson
5,940,888 A 8/1999 Sher
5,957,128 A 9/1999 Hecker et al.
5,978,965 A 11/1999 Summers
6,007,503 A 12/1999 Berger et al.
D419,267 S 1/2000 Hartunian
6,038,701 A * 3/2000 Regan ................ A41D 13/0512
2/115
6,158,434 A 12/2000 Lugtighcid et al.
6,165,105 A 12/2000 Boutellier
6,217,601 B1 4/2001 Chao
6,227,196 B1 5/2001 Jaffe et al.
6,238,413 B1 5/2001 Wexler
6,245,024 B1 6/2001 Montagnino et al.
6,274,786 B1 8/2001 Heller
6,344,021 B1 2/2002 Juster et al.
6,354,292 B1 3/2002 Fisher
6,423,020 B1 7/2002 Koledin

(56) References Cited

U.S. PATENT DOCUMENTS 6,554,787 B1 4/2003 Griffin et al.
D475,139 S 5/2003 Myoga
6,558,407 B1 5/2003 Ivanko et al.
6,612,308 B2 9/2003 Fisher et al.
6,622,725 B1 9/2003 Fisher et al.
6,623,835 B2 9/2003 Chang
6,655,382 B1 12/2003 Kolobow
6,659,689 B1 12/2003 Courtney et al.
6,663,653 B2 12/2003 Akerfeldt
6,700,031 B1 3/2004 Hahn
6,711,750 B1 3/2004 Yoo
6,763,525 B1 7/2004 Spector
6,766,570 B1 7/2004 Klemm et al.
6,799,470 B2 10/2004 Harada
6,799,570 B2 10/2004 Fisher et al.
6,802,841 B2 10/2004 Narimatsu
6,854,134 B2 2/2005 Cleveland
7,069,598 B1 7/2006 Welch
7,100,251 B2 9/2006 Howell
7,100,606 B2 9/2006 Fisher et al.
7,141,031 B2 11/2006 Garth et al.
D539,425 S 3/2007 Harrison
7,207,953 B1 4/2007 Goicaj
D555,836 S 11/2007 Foust et al.
7,452,339 B2 11/2008 Mattison
7,618,386 B2 11/2009 Nordt, III et al.
7,653,948 B2 2/2010 Schwenner
7,981,135 B2 7/2011 Thorpe
D653,018 S 1/2012 Webbe et al.
8,109,963 B1 2/2012 Korrol
8,376,975 B1 2/2013 Harris, Jr.
8,381,362 B2 2/2013 Hammerslag et al.
8,900,169 B2 12/2014 Smith et al.
8,955,165 B1 * 2/2015 Romero .................. A41D 3/02 2/101
8,985,120 B2 3/2015 Smith
9,173,660 B2 11/2015 Smith et al.
D763,518 S 8/2016 Fletcher et al.
9,913,501 B1 3/2018 Flug
10,905,180 B1 2/2021 Minaev et al.
2002/0004948 A1 1/2002 Son
2003/0056275 A1 * 3/2003 Regan .................... A63B 71/12 2/78.1
2003/0130690 A1 7/2003 Porrata et al.
2004/0127937 A1 7/2004 Newton
2004/0128744 A1 7/2004 Cleveland
2004/0243044 A1 12/2004 Penegor et al.
2004/0267178 A1 12/2004 Benckendorff
2005/0049631 A1 * 3/2005 Carter-Smith ....... A44C 9/0053 606/204
2005/0262618 A1 12/2005 Musal
2006/0048293 A1 3/2006 Lewis et al.
2006/0095072 A1 5/2006 TenBrink
2006/0122550 A1 6/2006 Weaver
2006/0142675 A1 6/2006 Sargent
2006/0200195 A1 9/2006 Yang
2007/0033696 A1 2/2007 Sellier
2007/0060949 A1 3/2007 Curry et al.
2007/0123796 A1 5/2007 Lenhardt et al.
2007/0260167 A1 11/2007 Heart
2008/0021498 A1 1/2008 Di Lustro
2008/0071202 A1 3/2008 Nardi et al.
2008/0132820 A1 6/2008 Buckman et al.
2008/0154140 A1 6/2008 Chang et al.
2008/0200853 A1 8/2008 Tielve
2008/0319473 A1 12/2008 Rosenbaum
2009/0076421 A1 3/2009 Grant, Jr.
2009/0099496 A1 4/2009 Heegaard et al.
2009/0105625 A1 4/2009 Kohncr et al.
2009/0131973 A1 5/2009 Zacharias
2009/0143706 A1 6/2009 Acosta
2009/0173340 A1 7/2009 Lee
2009/0192423 A1 7/2009 Halmos
2009/0209925 A1 8/2009 Marinello et al.
2009/0234261 A1 9/2009 Singh
2009/0299242 A1 12/2009 Hasegawa
2010/0000548 A1 1/2010 Haworth et al.
2010/0042138 A1 2/2010 Duelo Riu
2010/0071169 A1 3/2010 Williams et al.
2010/0088808 A1 4/2010 Rietdyk et al.
2010/0094332 A1 4/2010 Willshaw
2010/0122404 A1 5/2010 Bowlus et al.
2010/0137768 A1 6/2010 Thorgilsdottir et al.
2010/0139671 A1 6/2010 Tull et al.
2010/0152771 A1 6/2010 Di Lustro
2010/0204628 A1 8/2010 Ghajar
2010/0294284 A1 11/2010 Hohenhorst et al.
2010/0318114 A1 12/2010 Pranevicius et al.
2011/0010829 A1 1/2011 Norman
2011/0028934 A1 2/2011 Buckman et al.
2011/0040265 A1 2/2011 Lu et al.
2011/0065637 A1 3/2011 Smith
2011/0093003 A1 4/2011 Lee
2011/0107492 A1 * 5/2011 Hinchey ................ A41D 13/11 2/9
2011/0257571 A1 10/2011 Fritsch et al.
2011/0270299 A1 11/2011 Rose et al.
2011/0295174 A1 12/2011 Richards
2011/0295311 A1 12/2011 Adelman
2012/0078157 A1 3/2012 Ravikumar
2012/0197290 A1 * 8/2012 Smith ................ A41D 13/0512 606/201
2012/0246974 A1 10/2012 Hammerslag et al.
2012/0291189 A1 11/2012 Chambers et al.
2013/0041303 A1 2/2013 Hopman et al.
2013/0055492 A1 3/2013 Husain
2013/0085426 A1 4/2013 Brodsky
2013/0239310 A1 9/2013 Flug
2013/0274638 A1 10/2013 Jennings
2013/0304111 A1 11/2013 Zhadkevich
2013/0333708 A1 12/2013 Hassan
2014/0031781 A1 1/2014 Razon-Domingo
2014/0031787 A1 1/2014 Burnes et al.
2014/0142616 A1 5/2014 Smith
2014/0236221 A1 8/2014 Zhadkevich
2014/0257155 A1 9/2014 Altinok et al.
2014/0276278 A1 9/2014 Smith et al.
2014/0277101 A1 9/2014 Smith et al.
2014/0343599 A1 11/2014 Smith et al.
2015/0305751 A1 10/2015 Hoff et al.
2015/0313607 A1 11/2015 Zhadkevich
2016/0044981 A1 2/2016 Frank et al.
2016/0045203 A1 2/2016 Pollock
2016/0169630 A1 6/2016 Augustine et al.
2016/0213381 A1 7/2016 Zhadkevich
2016/0317160 A1 11/2016 Smith et al.
2017/0215769 A1 8/2017 Lu et al.
2017/0215795 A1 8/2017 Ahmad et al.
2018/0325194 A1 11/2018 Elvira et al.
2020/0266207 A1 8/2020 Liu
2020/0330323 A1 10/2020 Jolly et al.
2021/0182856 A1 6/2021 Kuchenski et al.
2021/0223580 A1 7/2021 Xu
2021/0254179 A1 8/2021 Ku et al.

FOREIGN PATENT DOCUMENTS

CA 3005557 5/2017
CN 201189186 2/2009
CN 201341912 Y 11/2009
CN 101690658 7/2011
CN 102326890 1/2012
CN 102326890 A 1/2012
CN 202618320 U 12/2012
CN 103384444 A 11/2013
CN 103385555 11/2013
CN 103385555 A 11/2013
DE 3409335 9/1985
EP 0067622 A1 12/1982
EP 2637927 A1 9/2013
EP 2 662 034 A1 11/2013
EP 2777411 9/2014
FR 719730 2/1932
FR 2041596 A5 1/1971

(56) References Cited

FOREIGN PATENT DOCUMENTS

| | | |
|---|---|---|
| GB | 291600 | 6/1928 |
| GB | 1282097 | 7/1972 |
| GB | 2024644 | 1/1980 |
| JP | 42002568 | 10/1963 |
| JP | 84499310 | 9/1975 |
| JP | S559202 | 1/1980 |
| JP | S6266102 | 3/1987 |
| JP | H0207814 | 1/1990 |
| JP | H11247001 | 9/1999 |
| JP | 2003135472 | 5/2003 |
| JP | 2003-235816 | 8/2003 |
| JP | 2004337393 | 12/2004 |
| JP | 2004036067 | 5/2005 |
| JP | 2005-273094 | 10/2005 |
| JP | 2005292006 | 10/2005 |
| JP | 3171026 U | 10/2011 |
| WO | 1996020783 | 7/1996 |
| WO | 1998046144 | 10/1998 |
| WO | WO 98/46144 A1 | 10/1998 |
| WO | 2003020061 | 3/2003 |
| WO | 2008150966 A1 | 12/2008 |
| WO | 2009/152649 A1 | 12/2009 |
| WO | 2010056280 | 5/2010 |
| WO | WO 2011/048518 A1 | 4/2011 |
| WO | WO 2012/054262 A1 | 4/2012 |
| WO | WO 2012/156335 A1 | 11/2012 |
| WO | WO 2012/168449 A1 | 12/2012 |
| WO | 2013/055409 A1 | 4/2013 |
| WO | 2013055409 | 4/2013 |
| WO | 2014143853 | 9/2014 |
| WO | 2015061663 | 4/2015 |
| WO | 2017172964 | 10/2017 |
| WO | 2020005409 | 1/2020 |
| WO | 2020048518 | 3/2020 |
| WO | 2020051545 | 3/2020 |
| WO | 2020054262 | 3/2020 |
| WO | 2020055409 | 3/2020 |
| WO | 2020056280 | 3/2020 |
| WO | 2020061663 | 4/2020 |
| WO | 2020074350 | 4/2020 |
| WO | 2020143853 | 7/2020 |
| WO | 2020150966 | 7/2020 |
| WO | 2020152649 | 7/2020 |
| WO | 2020156335 | 8/2020 |
| WO | 2020168449 | 8/2020 |
| WO | 2020172964 | 9/2020 |
| WO | 2020200672 | 10/2020 |

OTHER PUBLICATIONS

EP, 15811930.5 Extended Search Report, Feb. 20, 2018.

EP, 12840429.0 Communication pursuant to Article 94(3), Mar. 24, 2017.

AU, Patent Examination Report No. 2, Patent Application No. 2011318427, Apr. 21, 2016.

CA, Canadian Office Action, Application No. 2,812,131, Dec. 6, 2013.

CA, Canadian Office Action, Application No. 2,823,184, Dec. 11, 2013.

CA, Canadian Office Action, Application No. 2,823,184, Aug. 13, 2014.

CA, Canadian Office Action, Application No. 2,823,184, Oct. 29, 2014.

EP, Extended European Search Report, EP Application No. 13166318.9, Sep. 3, 2013.

EP, Extended European Search Report, EP Application No. 11834865.5, Sep. 17, 2014.

US, Non-final Office Action U.S. Appl. No. 12/931,415, filed Mar. 13, 2013.

US, Non-final Office Action U.S. Appl. No. 13/489,536, filed Apr. 24, 2013.

WO, International Search Report, Patent Application No. PCT/US2011/055783, Jan. 19, 2012.

WO, International Search Report, Patent Application No. PCT/US14/28004, Sep. 11, 2014.

WO, International Search Report, Patent Application No. PCT/US15/37753, Dec. 14, 2015.

Batson, Oscar V., "Anatomical Problems Concerned in the Study of Cerebral Blood Flow," Fed. Proc., 3:139-144 (1944).

Cardoso, Antonio Valadão, et al., "Microplate Reader Analysis of Triatomine Saliva Effect on Eyrthrocyte Aggregation," Materials Research, 10(1):31-36 (2007).

Ferguson, J., et al., "Cervical collars: a potential risk to the head-injured patient," Injury, 24(7):454-456 (1993) printed in Great Britain.

Finnie, J.W., et al., "Animal Models, Traumatic Brain Injury." Vet Pathol. 39:679-689 (2002).

Gilland, Olaf, et al., "A Cinemyelographic Study of Cerebrospinal Fluid Dynamics," American journal of Roentgenology, 106(2):369-375 (Jun. 1969).

Gregg, Donald E., et al., "Experimental Approaches to the Study of the Cerebral Circulation," Fed. Proc., 3:144-151 (1944).

Kitano, Masami, et al., "The Elasticity of the Cranial Blood Pool," Journal of Nuclear Medicine, 5:613-625 (1964).

May, Philip R.A., et al., "Woodpecker Drilling Behavior, An Endorsement of the Rotational Theory of impact Brain Injury," Arch. Neurol., 36:370-373 (1979).

Moyer, J., et al., "Effect of increased jugular pressure on cerebral hemodynamic," Journal of Applied Physiology, 7(3):245-247 (1954).

Templer, Donald I., et al., "Preventable Brain Damage, Brain Vulnerability and Brain Health," Part I: Impact Damage; ECT and Permanent Brain Damage, Springer Publishing Company, New York pp. 95-107 (1992).

Torres, Fernando, et al., "Changes in the electroencephalogram and in systemic blood pressure associated with carotid compression," Neurology, 20:1077-1083 (Nov. 1970).

Tyrrell, D.A.J., et al., "Observations on the C.S.F. Pressure During Compression of the Jugular Veins," Postgrad. Med. J., 27(210): 394-395 (Aug. 1951).

Vannucci, R.C., et al., "Carbon dioxide protects the perinatal brain from hypoxic-ischemic damage: an experimental study in the immature rat," Pediatrics, Abstract from 95(6):868-874 (Jun. 1995).

Eurasian second office action dated Apr. 15, 2021 from corresponding Eurasian Patent Application No. 202090647, 4 pages.

Walusinski et al. , How Yawning Switches the Default-Mode Network to the Attentional Network by Activating the Cerebrospinal Fluid Flow, Clinical Anatomy 27:201-209 (2014).

Leonard et al., Comparison of central venous and external jugular venous pressures during repair of proximal femoral fracture, British Journal of Anaesthesia (2008), vol. 101, No. 2, pp. 166-170.

May, Woodpecker Drilling Behavior, an Endorsement of the Rotational Theory of Impact Brain Injury, Arch Neurology, Jun. 1979, 370-373, vol. 36.

Hartlage, Brain Injury from Motor Vehicle Accidents, Preventable Damage: Brain Vulnerability and Brain Health. New York: Springer Publishing Company1992.

Transportation-related incidents are the leading cause of brain injury; Brain Injury Association of America; wwwbiausa.org; Apr. 2001.

Extended European Search Report dated Nov. 3, 2021 from corresponding European Patent Application No. 20207673.3, 12 pages.

Japanese Notice of Reasons for Refusal dated Sep. 1, 2021 from corresponding Japanese Patent Application No. 2019-154417, 4 pages.

Partial European Search Report dated Jul. 30, 2021 from corresponding European Patent Application No. 20207673.3, 14 pages.

JP, 2019-154417 Office Action, Sep. 30, 2020.

Batson "Anatomical Problems Concerned in the Study of Cerebral Blood Flow, Federation Proceedings" Federation of American Societies for Experimental Biology, 1944, 139-144, vols. 3-4.

Baum "St. X, Moeller aid in concussion prevention study" Cincinnati.com, Jan. 8, 2016.

Cardosoa et al "Microplate Reader Analysis of Triatomine Saliva Effect on Erythrocyte Aggregation" Materials Research, vol. 10, No. 1, 31-362007.

(56) References Cited

OTHER PUBLICATIONS

Ferguson “Cervical Collars: A Potential Risk to the Head-Injured Patient” International Journal of Care for the Injured, (1993), vol. 24, No. 7, pp. 454-456.

Finnie “Animal Models Traumatic Brain Injury” Veterinary Pathology, 2002, 679-689, vol. 39.

Gilland “A Cinemyelographic Study of Cerebrofspinal Fluid Dynamics” Amer J of Roent, 106 (2): 369 (1969).

Gregg “Experimental Approaches to the Study of the Cerebral Circulation” Fed. Proc., 1944, 3:144.

Kitano “The Elasticity of the Cranial Blood Pool” Journal of Nuclear Medicine 5:613-625, 1964.

Moyer “Effect of Increased Jugular Pressure on Cerebral Hemodynamic” Journal of Applied Physiology, Nov. 1954, 245-247, vol. 7, No. 3.

Vannucci, “Carbon dioxide protects the perinatal brain from hypoxic-ischemic damage: an experimental study in the Immature rat” Department of Pediatrics (Pediatric Neurology), Jun. 1995, 868-874, vol. 95, No. 6.

Omalu “Concussions and NFL: How the name CTE came about” CNN, Dec. 22, 2015.

Orcutt“New Collar Promises to Keep Athletes’ Brains from “Sloshing” During Impact” MIT Technology Review, Feb. 3, 2016.

Performance Sports Group Ltd., “Performance Sports Group and Leading Medical Experts Unveil First-of-its-Kind Technology to Address Mild Traumatic Brain Injury” PR Newswire, Nov. 17, 2015.

Taylor“New wearable neck collar could help reduce brain injuries in athletes”Sports Illustrated, Jun. 15, 2016.

Torres, “Changes in the electroencephalogram and in systemic blood pressure associated with carotid compression”, Neurology 1970; 20:1077-1083.

Vasavada et al “Head and Neck Anthropometry, Vertebral Geometry and Neck Strength in Height-Matched Men and Women” J. Biomechanics, 41 (2008) 114-121.

Boeing “Airplane Vibration” Boeing Aero Magazine, No. 16, Oct. 2001.

Lic et al “Potential Connections of Cockpit Floor Seat on Passive Vibration Reduction at a Piston Propelled Airplane” Technical Gazette 21, 3(2014) 471-478.

Terhardt “Dominant Spectral Region” The Wayback Machine, Feb. 20, 2000, https://web.archive.org/web/20120426090422/http://www.mmk.e-technik.tu-muench . . . .

* cited by examiner 65
76
66
67
66
67
75
62
60
72
70

72
70

70
67
65
62
60
75
76
20, 40
66

67 67 67 67
66
66
72 72 72 72

67 67 67 67
66 66 66 66

66 66 66 66
72 72 72 72

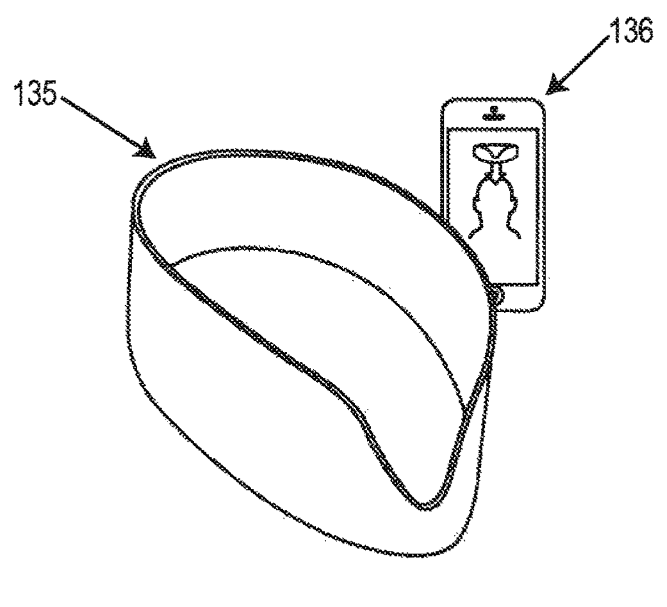
FIG. 27
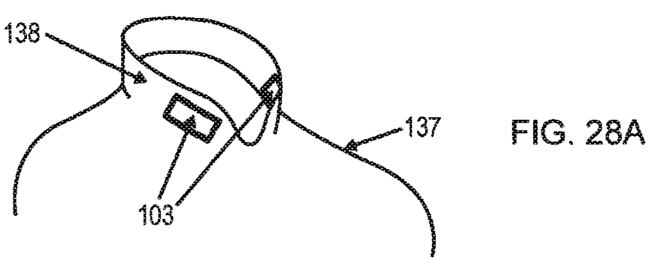
FIG. 28A
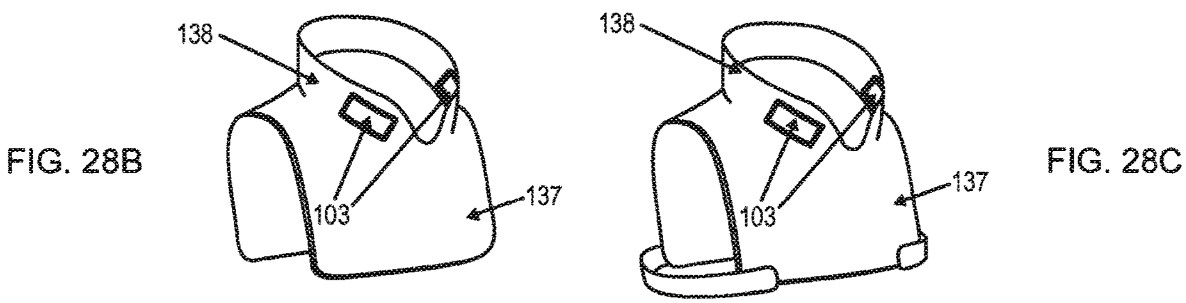
FIG. 28B
FIG. 28C

DEVICES AND SYSTEMS TO MITIGATE TRAUMATIC BRAIN AND OTHER INJURIES CAUSED BY CONCUSSIVE OR BLAST FORCES

CROSS-REFERENCE TO RELATED APPLICATIONS

This patent is a divisional of U.S. Ser. No. 14/317,282, filed on Jun. 27, 2014, which is a continuation-in-part of U.S. Ser. No. 13/842,273, filed on Mar. 15, 2013, now, U.S. Pat. No. 9,173,660, which is a continuation in part of U.S. Ser. No. 13/489,536, filed Jun. 6, 2012, which is a continuation-in-part of U.S. Ser. No. 12/931,415, filed Feb. 1, 2011, now U.S. Pat. No. 9,168,045, which is a continuation-in-part of U.S. Ser. No. 12/807,677, filed Sep. 10, 2010, now U.S. Pat. No. 8,985,120, which claims the benefit of U.S. Provisional Application 61/260,313, filed Nov. 11, 2009, and 61/241,625, filed Sep. 11, 2009. U.S. Ser. No. 13/489,536 is also a continuation-in-part of PCT/US2011/055783, filed Oct. 11, 2011, which claims the benefit of U.S. Provisional Application 61/518,117, filed Apr. 29, 2011. Each of the above-referenced patent applications is incorporated herein by reference.

TECHNICAL FIELD

The present disclosure is generally related to systems for reducing the effects of exposure to concussive events.

BACKGROUND OF THE INVENTION

Traumatic brain injury (TBI) continues to be one of the most common causes of death and morbidity in persons under age 45, even in western societies. A reported 1.7 million people suffer from TBI annually in the United States alone, resulting in an estimated per annum total cost of over $60 billion. Historically, prevention of skull and brain injury has focused on the use of helmets as external cranial protection. This approach is fundamentally flawed as helmets have provided benefit for only major penetrating brain injuries and skull fractures. These occur in a very small fraction of head injuries in civilian sphere. Military statistics have shown that even on the battlefield, less than 0.5% of TBI is from a penetrating object. However, both military personnel and athletes are subjected to high velocity acceleration-deceleration mechanisms that are not mitigated by helmets and lead to concussive injury to the brain. In large part, the human brain's relative freedom of movement within the cranial cavity predisposes to both linear and rotational force vectors, with resultant energy absorption resulting in cellular disruption and dysfunction, sometimes with delayed cell death.

The skull and spinal canal contain only nervous tissue, connective tissue and fat cells and their interstitium, blood, and cerebrospinal fluid (CSF). The non-fluid contents do not completely fill the rigid container delimited by the skull and bony spinal canal, leaving a 'reserve volume' that is occupied by the fluid components. The change in volume inside a container for a given change in pressure is termed 'compliance'. Increases in volume of the contents of the skull and bony spinal canal, within the range of reserve volume, occur at low container pressures (due to the high compliance of the system). Acceleration or deceleration of the skull can result in a differential acceleration or deceleration between the skull and its contents when the brain and fluids collide with the inside of the skull. TBI may occur because of compression, stretching, or tearing of tissue and blood vessels as a result of the brain impacting the skull. Considering the semi-solid properties of the mammalian brain, this effect is referred to as "SLOSH".

While helmets are effective in preventing the infrequent penetration or fracture of the skull, they have little ability to limit SLOSH effects. Mitigating SLOSH by increasing the pressure of the fluid contents of the brain can significantly reduce the propensity for damage to the brain tissue or its blood vessels by reducing the compressibility of the brain. The reduction in compressibility results in reduced absorption of kinetic, acoustic, thermal, and vibrational energy by the brain.

The same concussive events that produce TBI can also have damaging effects to the inner ear, spinal cord and structures of the eye. Sensory neural hearing loss is noted to occur at a rate of 85% in TBI. Concurrent injuries to the auditory system as a result of acute blast trauma and resultant traumatic brain injury accounted for one-quarter of all injuries among marines during Operation Iraqi Freedom through 2004—the most common single injury type. Auditory dysfunction has become the most prevalent individual military service-connected disability, with compensation totaling more than $1 billion annually.

Although one might expect blast waves to cause tympanic membrane rupture and ossicular disruption (thus resulting in conductive hearing loss), available audiology reports showed that pure sensory neural loss was the most prevalent type of hearing loss in patients. An observational study performed from 1999-2006 found that 58 percent of active-duty soldiers who complained of hearing loss were diagnosed with pure sensorineural loss. Data from this study revealed that 38 percent of the patients with blast related TBI also reported sensory neural tinnitus (ringing in the ears).

The sites for sensory neural hearing loss are the inner ear structures referred to as the cochlea and vestibular apparatus (semicircular canals). Both of these structures are fluid filled and therefore susceptible to SLOSH induced energy absorption. The tympanic and vestibular canals of the cochlea are also fluid filled and transmit pressure and fluid waves to the delicate hair cells of the organ of corti. The auditory hair cells react directly to the vibrations in the liquid in which they are immersed rather than to transverse vibrations in the cochlear duct. The cochlea and its associated hair cells are particularly susceptible to SLOSH energy absorption.

Approximately 30 ml (21%) of a total CSF volume of 140 ml resides within the spinal axis, and about one-third of the compliance of the CSF system has been attributed to the spinal compartment. As in the brain, increasing the pressure of the CSF within the spinal compartment reduces the susceptibility of the spinal compartment to concussive injuries by increasing the elasticity of the contents of the spinal column, thereby reducing the amount of energy absorbed by the contents of the spinal column when subjected to a concussive force.

Of 207 severe eye injuries in a report of military casualties in Operation Iraq Freedom OIF, 82 percent were caused by blast and blast fragmentation. Eye injuries accounted for 13 percent (19/149) of all battlefield injuries seen at a combat support hospital during Operations Desert Shield and Desert Storm. Hyphema (blood within the anterior chamber) and traumatic cataract were the most common findings in closed globe injuries, the majority (67%) of eyes sustained orbital injury. Of the service members experiencing combat ocular trauma (COT) in Operation Enduring Freedom, 66 percent also had TBI. Simply stated, roughly two-thirds of the combat related eye injuries were closed blast wave energy absorptions resulting in rupture.

Traumatic brain injury, or the concussive or blast-related events leading to TBI, has also been found to be a leading cause of anosmia (loss or impairment of olfactory function, i.e., sense of smell). Certain studies have reported that a large proportion of patients with post-traumatic anosmia exhibit abnormalities in the olfactory bulbs and in the inferior frontal lobes, suggesting in the latter case that reducing TBI can reduce the risk of anosmia. While loss or impairment of olfactory function can be more than a nuisance to humans, the same injury to Breecher dogs (e.g., bomb sniffers) can be catastrophic. Breecher dogs are inherently exposed to the risk of concussive events and their primary purpose is to help soldiers avoid such an event. Preventing or reducing the likelihood of TBI and associated loss of smell can be critical to the Breecher dog's mission.

Standard prophylactic measures designed to protect the brain against injury in the case of head trauma have hitherto included only various helmets. Helmets are primarily designed to protect the skull from penetrating injuries and fractures, but less so from pathological movements of the brain, exemplified by the classic cerebral concussion. Moreover, helmets have no meaningful effect on blast-related injuries to the ear, spinal column and eyes.

SUMMARY OF THE INVENTION

Intracranial injuries due to exposure to external concussive forces remains a devastating condition for which traditionally extra-cranial protection has been utilized in the form of helmets. Although headgear is effective in preventing the most devastating intracranial injuries, penetrating injuries, and skull fractures, it is limited in its ability to prevent concussions or damage to the structures within the cranium. In accordance with one disclosed method, the internal jugular vein (IJV) is mildly compressed to increase cerebral blood volume and decrease the intracranial compliance. This results in increased intercranial volume and resultant pressure and thus reduction of the differential acceleration between the skull and its contents when subjected to a concussive force. Reduction in the differential acceleration between the skull and its contents means a reduction in propensity for compression, stretching, or tearing of the brain or vascular tissues within the skull, leading to less energy absorption, and thus less traumatic axonal and glial injury. Mild restriction of flow of the IJV also leads to increased cochlear pressure to reduce risk of damage to the inner ear, increased pressure in the cerebrospinal fluid to reduce the risk of injury to the spinal column, and increased intraocular pressure to protect the internal structure of the eye from concussive events.

In an attempt to mitigate intracranial slosh it is recognized that the single intracranial compartment that is most amenable to rapid, reversible change in volume and pressure is the blood space. The simplest and most rapid means of increasing the volume blood compartment is to inhibit its outflow by mechanically restricting one or more of the draining veins in the neck.

One aspect of the disclosure, therefore, encompasses methods for reducing the likelihood of injury to a subject exposed to external concussive force, comprising: contacting one or more protuberances to the neck of the subject, wherein each protuberance is located above one or more neck veins of the subject; and applying an external pressure to the protuberances sufficient to restrict blood flow egressing from the head of the subject through the one or more neck veins. In some embodiment, the injury comprises one or more selected from the group consisting of traumatic brain injury, concussive injury to the spinal column, concussive injury to the inner ear, and concussive injury to the ocular or olfactory structures.

In some embodiments, the one or more veins in the neck of the subject comprises one or more of an interior or exterior jugular vein. In some related embodiments, restriction of the blood flow egressing from the head of the subject results in an increase in fluid volume and pressure in the intracranial cavity of the subject. The cranial volume is not fixed as the eyeballs and the tympanic membranes can slightly bulge outward (as in the jugular tympanic reflex), further the foramen or opening of the cranial vault are all able to accommodate a greater volume. In some embodiments, the external pressure applied to the one or more veins in the neck is equivalent to a fluid pressure of 5-25 mm Hg.

Other aspects of this disclosure encompass devices that reduce the risk of traumatic brain injury from concussive events in an animal or human subject by reducing the flow of one or more neck veins by compressing at least one of said veins. The devices of this aspect comprise at least one region (i.e., a protuberance) that is inwardly directed and contacts the neck of the wearer of the device, thereby applying a localized pressure to a neck vein.

In some embodiments, the device comprises a circumferential collar sized to encircle the neck of a subject; and one or more inwardly directed protuberances integral to the collar; wherein the protuberances are located on the collar such that they are disposed above one or more neck veins of the subject when the collar is encircling the neck of the subject; and wherein the collar is sized so as to exert sufficient pressure on the protuberances to restrict blood flow egressing from the head of the subject through the one or more neck veins.

In some related embodiments, the circumferential collar is sized to be positioned between the collar bone and the cricoids cartilage of the subject.

In some related embodiments, the collar defines a cut-out sized and positioned to provide clearance for the laryngeal prominence when the collar encircles the neck of the subject.

In some related embodiments, at least a portion of the circumferential collar comprises an elastic material capable of stretching so as to increase the circumference of the collar. In some further related embodiments, the collar further comprises a compression indicator associated with said elastic material configured to provide a visual indication of the elongation of said portion when encircling the neck of the subject.

In some related embodiments, the circumferential collar comprises a rigid or semi-rigid portion defining a bridge spanning the laryngeal prominence.

In some related embodiments, the circumferential collar comprises a flexible material strap and engagement elements at opposite ends of said strap configured to be releasably engaged so as to encircle the neck of the subject. In some further related embodiments, the collar further comprises a rigid or semi-rigid portion defining a bridge over the laryngeal prominence, wherein the engagement elements at opposite ends of the strap are configured to be releasably engaged to corresponding ends of the rigid or semi-rigid laryngeal bridge. In some further related embodiments, the flexible material strap comprises an elastic material capable of being stretched so as to increase the circumference of the collar.

In some related embodiments, the circumferential collar further comprises one or more bladders disposed within the circumferential collar. In some further related embodiments, at least one of the bladders is disposed within the circumferential collar at a location other than above the protuberances. In some further related embodiments, at least one of the bladders is disposed at a location above one or more of the protuberances. In some further related embodiments, a protuberance is defined by the one or more bladders. In some further related embodiments, at least one of the bladders contains a reversibly compressible foam material, and wherein the interior of the foam-containing bladder is in fluid communication with the exterior of the bladder via a pressure relief valve. In some further related embodiments, the circumferential collar further comprises a pump element in fluid communication with a bladder, whereby the fill level of a bladder can be adjusted.

In some related embodiments, the circumferential collar further comprises a cable-tie ratcheting fit adjustment system, comprising one or more cable-tie type ratcheting tabs; and one or more receivers for said tabs, wherein each of the cable-tie type ratcheting tabs is disposed so as to pass through a receiver. The receivers are configured to allow movement of a ratcheting tab through the receiver in one direction thereby reducing the circumference of the circumferential collar, but prevent movement of the ratcheting tab in the reverse direction. Additionally, the ratcheting tabs are configured to break away from the circumferential collar at a point below their corresponding receivers when pulled away from the circumferential collar at a force greater than or equal to a predetermined level.

In some related embodiments, the circumferential collar further comprises a cable ratcheting fit adjustment system, comprising: one or more cables spanning at least a portion of the circumference of the collar; and one or more ratcheting elements, with each ratcheting element attached to at least one of the cables. In these embodiments, each of the ratcheting elements is configured to adjust the circumference of the collar by adjusting the length of a cable spanning at least a portion of the circumference of the collar. In some further related embodiments, the ratcheting fit adjustment system further comprises an adjustment tool distinct from the circumferential collar, configured to reversibly engage with the ratcheting system. In some alternative embodiments, the ratcheting fit adjustment system further comprises an adjustment tool integral to the circumferential collar.

In some related embodiments, the device further comprises one or more discernible graphic or tactile reference points on an exterior surface of the device.

In some related embodiments, the collar further comprises one or more sensors capable of detecting pulse, blood pressure, or other indicia of proper placement and pressure of a protuberance above a neck vein. In some further related embodiments, the device further comprises a transmitter operably connected to a sensor, wherein the transmitter is capable of transmitting a signal indicative of a sensor reading to an external device. In some further related embodiments, the device further comprises an electronic circuit operably connected to a sensor, whereby the electronic circuit is configured to provide visual or auditory indicia of proper fit and/or alignment. In some embodiments, visual indicia may comprise light from a light emitting diode (LED). In some embodiments, auditory indicia may comprise sound from a speaker.

In some embodiments, the device comprises a semi-circumferential collar comprising a resilient arcuate band having a general C, V, or U-shape and sized to encircle a majority of the neck of a subject; and one or more inwardly directed protuberances integral to the semi-circumferential collar. In these embodiments, the protuberances are located on the semi-circumferential collar such that they are disposed above one or more neck veins of the subject when the collar is encircling a portion of the neck of the subject; and the collar is sized so as to exert sufficient pressure on the protuberances to restrict blood flow egressing from the head of the subject through the one or more neck veins.

In some related embodiments, the collar is sized to be positioned between the collar bone and the cricoids cartilage of the subject.

In some related embodiments, the semi-circumferential collar has an opening at the front of the neck or at the back of the neck.

In some embodiments, the circumferential collar comprises (i) a pair of rigid or semi-rigid side members comprising inwardly-directed protuberances adapted to apply sufficient pressure to one or more neck veins of the subject to restrict blood flow egressing from the head of the subject through the one or more neck veins, and wherein the side members substantially oppose each other; (ii) a rigid front member having two laterally-disposed ends adapted to connect the ventral-facing ends of the pair of rigid side members and further adapted to bridge the laryngeal prominence of the subject; and (iii) a back member having two laterally-disposed ends adapted to connect the dorsal-facing ends of the pair of rigid side members. Optionally, the back member comprises an elastic material, a hinged connection with one side member and a fastening device connection with the other side member, and/or a hook-and-pile fastening system. Optionally, at least one of the back member and the front member is removable.

In some embodiments, the semi-circumferential collar comprises a pair of rigid side members comprising inwardly-directed protuberances adapted to apply sufficient pressure to one or more neck veins of the subject to restrict blood flow egressing from the head of the subject through the one or more neck veins, and wherein the side members substantially oppose each other; and a rigid front member having two laterally-disposed ends adapted to connect the ventral-facing ends of the pair of rigid side members and further adapted to bridge the laryngeal prominence of the subject.

In some embodiments, the device comprises: a flexible material sized to encircle a minority of the circumference of the neck of a subject; and one or more inwardly directed protuberances contacting an inner surface of said flexible material. In these embodiments, the flexible material is sized such that an inner surface of the flexible material extends beyond a protuberance, and the protuberances are of appropriate size and shape such that when placed on the neck above a neck vein of the subject, the device restricts blood flow egressing from the head of the subject.

In some related embodiments, the flexible material comprises a plastic or woven fabric.

In some related embodiments, a portion of the flexible material that extends beyond a protuberance is coated with an adhesive.

In some related embodiments, the flexible material is an elastic material. Alternatively, in some related embodiments, the flexible material is an inelastic material.

In some related embodiments, a protuberance is defined by an outward bend point of a resilient arcuate band having a general C, V, or U-shape.

In some related embodiments, the devices are intended to be applied to the neck of a subject in pairs. In some related embodiments, two of such devices are attached to each other by a removable tether; wherein the removable tether is sized to facilitate appropriate spacing and alignment during application to the neck of a subject.

In some embodiments, the device comprises a resilient arcuate band having a general C, V, or U-shape and sized to encircle a minority of the neck of a subject, and one or more inwardly directed protuberances. In these embodiments, when applied to the neck of a subject, the resilient arcuate band is configured to apply pressure to one or more protuberances to restrict blood flow egressing from the head of the subject.

In another aspect, the invention provides a system having a circumferential or semi-circumferential collar and the protuberances are defined by at least one pair of pads capable of being permanently or removably affixed to the collar, wherein the pads form or comprise inwardly-direct protuberances and the collar is sized to position the pads over one or more neck veins of the subject and apply constant pressure to those neck veins when worn. Optionally, the system comprises a plurality of pairs of pads (e.g., two, three, four, or more pairs of pads), wherein each pair of pads differs from each other pair of pads in the size and/or shape of the pad and/or the size and/or shape of the protuberances.

Yet other aspect discloses garments comprising: a collar sized to at least partially encircle the neck of a subject; and one or more inwardly directed protuberances integral to the collar. In such garments, the protuberances are located on the collar such that they are disposed above one or more neck veins of the subject when the garment is worn; and wherein the garment provides sufficient pressure on the protuberances to restrict blood flow egressing from the head of the subject through the one or more neck veins. In one embodiment, the protuberances are integral to the garment. Preferably, the garment comprises a turtleneck which is either elasticized or has a fitting mechanism to control the pressure exerted by the protuberances on the neck veins. In another embodiment, the garment comprises a zipper or other fastening device positioned about the neck (e.g., a jacket) to aid the subject in donning and removing the garment and/or regulating the position of and/or pressure exerted by the protuberances.

In one embodiment, the system comprises (i) a circumferential collar or semi-circumferential collar open at the laryngeal prominence, wherein the collar is adapted to be worn on the neck of a human subject and comprises inwardly-directed protuberances positioned and adapted to apply sufficient pressure to one or more neck veins of the subject to restrict blood flow egressing from the head of the subject through the one or more neck veins; and (ii) a garment with a circumferential flap, or semi-circumferential flap open at the laryngeal prominence, wherein the flap is at the neck of the garment and is adapted to fold over the collar. Optionally, the flap has an upper attachment device and lower attachment device (e.g., a hook-and-pile system), wherein the flap forms a sleeve enclosing the collar when the upper attachment device and the lower attachment device are engaged with each other. If the flap lacks the attachment devices, then the flap is adapted to merely fold over and conceal the collar while providing a layer of fabric between the collar and the neck of the subject. In an alternate embodiment, the flap at the neck opening is discontinuous and, preferably comprises a plurality of straps (e.g., 2, 3, 4, 5, or more straps) that can be secured to the body of the garment and hold the collar in place. In this embodiment, the collar may be adapted to contain holes aligned with the positioning of the straps on the garment, whereby the straps are adapted to pass through the holes to secure the collar to the garment. Alternatively, the straps are adapted to encircle the collar in order to secure the collar to the garment.

In another embodiment, the system comprises (i) a semi-circumferential collar open at the laryngeal prominence, wherein the collar is adapted to be worn on the neck of a human subject and comprises inwardly-directed protuberances positioned and adapted to apply sufficient pressure to one or more neck veins of the subject to restrict blood flow egressing from the head of the subject through the one or more neck veins; and (ii) a garment with a semi-circumferential sleeve at the neck of the garment and open at the laryngeal prominence, wherein the sleeve is adapted to removably receive the collar. Preferably, the sleeve is a tube, open at either end in an area of the garment proximal to the opening at the laryngeal prominence.

Also included in the invention are the garments described in any of the foregoing aspects.

As used herein, the term "circumferential collar" is used to describe a device which encircles the entire circumference of the neck when the device is worn by an animal or human subject.

As used herein, the term "semi-circumferential collar" is used to describe a device which encircles a majority of the circumference of the neck when the device is worn by an animal or human subject. The portion of the circumference of the neck that is not encircled by a semi-circumferential collar may be disposed at any location around the circumference of the neck, so long as the encircled portion allows for application of pressure on a neck vein of the wearer. Typically, the open portion will be located either at the front of the throat (e.g., in some embodiments, a semi-circumferential collar may encircle the neck except an area substantially defined by laryngeal prominence), or the open portion will be located at the back of the neck. Additional details are described below.

Certain aspects and embodiments of the inventive devices are described with reference to anatomical planes and descriptors which are intended to be read with reference to the device when it is worn by the user. For example, a dorsal aspect refers to an aspect of the device which is towards the subject's back when the device is worn. Likewise, terms such as "inwardly" and "outwardly" refer to aspects of the device relative to the subject, when the device is worn. For example, the protuberances may be inwardly-directed in order that they contact the neck of the subject and any advertising, logos, and tension indictors are outwardly-directed so that they can be observed by a third party.

In some embodiments, the collar may comprise a textile. In related embodiments, the collar may comprise an elastic material.

In some embodiments, the circumferential or semi-circumferential collar may comprise a semi-rigid shape-memory material, such as a suitable polymer (e.g., an elastomer) or shape-memory alloy.

In some embodiments of this aspect of the disclosure, the collar size and tension thereof can be adjustable. In some embodiments of this aspect of the disclosure, the device can further comprise one or more breakaway release mechanisms.

In some embodiments of this aspect of the disclosure, at least one region of the device inwardly directed to contact the neck of a subject can be formed by inflation of a region of the collar, and wherein the device optionally further comprises a pump to inflate the inflatable protuberance, or any region of said device, and optionally a source of pressurized gas or fluid for inflation thereof. In some embodiments of this aspect of the disclosure, the device can further comprise a release valve to regulate the pressure in said collar.

As used herein, the term “garment” refers to an article of clothing designed to be worn about the torso of the subject and comprise a customized feature designed either to hold integrated protuberances and apply pressure to the neck veins or adapted to receive and/or hold in place a circumferential or semi-circumferential collar of the invention. Garments include, for example, shirts, jerseys, and jackets with may be fully-zipped, partially-zipped, or pull-over style and optionally may be designed to be worn over protective equipment appropriate to the subject’s activity.

Another aspect of the disclosure encompasses embodiments of a method of increasing the intracranial volume and pressure of an animal or human subject comprising:

(i) encircling the neck of an animal or human subject with a collar, wherein said collar has at least one region inwardly directed to contact the neck of an animal or human subject;

(ii) positioning the at least one region inwardly directed to contact the neck on a region of the neck overlying a neck vein carrying blood from the intracranial cavity of the subject; and (iii) applying pressure to the neck vein by pressing the at least one region inwardly directed to contact the neck onto the surface of the neck, thereby restricting blood flow egressing the intracranial cavity of the subject, thereby increasing the intracranial pressure and or volume of the subject.

Further aspects of the present disclosure provides methods for mitigating injury to the inner ear, ocular structure and the spinal column, and for preventing loss of olfactory function. In the method for mitigating injury to the inner ear, pressure is applied to the jugular veins to thereby increase cochlear fluid volume and pressure during the concussive event. In the method for mitigating injury to the ocular structure, pressure is applied to the jugular veins to thereby increase intraocular fluid pressure during the concussive event. In the method for mitigating injury to the inner ear, pressure is applied to the jugular veins to thereby increase cerebrospinal fluid volume and pressure during the concussive event. Applying pressure to the jugular veins also reduces or prevents loss of olfactory sense due to increased intracranial volume and pressure.

In some embodiments of any of the foregoing aspects of the invention, the pressure applied to the neck vein may less than or equal to about 25, 30, 35, 40, 45, 50, 55, 60, 65, 70, 75, 80 mm Hg, or greater than or equal to about 5, 10, 15, 20, 25, 30, 35, or 40 mm Hg, including between about 10-80 mmHg, such as between about 10-70 mmHg, such as between about 10-60 mmHg, such as between about 10-50 mmHg, such as between about 10-40 mmHg, such as between about 15-80 mmHg, such as between about 15-70 mmHg, such as between about 15-60 mmHg, such as between about 15-50 mmHg, such as between about 15-40 mmHg, such as between about 20-80 mmHg, such as between about 20-70 mmHg, such as between about 20-60 mmHg, such as between about 20-50 mmHg, such as between about 20-40 mmHg.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1(*a*)-1(*c*) are top and side views of a compression collar according to one disclosed embodiment.

FIG. 15 shows

FIG. 27 is an illustration of another embodiment of the present invention wherein the device further comprises a sensor configured to detect pulse, blood pressure, or other indicia of proper placement and pressure of a protuberance above a neck vein, and means to transmit a signal from the sensor to an external device.

FIG. 28 is an illustration of another embodiment of the present invention wherein one or more protuberances are integral with a garment.

Figures 1A, 1B, 1C, 2, 3:
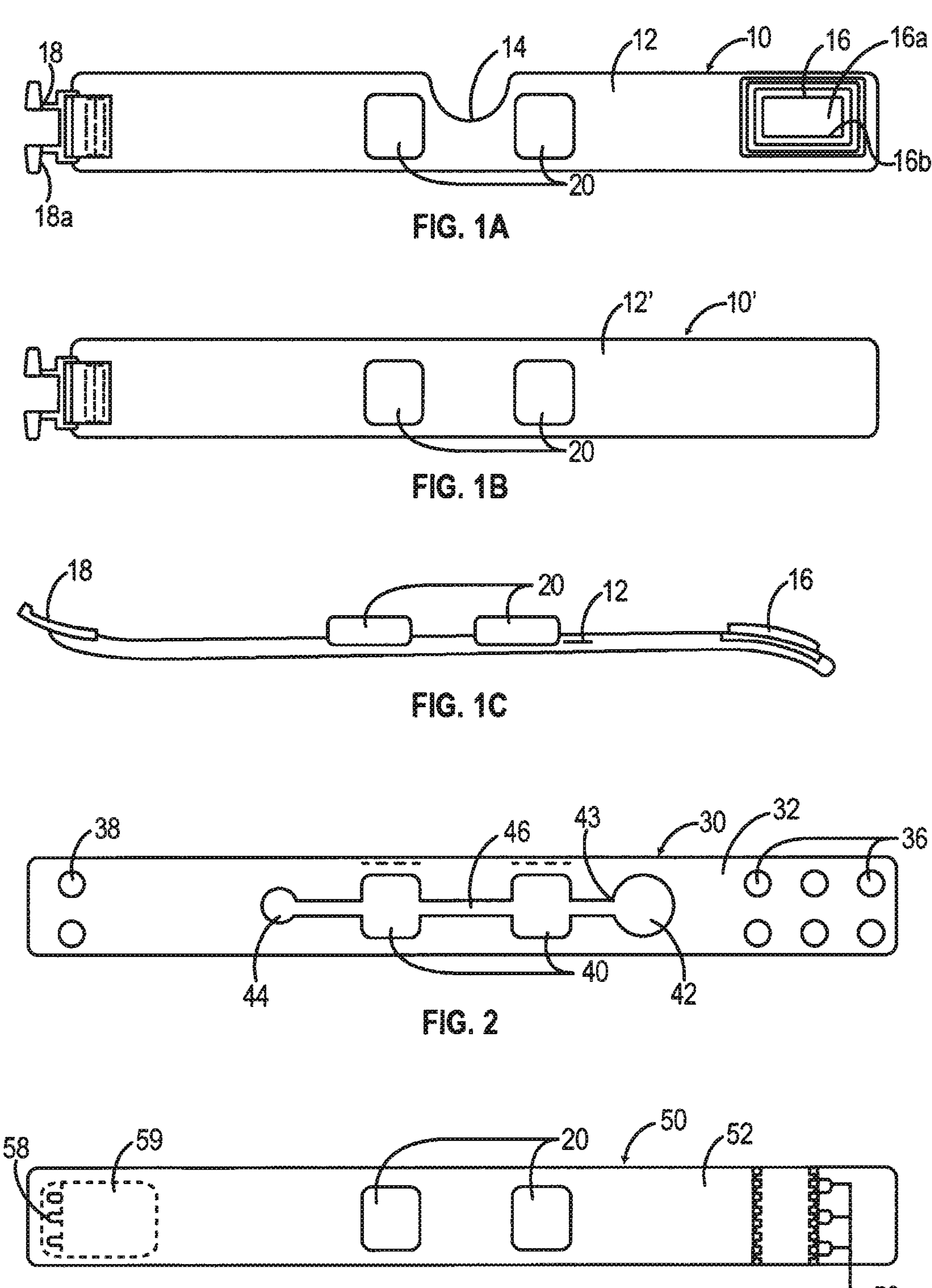
FIG. 2 is a top view of a compression collar according to a further disclosed embodiment.
FIG. 3 is a top view of compression collar according to another disclosed embodiment.

The drawings are described in greater detail in the description and examples below.

DETAILED DESCRIPTION

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

When liquid in a tank or vessel experiences dynamic motion, a variety of wave interactions and liquid phenomena can exist. The oscillation of a fluid caused by external force, termed "sloshing", occurs in moving vessels containing liquid masses. This sloshing effect can be a severe problem in energy absorption, and thus, vehicle stability and control. The present disclosure encompasses methods and apparatus for reducing SLOSH effects in living creatures, and in particular in the intracranial and spinal regions of the animal or human subject.

The mitigation of blast wave and collision damage is based largely on the principle of energy absorption of fluid-filled containers. As there becomes more room for movement of fluid within a vessel, more energy can be absorbed (SLOSH) rather than transmitted through the vessel. To reduce this energy absorption, one must attempt to more closely approximate elastic collisions. Elastic collisions are those that result in no net transfer of energy, chiefly, acoustic, kinetic, vibrational, or thermal (also stated as a coefficient of restitution (r) approximating 1.0). Various embodiments described below may locally alter, elevate, or temporarily maintain an altered physiology of an organism to reduce the likelihood of energy absorption through SLOSH whereby the coefficient of restitution (r) is increased. The coefficient of restitution (r) indicates the variance of an impacting object away from being a complete total elastic collision (an (r) of 1.0=no energy transfer). Blast or energy absorption in an organism can be viewed as a collision of bodies and thus be defined by a transfer of energies through elastic or inelastic collisions. The mechanisms for biological fluids and molecules to absorb energy can thus be identified and the resultant means to mitigate that absorption can be achieved through several SLOSH reducing techniques. Dissipation of energies post blast is also potentiated through these techniques.

SLOSH absorption may be reduced by reversibly increasing pressure or volume within the organs or cells of the organism. Applying this concept to the contents of the skull, the intracranial volume and pressure can be reversibly increased by a device that reduces the flow of one or more of the cranial outflow vessels. One embodiment of such a device would compress the outflow vessels enough to cause an increase in venous resistance, yet not enough to increase an arterial pressure leading into the cranium above approximately 80 mm Hg.

Mitigating SLOSH by increasing the pressure of the fluid contents of the brain can significantly reduce the propensity for damage to the brain tissue or its blood vessels by reducing the compressibility of the brain. The reduction in compressibility results in reduced absorption of kinetic, acoustic, thermal, and vibrational energy by the brain.

Intracranial volume can also be reversibly increased by increasing the $pCO_2$ in the arterial blood or by the delivery of one or more medicaments to facilitate an increase in intracranial volume or pressure including but not limited to Minocycline, insulin-like growth factor 1, Provera, and Vitamin A. Such techniques may be used in combination with use of the devices disclosed herein.

With respect to the inner ear, it is known that the cochlear aqueduct is in direct communication with the cerebrospinal fluid (CSF) and the vein of the aqueduct drains directly into the internal jugular vein (IJV). The venous blood empties either directly into the inferior petrosal sinus or internal jugular vein, or travels through other venous sinuses via the vein of the vestibular or cochlear aqueduct. Reduced outflow of the internal jugular would necessarily congest the cochlear vein and take up the compliance of the inner ear, thereby improving elastic collisions at the macroscopic, cellular, and molecular level and, thus, reducing energy impartation into these structures.

Approximately 30 ml (21%) of a total CSF volume of 140 ml resides within the spinal axis, and about one-third of the compliance of the CSF system has been attributed to the spinal compartment. As in the brain, increasing the pressure and volume of the CSF within the spinal compartment reduces the susceptibility of the spinal compartment to concussive injuries by increasing the elasticity of the contents of the spinal column, thereby reducing the amount of energy absorbed by the contents of the spinal column when subjected to a concussive force.

With respect to ocular injuries, it is known that the woodpecker has a "pectin apparatus" that protects the globe of its eyeball from the 1200 G impact of pecking. The sole purpose of the pectin apparatus appears to be to increase the volume and pressure of the vitreous humor inside the eyeball. The pectin apparatus is situated within the eyeball and fills with blood to briefly elevate intraocular pressure, thereby maintaining firm pressure on the lens and retina to prevent damage that might otherwise occur during the 80 million pecking blows over the average woodpecker's lifetime. While humans lack the pectin apparatus, it is possible to increase intraocular pressure by externally applying pressure on the external jugular veins (EJV).

One aspect of the present invention, therefore, encompasses a device that raises intracranial volume and pressure and/or intraocular pressure when worn by a subject animal or human. The device is configured to apply pressure to the outflow vasculature in the neck (e.g., one or more internal and/or external jugular vein), thus increasing intracranial and/or intraocular pressures and volumes in the wearer. In doing so, the device reduces energy absorption by the wearer due to concussive effects, thus reducing the likelihood of one or more of brain, spine, and eye damage from a concussive event. Devices of the instant invention could be worn preferably before, in anticipation of and during events with SLOSH and traumatic brain injury risks.

Safely and reversibly increasing cerebral blood volume by any amount up to 10 $cm^3$ and pressure by any amount up to 70 mmHg would serve to fill up the compliance of the cerebral vascular tree and thus reduce the ability to absorb external energies through SLOSH energy absorption. With the application of measured pressure to the neck, the cranial blood volume increases rapidly and plateaus at a new higher level. Moyer et al reported that cerebral arterial blood flow was not affected by obstructing the venous outflow of blood from the brain. The blood volume venous pressure relationship shows a diminishing increase in volume with each increment of neck pressure over the range 40 to 70 mm of mercury. It is of interest that the cranial blood volume increases from 10 to 30 percent (with this neck pressure). Similarly, CSF pressure also increases upon compression of the individual jugular veins. Under the same neck pressure, the average rise in CSF pressure is about 48%. These changes occur very rapidly upon initiation of pressure; jugular compression increases cerebral blood flow to a new plateau in as little as 0.5 seconds. Although lesser cranial pressure and volume increases may still have beneficial effects, it is intended that devices of the instant invention increase cranial blood volume by at least 3 $cm^3$ through an application of at least 5 mm Hg neck pressure.

Devices of the present invention, therefore, may take many forms, but share the functional feature of constantly or intermittently applying pressure to one or more veins in the neck (specifically, but not limited to the internal and external jugular veins, the vertebral veins, and the cerebral spinal circulation, and most preferably, the interior jugular vein) to restrict blood flow exiting the brain. Thus, the instant devices include at least one inwardly directed protuberance that is inwardly directed and contacts the neck of the wearer of the device, and at least one means for applying pressure to the one or more protuberances such that the protuberances apply pressure to one or more veins in the neck, thereby restricting blood flow exiting the brain.

Inwardly Directed Protuberances that Contact the Neck of the Wearer

In some embodiments, the one or more inwardly directed protuberances are integral to the component of the device responsible for applying pressure to the neck. In alternative embodiments, the one or more inwardly directed protuberances are distinct from the component of the device responsible for applying pressure to the neck. Is to be generally understood that the protuberances may be any suitable shape, e.g., pointed or round, and comprising of any suitable material, such as defined by a rigid or semi-rigid plastic body, a thickened region of a collar, and the like.

In some embodiments, the protuberances may substantially be defined by a bladder, whereby pressure is exerted on the neck of the wearer when the bladder is inflated or filled. In some related embodiments, the bladder may contain reversibly compressible foam that is in fluid communication with the external atmosphere. In further related embodiments, the interior of the bladder is in fluid communication with the external atmosphere via a pressure release valve. In embodiments comprising a bladder, foam, and valve, these components may be configured so that the foam expands within the bladder, drawing air into the bladder through the pressure valve to inflate the bladder to a desired pressure. However, the pressure release valve may be configured to allow for release of air from the bladder upon an application of pressure to the device that may otherwise raise the amount of pressure applied to the neck to an uncomfortable or undesirable level. In other embodiments, the bladder may contain a gas or liquid and may be outfitted or configured to interface with a pump mechanism such that the pressure of the bladder may be user adjusted. The pump mechanism may be any suitable pump mechanism as would be understood in the art, such as e.g., a powered pump, or a hand-compressible pump whereby a liquid, air or a gas can be applied to the bladder. In certain embodiments the device may further comprise a pressure sensor operably linked to the pump mechanism or bladder whereby the degree of inflation may be regulated as to the extent and duration of the pressure applied to an underlying neck vein.

In some embodiments, the protuberance comprises a spring or resilient compressible material. In these embodiments, the spring or resilient compressible material is disposed within the protuberance such that application of the protuberance to the neck at least partially compresses the spring or resilient compressible material. The force exerted by the at least partially compressed spring or resilient compressible material ensures that the protuberance maintains a desired pressure on the neck.

In some embodiments, the device may comprise a resilient arcuate band having a general C, V, or U-shape. The band may be formed of a resilient spring-like material whereby the C, V, or U-shaped band is forced open as the device is applied. After application of the device, spring tension causes compression of the band, resulting in the mid-point or bend-point of the band to extend toward and apply pressure to the neck. Thus, in these embodiments, the mid-point or bend-point of the bands are the protuberances that contact the neck of the wearer.

In some embodiments, at least a portion of an inwardly directed surface of the one or more protuberances may be coated with a suitable adhesive to facilitate placement of the protuberances on the neck, and prevent movement of the protuberance once in place. Additionally or in the alternative, in embodiments where the protuberances are distinct from the component of the device which applies pressure to the neck, at least a portion of an outwardly directed surface of the one or more protuberances may be coated with a suitable adhesive. In such embodiments, the design of the device may such that a protuberance may be paced between a component which applies pressure to the neck and the neck itself. An outwardly directed surface of the protuberance would then contact an inwardly directed surface of the pressure-providing component of the device such that the adhesive on the outwardly directed surface of the protuberance would prevent movement of the protuberance once in place.

One exemplary embodiment of this type (discussed in greater detail below) comprises three pieces: two round or oval plastic protuberances (one for application to either side of the neck) and an elastic collar. The device could be applied by first putting the collar around the neck, and then by placing the plastic protuberances between the collar and the neck at the appropriate locations so as to apply pressure to the internal jugular vein on either side of the neck. As will be appreciated for this example, a mild adhesive coating on the inwardly directed and/or outwardly directed surfaces of the protuberances will assist in preventing movement of the protuberances once they are installed between the collar and the neck. Alternately, if the protuberances have an adhesive coating of sufficient strength at least on the inwardly directed surfaces, the protuberances may be placed on the appropriate locations on the neck prior to installation of the collar. In either case, the collar applies pressure to the protuberances, which in turn applies pressure to the neck veins.

In other embodiments of this type, two protuberances may be secured to one another with a tether of the appropriate length to act as an alignment and spacing guide for application on either side of the neck. In some embodiments, the tether may be removable, so that once the protuberances are applied to the neck, the tether may be pulled or otherwise removed, leaving the protuberances in place on the neck of the wearer.

In some embodiments, the protuberances are compressible pads or solid forms sized to apply pressure substantially only to the internal jugular vein.

Circumferential and Semi-Circumferential Collar Type Devices

In some embodiments, the device may be a circumferential or semi-circumferential collar. A circumferential collar is a collar that encircles the entire circumference of the neck when the device is worn by an animal or human subject. A semi-circumferential collar is a collar that encircles a majority of the circumference of the neck when the device is worn by an animal or human subject. The portion of the circumference of the neck that is not encircled by a semi-circumferential collar may be disposed at any location around the circumference of the neck, so long as the encircled portion allows for application of pressure on inwardly directed protuberances specifically located in order to restrict blood flow exiting the brain. Typically, the open portion will be either located at the front of the throat (e.g., in some embodiments, a semi-circumferential collar may encircle the neck except an area substantially defined by laryngeal prominence, also known as the "Adam's apple"), or located at the back of the neck.

In embodiments where the device comprises a circumferential collar, it is contemplated that the applied pressure to the neck may be due to an internal dimension of the collar being less than the neck diameter. This difference in internal dimension of the collar may be achieved by any number of configurations dictated by the materials used to construct the collar. For instance, in a collar comprising inelastic materials, the collar may be sized to apply the appropriate pressure when worn by an individual. In these embodiments, the size of the collar may be such that the collar is tailored to an individual and thus requires no adjustment for fit. Alternatively, the size of the collar may be adjustable by any of a number of means, some of which are discussed further below. In some embodiments, the collar may comprise an elastic material such that the internal dimension of the elastic collar is expanded when the collar is worn, and the collar applies pressure to the neck of the wearer as a result of compressive force exerted by the expanded elastic material. Elastic materials may also confer the benefit of increased comfort for the wearer.

In embodiments where the device comprises a semi-circumferential collar, it is contemplated that the collar comprises a resilient arcuate band having a general C, V, or U-shape. In these embodiments, it is intended that the band extend a majority, if not the entirety, of the length of the collar. In these embodiments, the collar thus semi-rigidly defines a C, V, or U-shape that is expanded as the collar is applied to the neck of a wearer. Spring tension from the expanded resilient arcuate band causes a compressive force that keeps the collar in place on the neck and applies the intended pressure to the neck veins.

In these embodiments, at least one inwardly directed pad or form may be disposed at appropriate locations on opposing sides of the collar, such that the inwardly directed pads or forms are configured to contact the neck and apply pressure to a point above the interior jugular vein. In embodiments where the semi-circumferential collar is open at the front of the throat, the area of the neck not covered by the semi-circumferential collar may define a region approximating the laryngeal prominence, also known as the "Adam's apple." In these embodiments, the inwardly directed pad or forms disposed on opposing sides of the collar may be located at or near the terminal ends of the resilient arcuate band. In embodiments where the semi-circumferential collar is open at the back of the neck, the inwardly directed pads or forms may not be disposed near the terminal ends, but rather may be disposed much closer to the mid-point of the band.

In some embodiments where the device comprises a circumferential collar or a semi-circumferential collar that is open at the back of the neck, the device may comprise a laryngeal bridge that defines a cut-out at the front of the neck. The size and shape of the laryngeal bridge may be configured so as to minimize contact of the collar with the laryngeal prominence in order to make the collar more comfortable for the wearer. In these embodiments, the laryngeal bridge may be of any suitable material as to provide a rigid or semi-rigid continuation of the collar around the front of the neck. In some embodiments, the laryngeal bridge may comprise thick or reinforced textile material, plastic, metal, or any combination thereof.

In some embodiments where the device comprises a circumferential collar, the device comprises two components: a front section comprising the one or more inwardly directed protuberances and a laryngeal bridge, and a back section comprising a length of fabric configured to be removably attached at either end to corresponding ends of the front section. In some embodiments, the length of fabric comprises an elastic material; alternatively, the length of fabric may comprise an inelastic fabric. Removable attachment of either end of the front section to the corresponding end of the back section may be by any suitable method known in the art, such as a hook and ladder attachment, a hook and loop attachment, a snap, a button, a chemical adhesive, or any of a number of attachment mechanisms that would be known to one skilled in the art. A device with removable attachment means could also have a breakaway release mechanism whereby the device can break open or apart at a predetermined force to prevent the device from inadvertently being snagged or compressing too tightly.

Many of the devices described herein are described as potentially comprising an elastic material. More particularly, it is intended that these devices may comprise materials that are elastically elongatable around the circumference of a subject's neck. Elastic materials can be any material which when stretched will attempt to return to the natural state. Exemplary materials may include one or more of textiles, films (wovens, non-wovens and nettings), foams and rubber (synthetics and natural), polychloroprene (e.g. NEOPRENE®), elastane and other polyurethane-polyurea copolymerss (e.g. SPANDEX®, LYCRA®), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. There are also a number of elastic materials which are breathable or moisture wicking which may be preferable during extended wearing periods or wearing during periods of exercise. As indicated above, elastic materials may confer the benefit of increased comfort for the wearer by providing sufficient compressive pressure, yet remaining flexible to accommodate a full range of motion and/or muscle flex in the wearer.

In addition, a device constructed with an elastic material may be partially reinforced, coated, or otherwise include one or more protecting materials such as Kevlar® (para-aramid synthetic fibers), Dyneema® (ultra-high-molecular-weight polyethylene), ceramics, or shear thickening fluids. Such reinforced materials may confer the benefit of increasing the devices resistance to lacerations. As such, reinforced devices may provide the user the added benefit of protecting the neck from damage from lacerations.

In some embodiments, circumferential or semi-circumferential collars may be constructed with materials, elastic or otherwise, that are fire resistant.

The device may encompass horizontally, the entire neck or just partially up and down the neck. The width of the devices described herein may range from a mere thread (at a fraction of an inch) to the length of the exposed neck (up to 12 inches in humans or greater in other creatures), the length may range from 6 to 36 inches to circumnavigate the neck. The width of the compression device could be as small as ¼ inch but limited only by the height of the neck in largest width, which would be typically less than 6 inches. The thickness of said device could range from a film being only a fraction of a millimeter to a maximum of that which might be cumbersome yet keeps ones neck warm, such as 2-3 inches thick.

One embodiment of the device may be pre-formed for the user in a circular construct. This one size fits all style can have a cinch of sorts that allows one to conform the device to any neck size. Alternatively the device may have a first end and a second end which are connected by a fastener. A fastener may be magnetic, a tack strip, a hook and ladder attachment, a hook and loop attachment, a ply strip, one or more slide fasteners, one or more zippers, one or more snaps, one or more buttons, one or more safety pin type clasp mechanisms, overlapping electrostatic contact materials, or any of a number of attachment mechanisms that would be known to one skilled in the art. A device with a fastener could have a breakaway release mechanism whereby the device can break open or apart at a predetermined force to prevent the collar from inadvertently being snagged or compressing too tightly. One quick release or automatic release embodiment would be the applying of small amounts of hook and ladder attachments within a circumferential ring which would shear apart upon too much force being applied to the device.

Another embodiment of the device could fasten such that the user would be able to pull one end of the collar (like a choker collar for a dog) and the force exerted by the user effectually decreases the length or circumference of the device. When the desired neck compression is no longer needed (such as between football plays) the user could then release the compression by a second gentle tug or by a separate release mechanism also positioned on the device.

Other fit adjustment systems may be used in the collar-type devices described herein. For example, in one embodiment, a pull-away cable-tie (e.g., Zip-tie®) type ratcheting fit adjustment system may be included. This type of system may include one or more pull-away cable-ties configured to release from the collar when pulled at or above a specific pressure, thus ensuring that the collar is not over tightened. In alternate embodiments, a rotating ratcheting fit adjustment system may be included. In such embodiments, system may be designed such that an external tool is employed fit adjustment. Preferably, such systems utilize elastic materials and or an adjustable fastener system (as described above) such as a Velcro® closure-system to provide a gross-fit of the device. The ratcheting adjustment system would then be used for fine-adjustments of the device specific for an individual wearer. As an alternative to an external tool system, rotating ratchet fit adjustment systems which include an integrated adjustment dial, e.g., a BOA® rotating ratchet fit adjustment system as described in U.S. Pat. No. 8,381,362 and U.S. Pat. Pub. No. 2012/0246974.

In some embodiments, a circumferential or semi-circumferential collar may comprise a shape memory polymer. In such embodiments, the collar would be applied to the neck of a user and then the appropriate stimulus would be applied to the shape memory polymer, causing the collar to shrink to fit.

In some embodiments, a circumferential or semi-circumferential collar may comprise a bladder whereby the pressure exerted on the neck of the wearer by the collar may be adjusted by inflating or deflating the bladder. In some related embodiments, the bladder may contain reversibly compressible foam that is in fluid communication with the external atmosphere. In further related embodiments, the interior of the bladder is in fluid communication with the external atmosphere via a pressure release valve. In embodiments comprising a bladder, foam, and valve, these components may be configured so that the foam expands within the bladder, drawing air into the bladder through the pressure valve to inflate the bladder to a desired pressure. However, the pressure release valve may be configured to allow for release of air from the bladder upon an application of pressure to a protuberance that may otherwise raise the amount of pressure applied to the neck to an uncomfortable or undesirable level. In other embodiments, the bladder may contain a gas or liquid and may be outfitted or configured to interface with a pump mechanism such that the pressure of the bladder may be user adjusted. The pump mechanism may be any suitable pump mechanism as would be understood in the art, such as e.g., a powered pump, or a hand-compressible pump whereby a liquid, air or a gas can be applied to the bladder. In certain embodiments the device may further comprise a pressure sensor operably linked to the pump mechanism or bladder whereby the degree of inflation may be regulated as to the extent and duration of the pressure applied to an underlying neck vein. In some embodiments, the bladder is disposed to at least include a portion of the collar other than above a protuberance. In some embodiments, the bladder is disposed through a majority of the circumference of the collar.

In some embodiments, a circumferential or semi-circumferential collar may further comprise a pouch or pocket. This pouch or pocket may be externally accessible, i.e., accessible while the collar is being worn, or only accessible when the collar is removed. The dimensions of such a pouch or pocket may be such that the pouch or pocket is suitable to carry one or more items useful for the treatment of TBI related calamities, such as a material enabling $CO_2$ delivery, carbonic anhydrase tablets, methylene blue, DHA, smelling salts, etc.

In some embodiments, a circumferential or semi-circumferential collar may further comprise an electrical circuit comprising a piezoelectric heat pump configured to alter the temperature of the inwardly directed surface of the collar. Such a heat pump may be used to either heat or cool the device, for example by as much as 70° from ambient temperature.

In some embodiments, a circumferential or semi-circumferential collar may further comprise an electrical circuit configured to provide a therapeutic electrical stimulation to the neck of the wearer. For example, an electrical circuit may be configured to provide transcutaneous electrical nerve stimulation.

Non-Collar Type Devices

In some embodiments, the device may be a non-collar type device. Non-collar type devices are those that cover or encircle a minority of the circumference of the neck when the device is worn by an animal or human subject. However, the portion of the circumference of the neck that is covered or encircled by non-collar type devices must at least include one or more areas of the neck above a neck vein, as described above. As with collar-type devices, non-collar type devices also utilize inwardly directed protuberances to apply pressure to the neck at specific locations in order to restrict blood flow exiting the brain. Any of the protuberances described above may find use in non-collar type devices.

In some embodiments, the externally directed side of a protuberance may be covered by flexible material that extends beyond the area defined by the protuberance. In these embodiments, at least a portion of this extended inwardly directed surface contacts the neck when the device is in place. In some embodiments, the at least a portion of the inwardly directed surface of the flexible material that contacts the neck is coated with an appropriate adhesive, such that when applied to the neck, the flexible material holds the protuberance in an appropriate position and applies pressure to a neck vein. The flexible material may be elastic or non-elastic. The flexible material may be any suitable synthetic or natural woven or textile material, or any suitable plastic.

Such embodiments may comprise a pair of material/protuberance combinations for application to both sides of the neck. Some related embodiments may comprise a pair of material/protuberance combinations joined by a tether, as described above. The tether may be of appropriate length so as to serve as an aid to alignment and proper placement of the protuberances at the correct locations on the neck. In some embodiments, the tether may be removably attached to the pair of material/protuberance combinations so that after placement of the protuberances on either side of the neck, the tether is removed.

In some non-collar type devices, the device may comprise a resilient arcuate band having a general C, V, or U-shape. In these embodiments, it is intended that a protuberance is located at or near the terminus of each arm of the band, and that when the device is in place, the band extends around the front of the neck. In these embodiments, the band thus semi-rigidly defines a C, V, or U-shape that is expanded as the device is applied to the neck of a wearer. Spring tension from the expanded resilient arcuate band causes a compressive force that keeps the device in place on the neck and applies the intended pressure to the neck veins via the protuberances. In some embodiments, the resilient arcuate band is sized and shaped such that it does not cross the front of the neck in the general area of the laryngeal prominence. Instead, the band may cross the front of the neck at a position below the laryngeal prominence.

Garments or Other Protective Gear Comprising Integral Protuberances

In yet other embodiments, it is envisioned that protuberances (as described above) may be incorporated into various articles of clothing and/or other protective gear. Such garments and/or other protective gear typically may be designed for specific purposes, e.g., as part of a military uniform, sporting apparel, neck guard for first responders, flame retardant head gear for automobile or motorcycle drivers or firefighters, etc. In any case, protuberances may be included at the appropriate positions in a portion of a garment or protective gear that contacts the neck of the wearer, i.e., the collar, with the collar providing compressive force on the protuberances. As such, any of the closing, alignment, or fitting means, or any other optional feature provided in regards to circumferential or semi-circumferential collar-type devices may be incorporated in garment and/or protective gear embodiments.

In one aspect, the invention provides a system having a garment and a circumferential or semi-circumferential collar, each adapted for use with the other. In one embodiment, the garment has a top portion adapted to receive the collar. For example, the top portion of the garment may have an extended flap which is designed to provide a layer of fabric between the subject's neck and the collar, wherein the extended portion of that flap is folded over, and optionally fastened, to conceal the collar and help hold the collar in place. In another embodiment, the top portion of the garment has a sleeve which is adapted to receive the collar. In another embodiment, the collar is place directly against the subject's skin and the top portion of the garment is adapted to conceal all or part of the collar. Optionally, the inside of the garment and the outside of the collar have a mutually engaging fastening means in order to hold the top portion of the garment in place against the collar. One such suitable fastening means is a hook-and-pile system (e.g., VELCRO®).

In another aspect, the top portion of the garment has integral protuberances permanently affixed therein. Optionally, the top portion of the garment comprises a rigid or semi-rigid member, similar to the stand-alone collar, adapted to apply neck vein pressure via the protuberances. Alternatively or in addition to the rigid member, the top portion of the garment may be fully circumferential with a closing and/or fitting mechanism adapted to apply and control neck vein pressure via the protuberances.

Visual or Tactile Alignment Aids

Any of the embodiments described above may further comprise one or more materials, and/or apply one or more construction methods, designed to provide the user or a 3$^{rd}$ party observer with a visual or tactile aid in determining proper alignment and positioning of the protuberances. For instance, a collar type device may include a small strip or patch of a contrasting or reflective material, or a material with a different texture, at the mid-point of the neck. Alternatively or in addition, similar visual or tactile cues may be incorporated into any of the above devices so as to provide an outward indication of the location of a protuberance.

Further, any of the embodiments described above that utilize elastic materials may comprise a dual layered elastic material that exposes a change in graphic or color when sufficiently stretched to apply an appropriate force on an underlying protuberance. In such embodiments, the change in graphic or color may provide a visual cue to the wearer or 3$^{rd}$ party observer that the device is applying at least sufficient compressive force.

Incorporated Sensors or Other Electronic Systems

Any of the above devices may also have one or more monitoring, recording, and/or communicating devices attached or embedded. For example, the device may comprise a sensor capable of detecting one or more environmental parameters around the wearer, one or more physiological parameters of the wearer, or some combination thereof. Exemplary environmental parameters that may be detected include time the collar has been worn, barometric pressure, ambient temperature, humidity, acceleration/deceleration (i.e., G forces), positionality (upright/supine), etc. Physiological parameters that may be detected include pulse, blood pressure, plethysmography, dermal temperature, oxygen saturation, carboxyhemoglobin level, methemoglobin level, blood sugar, electrical flow, etc. of the human or animal wearing the device. Any of such sensors may be used to monitor some environmental or physiological characteristic or performance aspect of the wearer. Sensors capable of detecting pulse, blood pressure, and/or plethysmography may serve the additional or alternate purpose of being used as an alignment and/or fit aid, notifying the user when the protuberance is properly placed over a neck vein and is exerting an appropriate pressure so as to restrict blood flow.

In some related embodiments, a device may further comprise an electronic circuit capable of providing visual, auditory, or tactile indicia of malfunction, or an undesirable sensor reading. For instance, an electronic circuit may be configured to vibrate the collar when a pulse or blood pressure sensor detects a reading that is either higher or lower than a predetermined value.

Additionally or in the alternative, any of the above devices may comprise an electronic circuit configured to transmit the location of the wearer. For instance, any of the above devices may comprise an electronic circuit configured to transmit the GPS coordinates of the wearer for tracking the location of the wearer, or for search and rescue purposes.

Additionally or in the alternative, any of the above devices may comprise an electronic circuit configured to transmit and/or receive voice communications between the wearer and a third party.

In some embodiments, the output of such a sensor may be visually or audibly communicated to the user or a 3$^{rd}$ party by another component of the device, e.g., an electronic circuit configured to provide a visual or auditory indication (such as with an LED, piezoelectric speaker, etc.). In some embodiments, the device further comprises a communication means such that a signal from the sensor may be communicated to an external electronic device, such as a smartphone, laptop, or dedicated receiver.

These terms and specifications, including the examples, serve to describe the invention by example and not to limit the invention. It is expected that others will perceive differences, which, while differing from the forgoing, do not depart from the scope of the invention herein described and claimed. In particular, any of the functional elements described herein may be replaced by any other known element having an equivalent function.

EXEMPLARY EMBODIMENTS

Particular embodiments of a collar type device are illustrated in FIGS. 1-3. Referring to FIGS. 1(*a*)-(*c*), a compression collar 10 includes an elongated strap 12 that may be provided in various sizes to encircle the neck of the animal or human subject. In one specific embodiment the strap may be provided in standard lengths of 14, 16 and 18 inches to fit the normal range of neck sizes for humans. The width in a specific example may be about 1.5 inches to fit within the anatomy of the neck below the laryngeal prominence. To minimize the prominence of the collar, the strap may have a thickness of about 0.12 inches. The strap 12 may be formed of a woven, breathable, dermatologically inert and non-irritating material, such as cotton or certain polyesters. Since the strap is intended to apply consistent pressure to the jugular vein of the subject the strap material is preferably generally elastic, but formed of an elastic material that will not permanently stretch appreciably over time. It can be appreciated that stretching the material so that the neutral length of the strap is longer than its original condition can render the strap 12 useless. On the other hand, the strap material must be sufficiently elastic or elastically elongatable to remain comfortable when worn for a long period of time, and to flex appropriately with the muscles of the neck. The effective length of the strap 12 is made adjustable by the addition of adjustable engagement elements 16 and 18 at opposite ends of the strap. For instance, in the embodiment shown in FIG. 1(*a*) the latch element 16 defines a serrated channel 16*a* that receives the resilient prongs 18*a* of the other element. The prongs 18*a* are biased to provide an outward force against the channel 16*a* of the latch to hold the prongs at the location of a particular serration 16*b*. In the illustrated embodiment, seven serrations are depicted which provide seven locations for engagement of the prongs 18*a* for fine adjustment of the length of the collar. The two components 16, 18 may be sewn onto the strap 12 or permanently affixed in a conventional manner sufficient so that the engagement elements will not pull free from the strap during use.

Two versions of the collar are depicted in FIGS. 1(*a*) and 1(*b*). The version of FIG. 1(*a*) is provided for a male human and includes a cut-out 14 at the location of the laryngeal prominence. The strap 12' of FIG. 1(*b*) does not include the cut-out and may be typically provided for female human subjects. The cut-out may have a width of about 1.5 inches and a depth of about 0.5 inches to accommodate the typical laryngeal prominence. It can be appreciated that the collar 10 is engaged around the neck of the subject so that the cut-out 14 is below and sufficiently clear of the prominence to avoid any discomfort to the subject.

In a further feature of the collars 10, 10', a pair of compressible pads 20 are provided spaced apart across the midline of the strap 12, 12'. The pads are sized and located to bear against the neck at the location of the jugular veins. In one embodiment the pads are spaced apart by about 2.5 inches, have a width/length dimension of 1.0-1.5 inches and a thickness of about 0.04 inches. As shown in FIG. 1(*c*) the pads may be partially embedded within the strap 12. The pads 20 may be formed of a breathable foam that exhibits good recovery from compression. The pads may be formed of a material capable of exerting compression of 5-30 mm Hg when the collar is worn, such as a flexible polyurethane foam.

Additional embodiments of the compression collar are shown in FIGS. 2 and 3 that incorporate different engagement elements. For instance, the collar 30 of FIG. 2 incorporates an array of snap pairs 36 at one end that engage a pair of snaps 38 at the opposite end. The snap pairs 36 may be spaced at pre-determined intervals, such as at ¼ inch spacings to permit adjustment of the collar diameter when worn. The collar 50 in FIG. 3 incorporates a row of hooks 56 at one end that engage a corresponding row of loops 58 at the opposite end. The embodiment of FIG. 3 illustrates that the engagement elements need not be adjustable, although adjustability is preferred. In the embodiment of FIG. 3 this adjustability may be accomplished by a VELCRO® type connection between the strap 52 and the row of loops 58. In particular, a VELCRO® type pad interface 59 may be used to mount the loops 58 to the strap at different positions along the length of the strap. In a further alternative, the VELCRO® interface may be between the two ends with mating VELCRO® type pads on each end.

In one aspect of the compression collars disclosed herein, the engagement elements are preferably configured to break loose or disconnect at a certain load, to avoid the risk of choking or damaging the subject's neck and throat if the collar is snagged or grabbed. Thus, the engagement elements 16, 18 of FIG. 1, the snaps 36, 38 of FIG. 2 and the hook attachment 59 of FIG. 3 can be calibrated to disconnect when the collar is pulled with sufficient force. In a further embodiment, the engagement elements, such as snaps 36, 38, may be replaced by magnets or a magnet array. The magnets are strong enough to maintain the desired pressure on the jugular veins when the collar is in use. The magnet strength may be calibrated to break loose at a certain load. The break-away feature may also be integrated into the strap apart from the engagement elements. For instance, the strap may incorporate a region between a pad 20 and an engagement element that has a reduced strength so that the strap tears under a certain load. Alternatively, a non-adjustable engagement may be provided in this region calibrated to disengage at a predetermined load.

In the embodiments of FIGS. 1 and 3, the jugular vein is compressed by the pad 20. The pad has a predetermined thickness and compressibility. In an alternative embodiment, the pads are replaced by inflatable bladders 40, as shown in FIG. 2. In this embodiment a fluid line 46 connects the bladders to a pump 42 and a release valve 44. The pump 42 can be of the type that is manually squeezed to draw atmospheric air into the bladders. A one-way valve 43 is provided in the fluid line 46 at the pump 42 to maintain the increasing air pressure within the bladders. The pump 42 may be constructed similar to a small engine primer bulb. The pump may be configured to be manually depressed while the collar is being worn. The release valve 44 may be manually activated to relieve the bladder pressure. The release valve may also be configured to automatically vent when a certain pressure is reached to prevent over-inflating the bladders 40.

In an alternative embodiment the pump 42 may be a microfluidic pump embedded within the strap 32. The pump may be electrically powered by a battery mounted within the collar or may be remotely powered such as by an RF transmitter placed adjacent the collar. The pump may be remotely controlled by incorporating a transmitter/receiver within the collar. The receiver may transmit pressure data indicating the fluid pressure in the bladders 40 and the receiver can receive remotely generated commands to activate the pump 42 to increase the pressure to an appropriate value. It is further contemplated that the pump 42, whether manually or electrically operated, may include a pressure gage that is readable on the outside of the collar to assist in inflating the bladders to the desired pressure.

The illustrated embodiments contemplate a collar that completely encircles the neck of the subject. Alternatively the compression device may only partially encircle the neck. In this embodiment the device may be a resilient arcuate band having a general C-shape. The band may be formed of a resilient spring-like material with the compression pads mounted to the ends of the C-shape. The device would thus function like a spring clip to exert pressure against the jugular vein. The spring effect of the C-shape can also help hold the device on the subject's neck, preferably on the back of the neck for better anatomic purchase.

Figures 4, 5, 6, 7A, 7B, 7C:
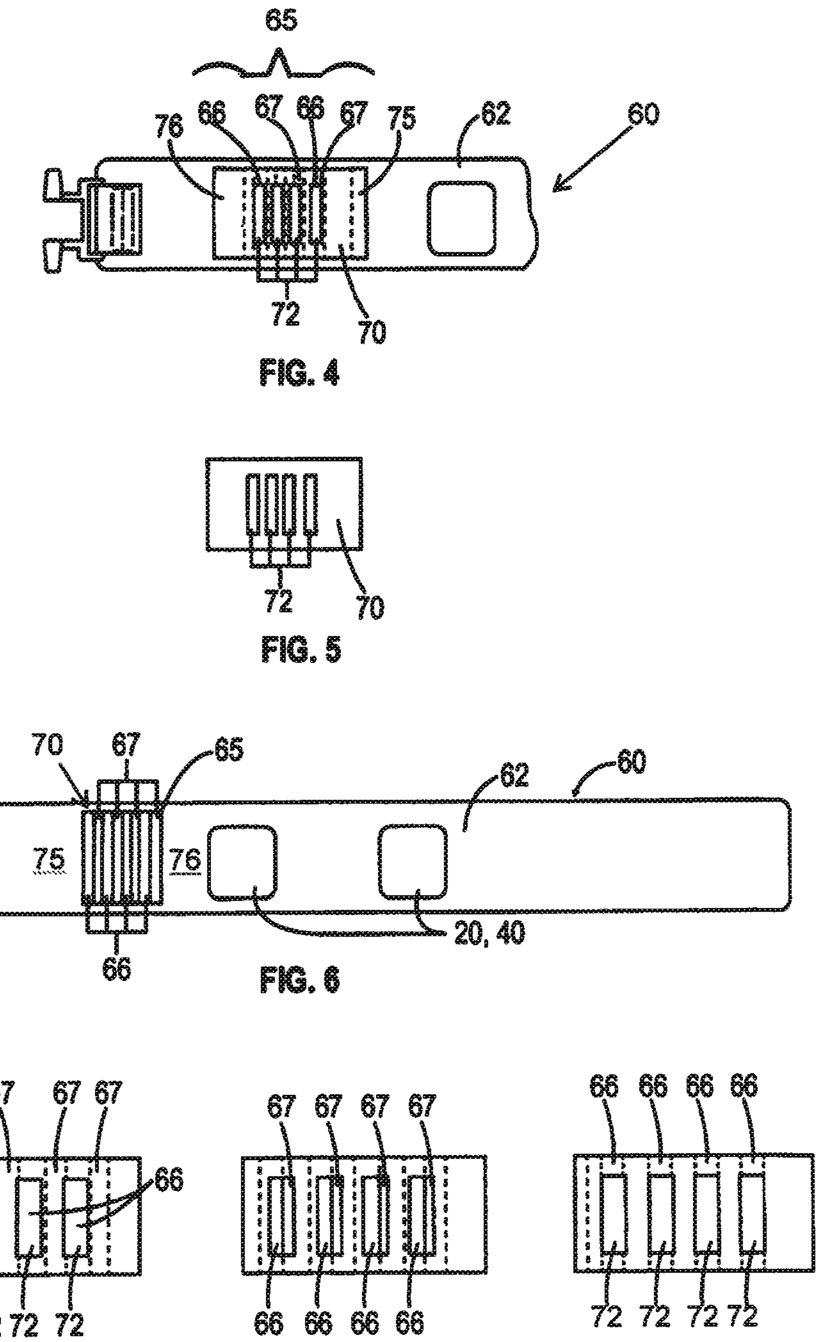
FIG. 4 is a top view of a compression collar of another embodiment incorporating a compression indicator.
FIG. 5 is a top view of an overlay to be mounted on the collar of FIG. 4.
FIG. 6 is a top partial view of the compression collar and overlay of FIGS. 4-5.
FIGS. 7A-C are successive views of the overlay and indicator strips of the compression collar shown in different degrees of stretch of the collar.

A compression collar 60, shown in FIG. 4, may incorporate a visual compression indicator that can be visualized when the collar is fitted on a user. The collar 60 includes a strap 62 that may be configured like the straps 12, 32, 52 described above, and may incorporate compression pads 20, 40 arranged to apply pressure to the jugular vein when the strap encircles the neck of the subject. The strap 62 is elastic so that the strap must be elongated or stretched when worn to apply the desired pressure to the IJV. The strap 62 includes an array 65 of stripes 66, 67 of alternating colors. For example, the stripes 66 may be red (to signify a no-go condition) while the stripes 67 may be green (to signify a go condition). The compression collar 60 further includes an overlay 70, shown in FIG. 5, which includes a number of windows 72. The stripes 66, 67 and windows 72 are in like numbers (four in the illustrated embodiment), have the same width and are spaced apart the same dimension. In one specific embodiment the stripes 66, 67 have a width of 2 mm, while the windows 72 have a width of 2 mm and are spaced apart by 2 mm.

As shown in FIG. 6, the overlay 70 is fastened at one end 75 to the strap 62. The opposite end 76 is not fastened to the strap to thereby permit the strap to stretch beneath the overlay. In the embodiments described above the entire strap is elastically elongatable. For the compression indicator at least the portion of the strap in the region of the overlay 70 must be elastic and able to elongate or stretch relative to the overlay. The overlay 70 is affixed to the strap 62 so that all or a substantial portion of the "no-go" stripes 66 are visible in the windows 72 when the strap is in its neutral, unstretched configuration (i.e., before the collar is fitted to the subject), as shown in FIG. 7(*a*). When the collar is fastened around the subject's neck it will stretch and as it stretches the stripes 66, 67 advance relative to the windows 72 of the overlay 70. Thus, as shown in FIG. 7(*b*), a portion of both stripes 66, 67 will be visible through the windows. When the strap is stretched a predetermined amount to apply the desired pressure to the IJV, the "go" stripes 67 will be fully or substantially visible in each window 72, as shown in FIG. 7(*c*). If the strap is stretched too much, the "no-go" stripes 66 will again be visible in the windows. The compression indicator achieved by the stripe array 65 and overlay 70 thus provides a direct visual indicator as to whether the collar is applying the desired amount of pressure to the IJV. The collar may be adjusted so that the "go" stripes 67 are visible by adjusting the engagement elements, or by using a collar having a different starting length. For instance, for the collar 30 of FIG. 2, a different row of snaps 36 may be mated to the snaps 38 to achieve the desired compression.

In the embodiment of FIGS. 4-7, the array 65 includes four sets of parallel stripe pairs 66, 67. However, other visual indicia in any number of pairs may be utilized with appropriate modifications to the windows 72 of the overlay. For instance, array 65 may include visual indicia "GO" and "NOGO" or other words suitable to convey when the collar 60 is applying an appropriate amount of pressure to the IJV. Alternatively, the array may include a single indicia that is visible through a single window in the overlay when the collar is properly adjusted around the neck of the subject. The compression indicator is preferably oriented on the collar at a location that is visible to the subject when looking at a reflective surface. Alternatively, the indicia on the strap 62 may be a tactile indicator that can be felt by the subject's finger through the window(s) in the overlay.

Another aspect of the disclosure encompasses embodiments of a method of increasing the intracranial pressure of an animal or human subject comprising: (i) encircling the neck of an animal or human subject with a collar, wherein said collar has at least one region inwardly directed to contact the neck of an animal or human subject; (ii) positioning the at least one region inwardly directed to contact the neck on a region of the neck overlying a neck vein carrying blood from the intracranial cavity of the subject; and (iii) applying pressure to the neck vein by pressing the at least one region against the neck. In certain embodiments, this compression can be as much as 25 mm Hg without any side effects and without impacting the carotid artery. It is believed that pressures as high as 80 mm Hg can be applied without endangering the jugular vein or carotid artery. For many applications of the method, the pressure applied to the neck vein, or jugular vein, can be 3-15 mm Hg. Applying pressure to the jugular vein can increase ICP up to 30% above the baseline pressure to protect the intracranial cavity from blast-related SLOSH effects without any side effects.

In accordance with one embodiment of the method, a compression collar, such as the collars 10, 10', 30 and 50 are placed low on the neck of the subject and more particularly between the collar bone and the cricoids cartilage or laryngeal prominence. This location is distant from the carotid sinus which is higher on the neck, so application of pressure to the neck will not compress the carotid artery. In the case of a male subject, the cut-out 14 of the strap 12 is positioned directly beneath the laryngeal prominence.

The collar may be pre-sized to the subject so that it automatically delivers the proper amount of compression when the ends of the collar are connected. Moreover, as explained above, the engagement elements (i.e., the latching elements 16, 18, the snaps 36, 38, the hooks 56, 58 or the VELCRO® connection) may be configured to break away or disengage if the pressure exceeds a desired value. This break away feature may also be applied with the pump embodiment of FIG. 2 in which case the bladders 40 can be inflated until the elements become disengaged, at which point the valve 44 may be actuated to bleed off some pressure from the bladders prior to refitting the collar on the subject's neck. In the alternative embodiment of the pump discussed above in which the pump is provided with a pressure gage, the bladders are inflated to the desired pressure indicated on the gage. In most cases, the desired compression provided by the collar may be in the range of 15-20 mm Hg, although higher pressures are well tolerated and may be indicated for certain subjects.

It can be appreciated that the collar is only worn when the subject may be exposed to a concussive event, such as a blast during a military battle or hard contact during a sporting activity. Once exposure to such an event ceases the collar may be removed, although it may be beneficial to leave it in place until the subject is evaluated for concussive related trauma.

Figures 13A, 13B:
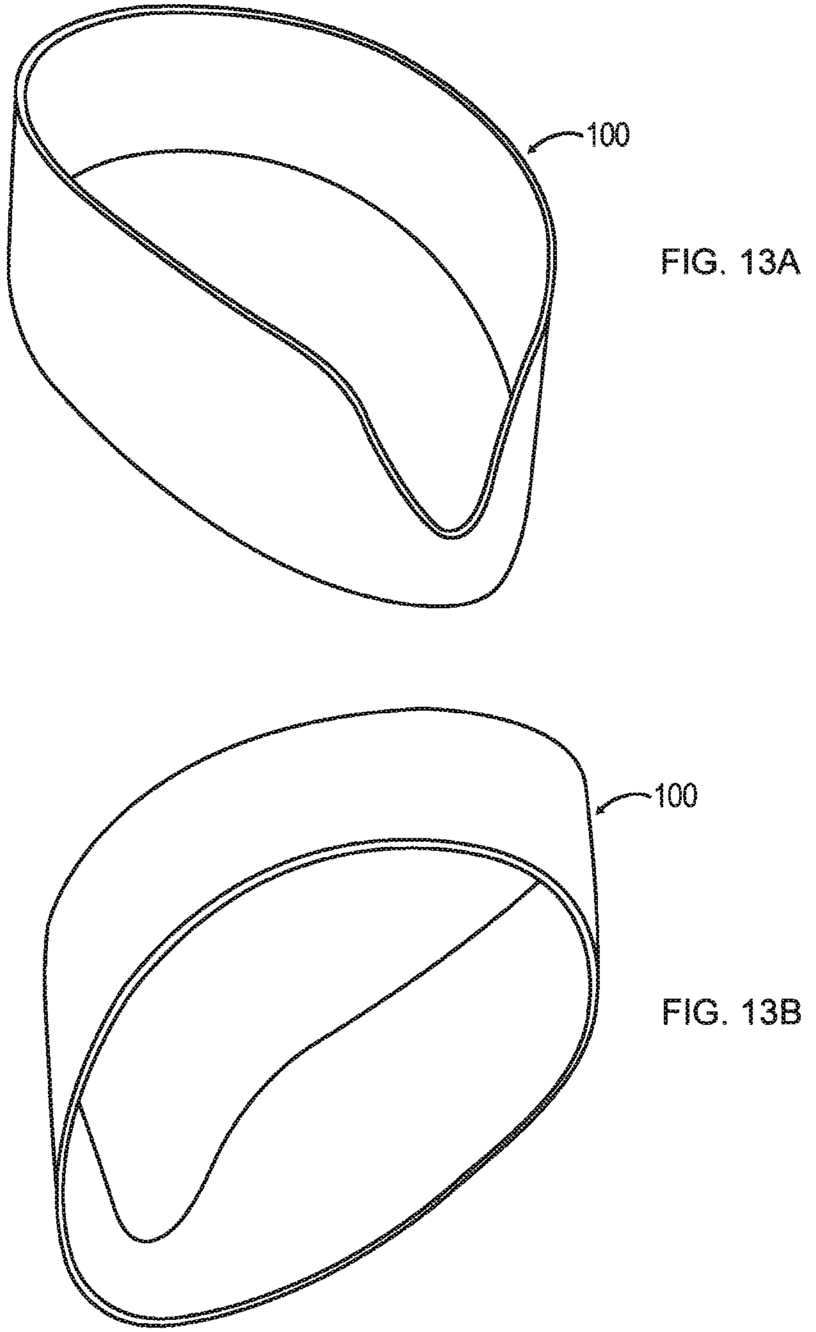
FIGS. 13A-B show an illustration of a circumferential collar made of an elastic material that may be used in various embodiments of the present invention.

Referring now to FIGS. 13A-B, a single unitary circumferential collar 100 is shown. As the unitary circumferential collar 100 has no means of being opened for placement on the wearer, it is intended that such a collar is made of an elastic material that allows the interior dimension of the collar to expand sufficiently to pass over the head of the wearer.

Figures 14A, 14B:
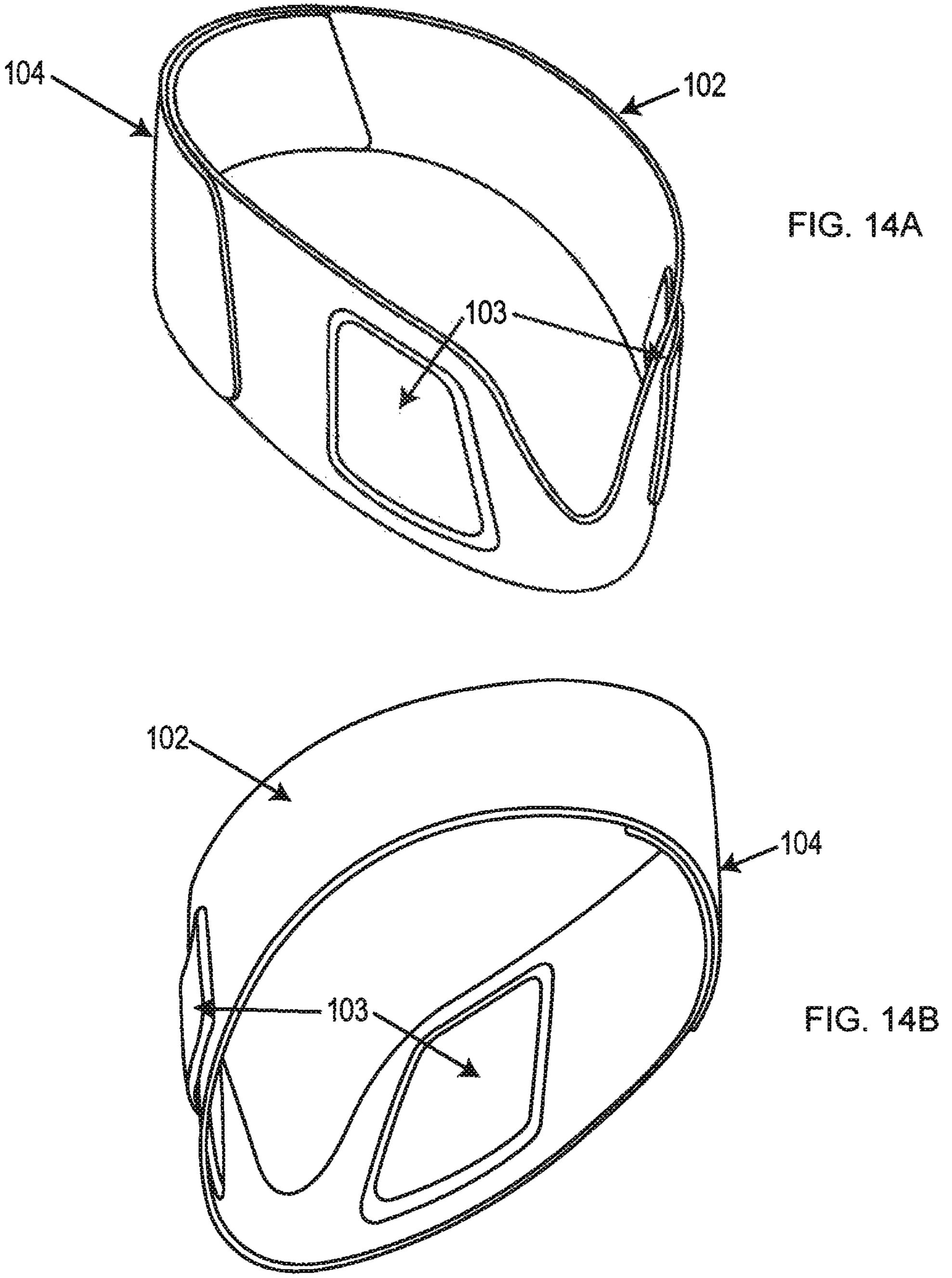
FIGS. 14A-B show an illustration of one embodiment of the present invention comprising a circumferential collar, a fastener for opening and closing, and two protuberances configured to apply pressure to a neck vein of a wearer.

Referring now to FIGS. 14A-B, a circumferential collar type device 102 is shown with pad-like protuberances 103, and an adjustable fastener 104 (such as a VELCRO® type-connection). The adjustable fastener allows for proper fit across a range of neck sizes. The collar type device 102 may be made from elastic or inelastic materials.

Figures 15A, 15B:
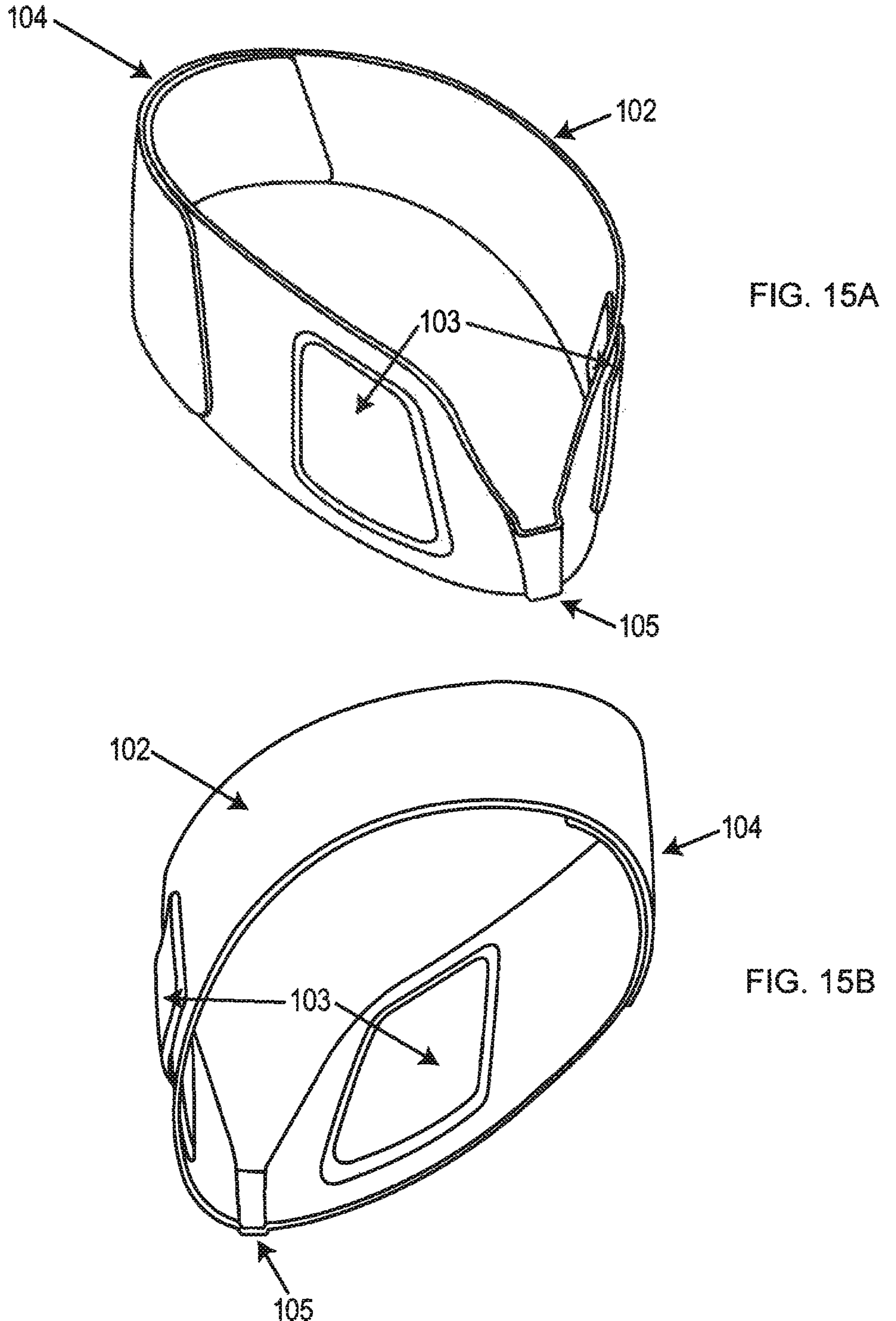
FIGS. 15A-B show an illustration of one embodiment of the present invention comprising a circumferential collar, a fastener for opening and closing, a laryngeal bridge, and two protuberances configured to apply pressure to a neck vein of a wearer.

Referring now to FIGS. 15A-B, a similar circumferential collar type device 102 is shown with pad-like protuberances 103, and an adjustable fastener 104 (such as a VELCRO® type-connection). The adjustable fastener allows for proper fit across a range of neck sizes. The collar type device 102 may be made from elastic or inelastic materials, and further comprises a semi-rigid or rigid laryngeal bridge 105.

Figures 16A, 16B:
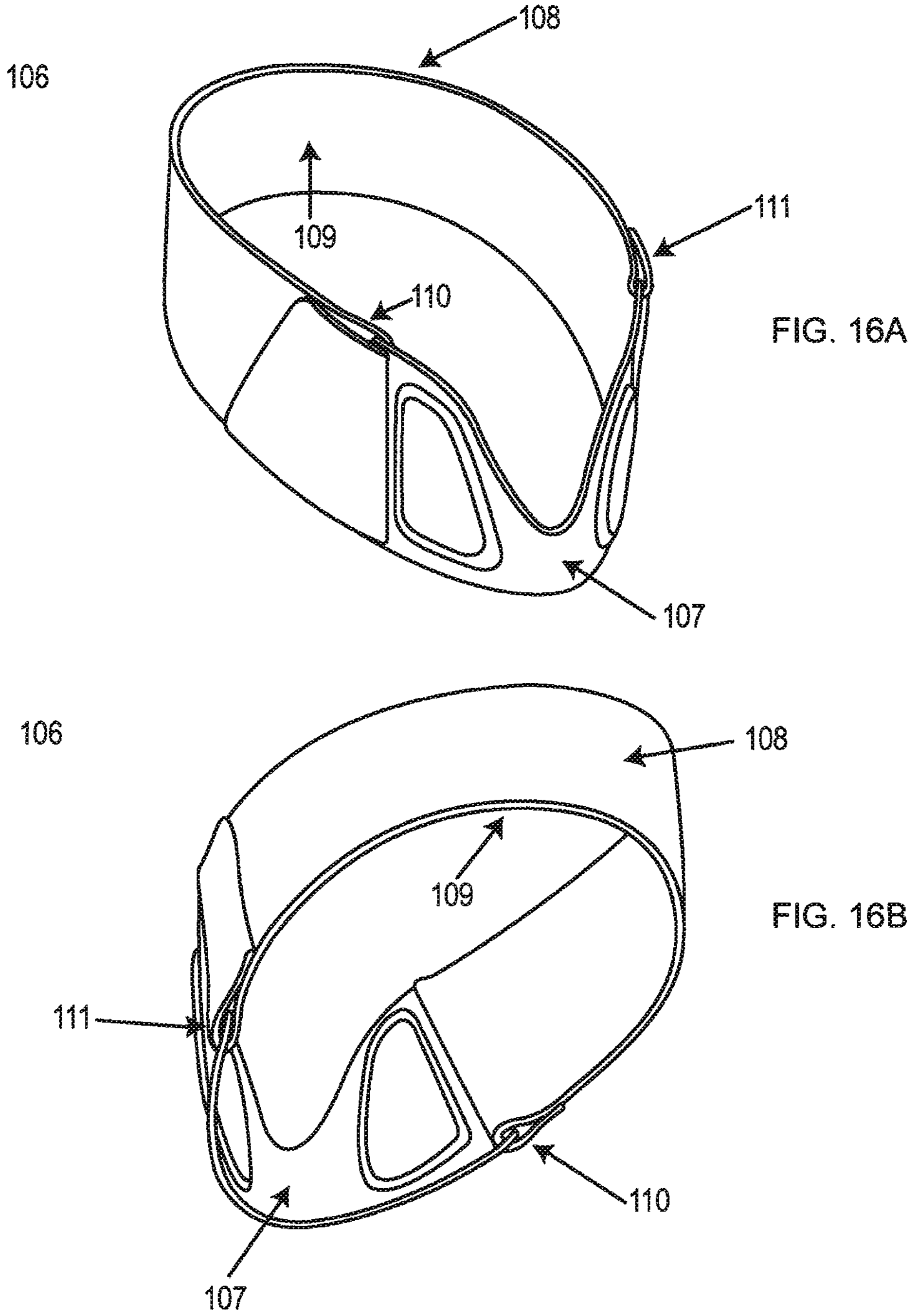
FIGS. 16A-B show an illustration of one embodiment of the present invention comprising a circumferential collar comprising two pieces: a first piece (i.e., front section) comprising and two protuberances each configured to apply pressure to a neck vein of a wearer, and second piece (i.e., back section) comprising a fabric collar configured to be removably attached to either end to the first piece.

Referring now to FIGS. 16A-B, a circumferential collar type device 106 a first piece (i.e., front section 107) and second piece (i.e., back section 108). The front section 107 contains two protuberances 103 each configured to apply pressure to a neck vein of a wearer. The back section 108 comprises a fabric collar section 109 configured to be removably attached (such as by VELCRO® type-connections) at either end to corresponding ends 110 and 111 of the front section 107. It is intended that the back section 108 may be made from elastic or inelastic materials. It is further intended that the front section 107 may further comprise a semi-rigid or rigid laryngeal bridge (not shown).

Figures 17A, 17B:
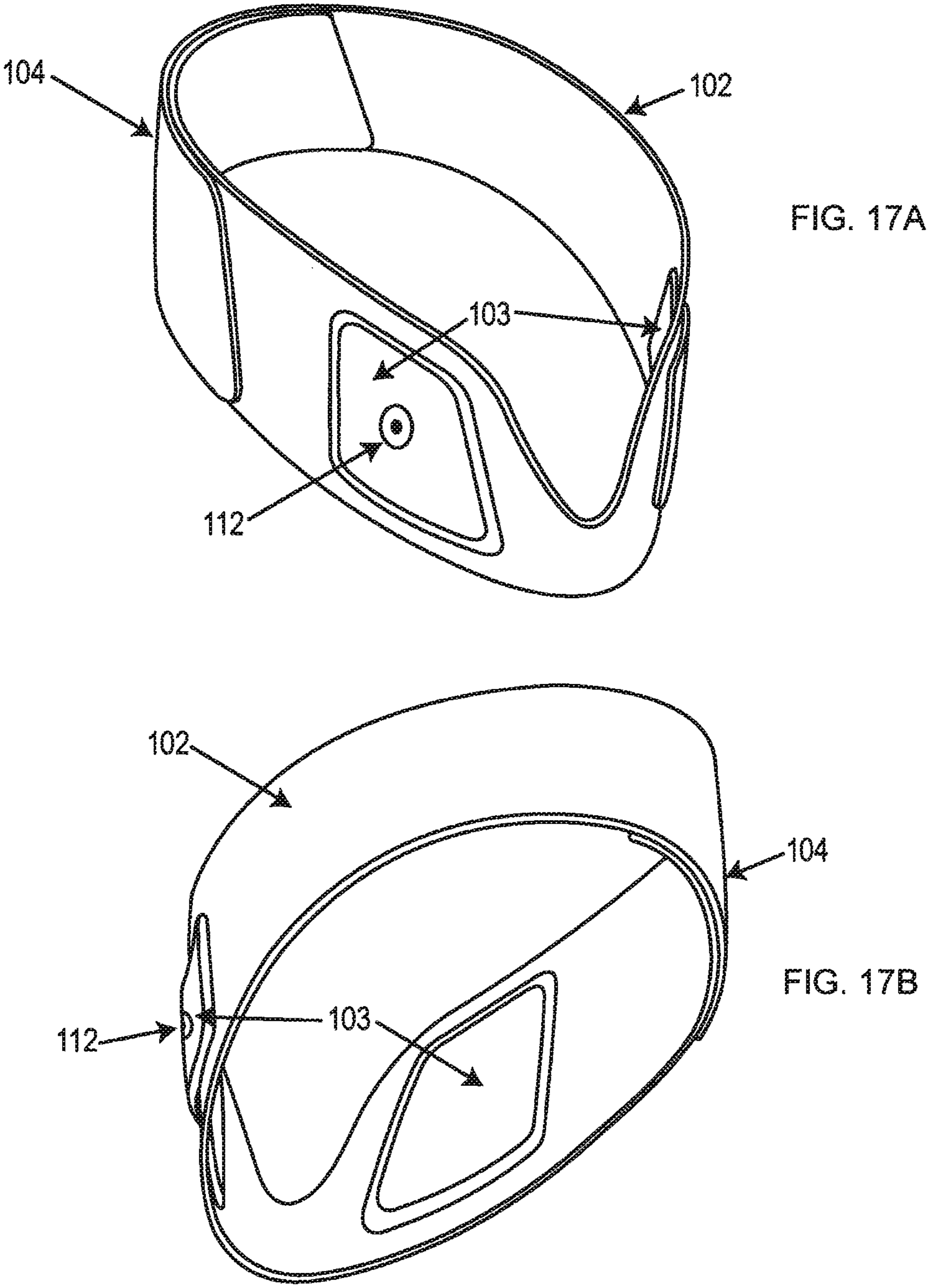
FIGS. 17A-B show an illustration of one embodiment of the present invention comprising a circumferential collar, a fastener for opening and closing, and two protuberances each (comprising a bladder and a pressure release valve) configured to apply pressure to a neck vein of a wearer.

Referring now to FIGS. 17A-B a circumferential collar type device 102 is shown with pad-like protuberances 103, and an adjustable fastener 104 (such as a VELCRO® type-connection). The adjustable fastener allows for proper fit across a range of neck sizes. The collar type device 102 may be made from elastic or inelastic materials. In this embodiment, the two pad-like protuberances 103 each comprise a bladder (not shown) and a pressure release valve 112 configured to apply pressure to a neck vein of a wearer.

Figure 18:
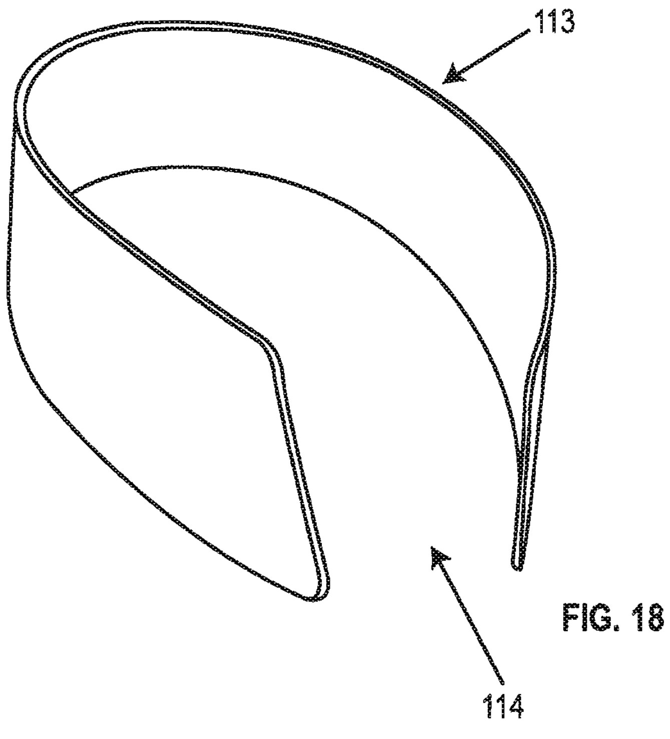
FIG. 18 shows an illustration of a semi-circumferential collar with a front opening that may be used in various embodiments of the present invention.

Referring now to FIG. 18, a semi-circumferential collar 113 with a front opening is shown. As the semi-circumferential collar 113 is open in the front 114, it is intended that the collar 113 comprises a rigid or semi-rigid material, and that the collar 113 is worn by sliding the collar onto the neck of the wearer from the back to the front.

Figure 19:
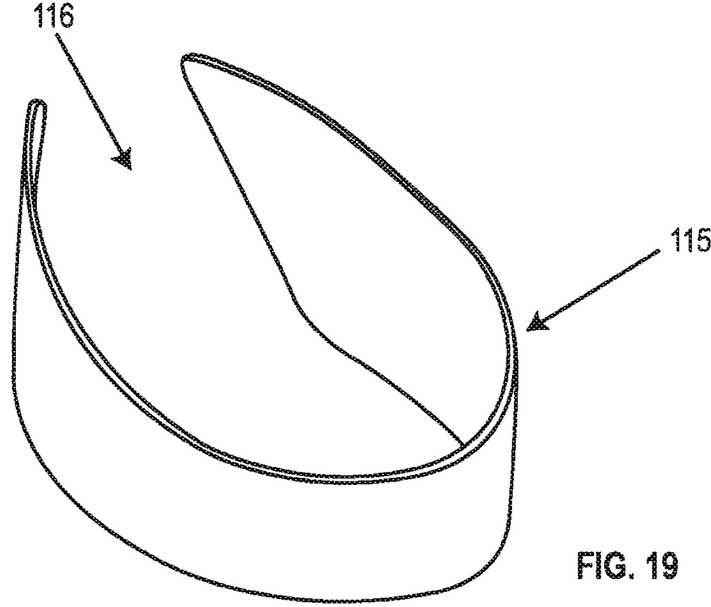
FIG. 19 shows an illustration of a semi-circumferential collar with a back opening that may be used in various embodiments of the present invention.

Referring now to FIG. 19, a semi-circumferential collar 115 with a back opening 116 is shown. As the semi-circumferential collar 115 is open in the back, it is intended that the collar 115 comprises a rigid or semi-rigid material, and that the collar 115 is worn by sliding the collar onto the neck of the wearer from the front to the back.

Figure 20A:
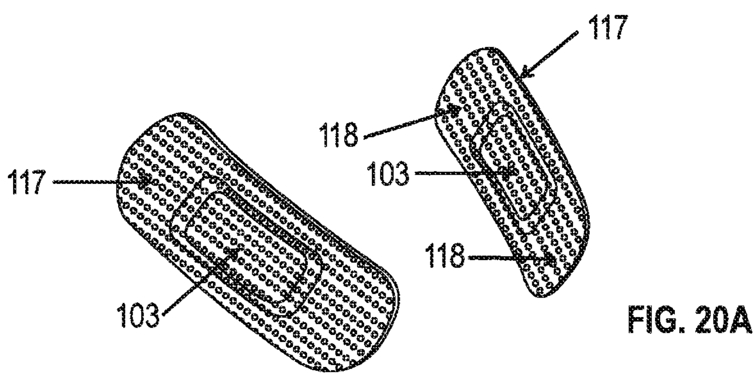
FIGS. 20A-B show illustrations of exemplary embodiments of the present invention that apply pressure on appropriate positions on the neck without the use of a circumferential collar. These embodiments are typically worn as pairs, with a device worn one either side of the neck.
Figure 20B:
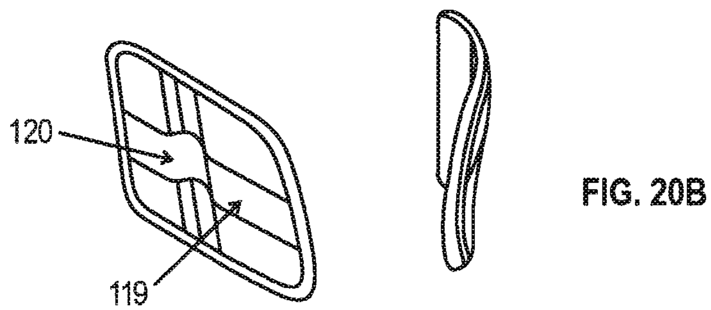
Figure 20C:
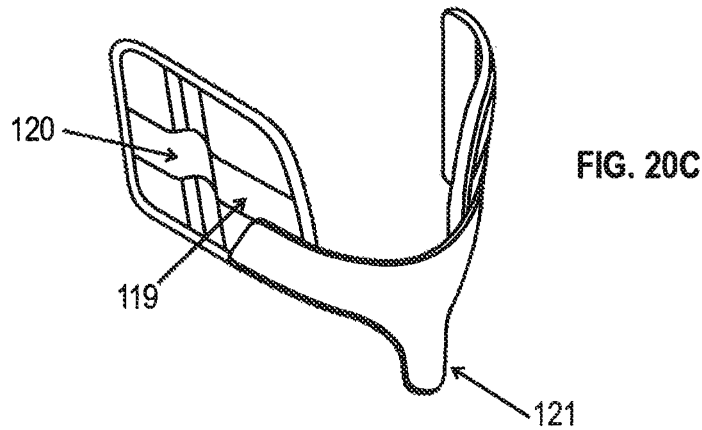
FIG. 20C is an illustration of a pair of these devices connected with a removable tether which is sized to insure correct placement of the devices on the subject's neck such that the protuberances overlie the neck veins sought to be partially or completely occluded.

Referring now to FIGS. 20A-B, exemplary embodiments that apply pressure on appropriate positions on the neck without the use of a circumferential collar are shown. These embodiments are typically worn as pairs, with a device worn on either side of the neck. FIG. 20A shows that each device comprises a pad-type protuberance 103 covered by a flexible material 117 that extends beyond the area defined by the protuberance. If these devices are used without a collar, it is intended that at least a portion of the inwardly directed surface 118 of the material extending beyond the area defined by the protuberance is coated with an appropriate adhesive. An inwardly directed surface of the protuberance 103 may also be coated with an appropriate adhesive. In these embodiments, the flexible material 118 may be elastic or inelastic. FIG. 20B shows a similar embodiment that differs by employing a resilient arcuate band 119 having a general C, V, or U-shape to form a protuberance 120. As discussed above, the band may be formed of a resilient spring-like material whereby the C, V, or U-shaped band is straightened as the device is applied. After application of the device, spring tension causes compression of the band, resulting in the mid-point or bend-point of the band to extend toward and apply pressure to the neck. As shown in FIG. 20C, optionally, the pairs of devices are attached via a removable tether 121. The tether is used to facilitate the application of the device pairs to the neck of the subject and is sized appropriately to insure proper spacing of the devices such that the protuberances 103 or 120 are correctly positioned to overlie the neck veins sought to be occluded or partially occluded. The tether 121 is removed once the devices are appropriately placed and adhered to the subject's neck. The tether 121 may be attached to the devices using any appropriate reversible fastening system including snaps, hooks, or a thinning or scoring of tether material to facilitate detachment. In one embodiment, the devices and tether 121 are reusable such that, after an initial use, the devices may be reattached to the tether 121 suitable for a subsequent application.

Figure 21:
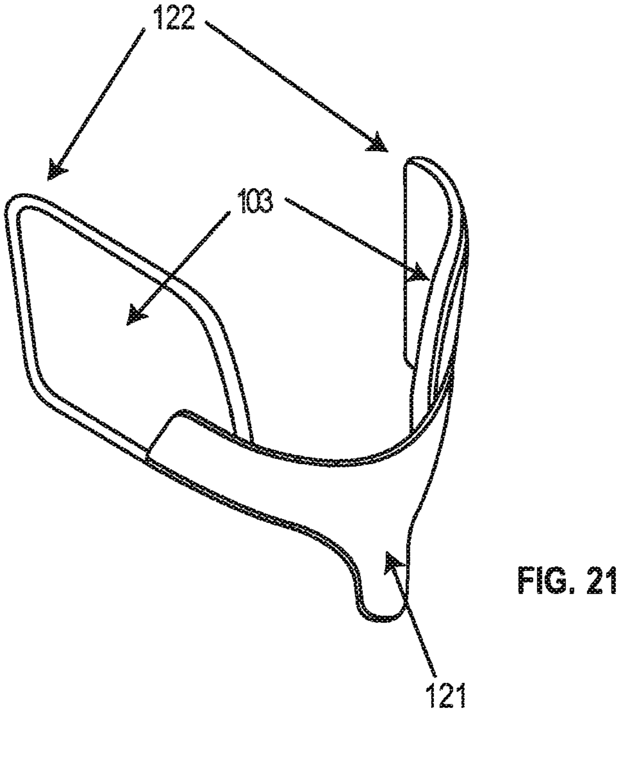
FIG. 21 is an illustration of another embodiment of the present invention that applies pressure on appropriate positions on the neck without the use of a circumferential collar. The device shown in FIG. 21 is similar to those of FIGS. 20A-B, but further includes a removable tether of the appropriate length between a pair of devices that acts as an alignment and spacing guide for application to the neck.

FIG. 21 is an illustration of another embodiment of the present invention that applies pressure on appropriate positions on the neck without the use of a circumferential collar. The device shown in FIG. 21 is similar to those of FIGS. 20A-C, and illustrates other configurations of a removable tether 121 of the appropriate length between a pair of devices 122. Each device comprises a protuberance 103 and it is intended that one device will be applied to either side of the neck. The removable tether 121 aids in alignment and spacing during application of the devices 122 to the neck.

Figure 22:
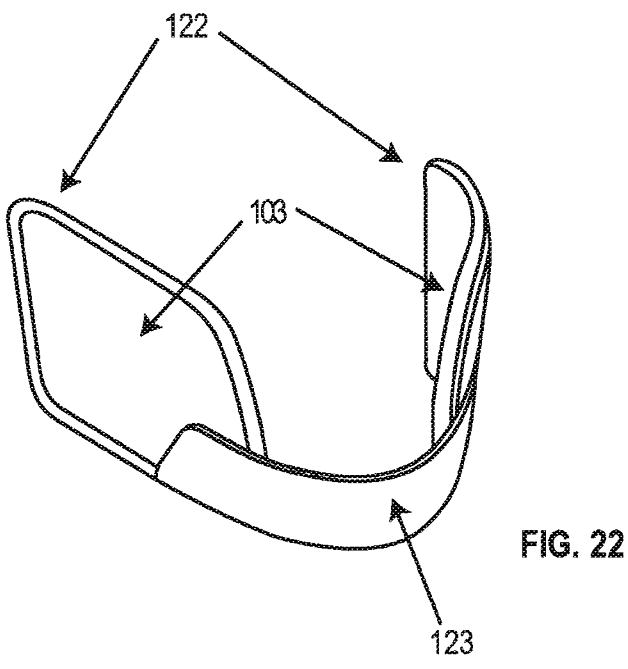
FIG. 22 is an illustration of another embodiment of the present invention that applies pressure on appropriate positions on the neck without the use of a circumferential collar. In this embodiment, the device comprises a U-shaped resilient band with a protuberance disposed on one or both ends.

FIG. 22 is an illustration of another embodiment of the present invention that applies pressure on appropriate positions on the neck without the use of a circumferential collar. In this embodiment, the device comprises a U-shaped resilient band 123 with a protuberance 103 disposed at or near each end. In some embodiments, the protuberances 103 may be integral to the resilient band 123. The embodiment shown in FIG. 22 is of an alternate design, where the protuberances 103 are integral into devices 122, which are attached at either end of the resilient band 123. The U-shaped resilient band 123 is of the appropriate size and shape, and is appropriately resistant to bending, such that when the band is bent open, the protuberances 103 can be placed on the neck the appropriate locations and the band exerts sufficient compressive force so as to reduce venous blood flow from the head.

Figure 23:
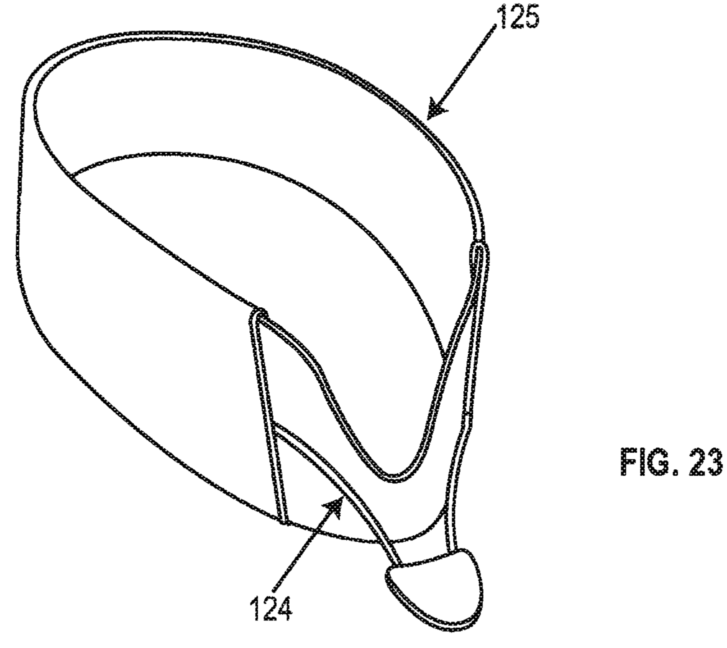
FIG. 23 is an illustration of a circumferential collar type device of the present invention comprising a pull-away cable-tie type ratcheting fit adjustment system, wherein the pull-away cable-tie is configured to release from the collar when pulled at or above a specific pressure.

FIG. 23 is an illustration of a circumferential collar type device of the present invention comprising a pull-away cable-tie type ratcheting fit adjustment system. In the shown device, the pull-away cable-tie 124 is configured to release from the collar 125 when pulled at or above a specific pressure, thus ensuring that the collar 125 is not over tightened.

Figure 24:
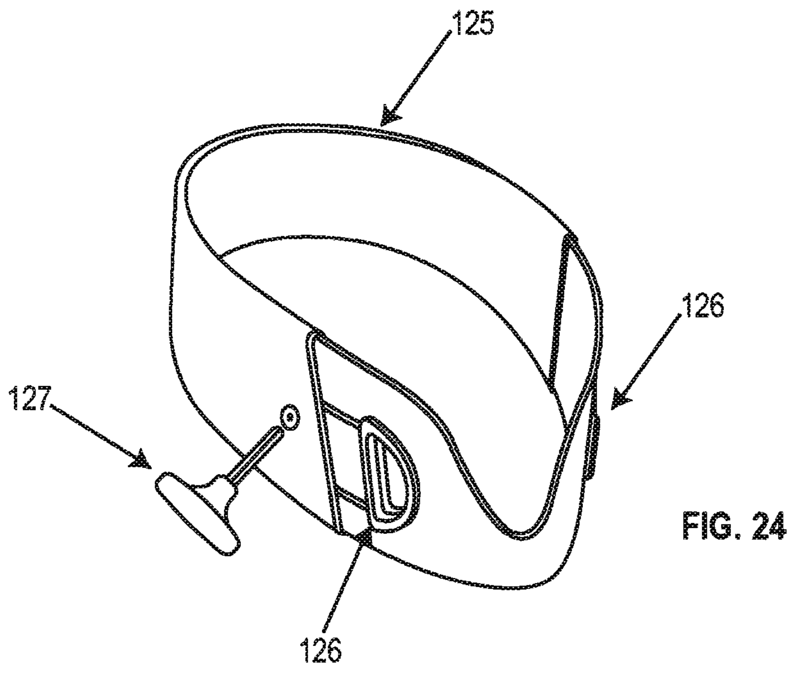
FIG. 24 is an illustration of a circumferential collar type device of the present invention comprising a rotating ratchet fit adjustment system and an external adjustment tool.

FIG. 24 is an illustration of a circumferential collar type device of the present invention comprising a rotating ratchet fit adjustment system and an external adjustment tool. In this embodiment, the fit of collar 125 is adjusted with an integral cable system 126. An external tool 127 is used to shorten or lengthen the integral cable 126, thereby allowing for fine control of fit adjustment.

Figures 25A, 25B:
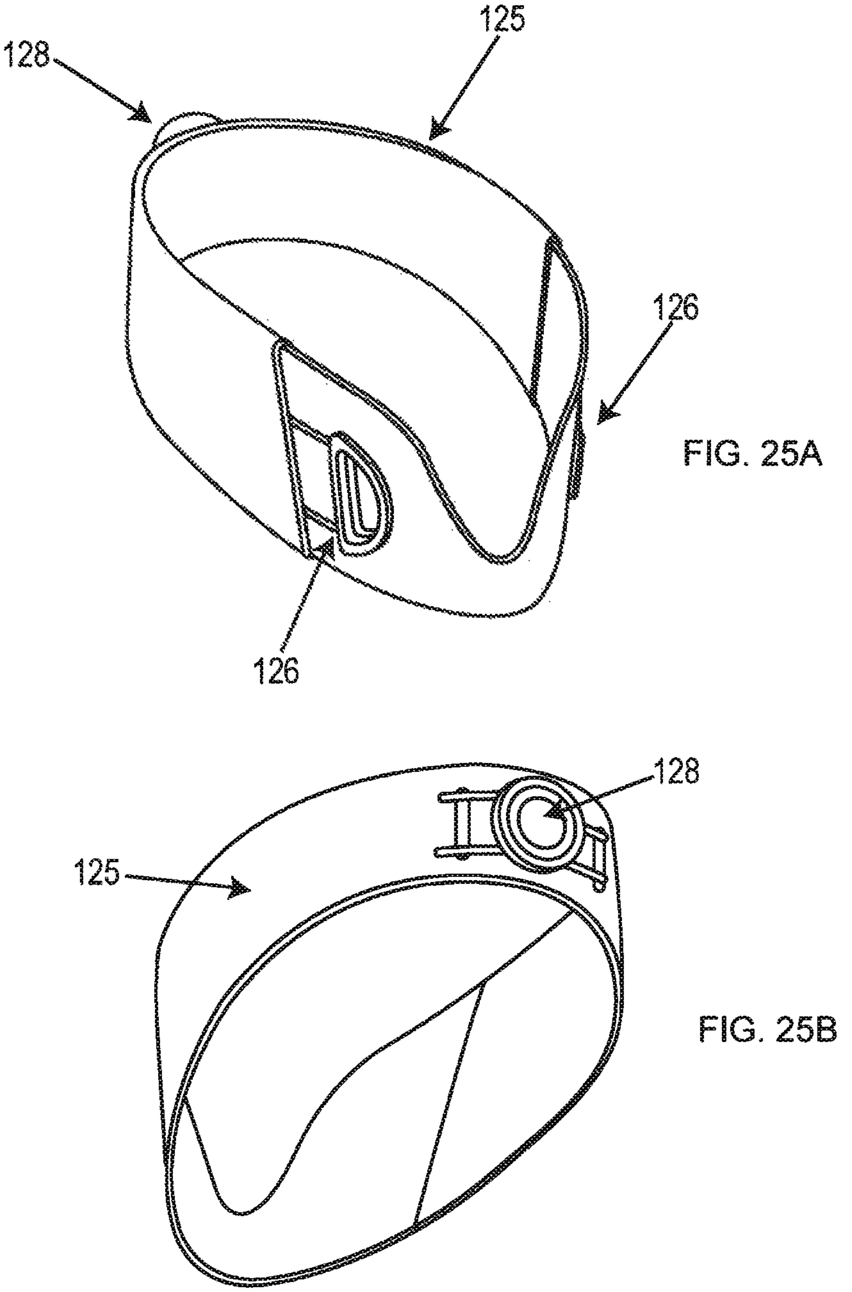
FIG. 25 is an illustration of a circumferential collar type device of the present invention comprising a rotating ratchet fit adjustment system with an integrated adjustment dial.

FIGS. 25A-B are illustrations of a circumferential collar type device of the present invention comprising a rotating ratchet fit adjustment system with an integrated adjustment dial. Similar to the embodiment described above, the fit of collar 125 is adjusted with an integral cable system 126. In this embodiment, however, an internal ratcheting dial 128 is used to shorten or lengthen the integral cable 126, thereby allowing for fine control of fit adjustment.

Figures 26A, 26B, 26C:
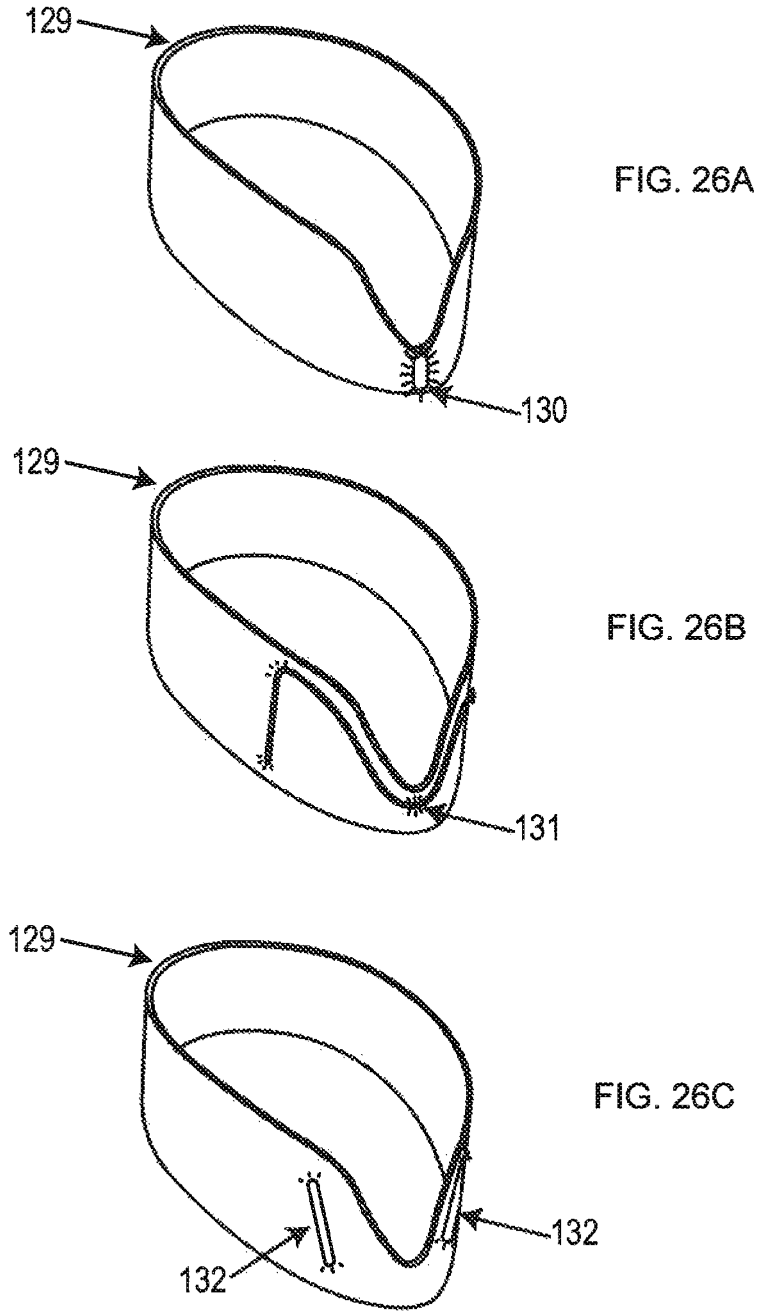
FIG. 26 is an illustration of circumferential collar type device of the present invention comprising one or more discernible graphic or tactile reference points on an exterior surface of the device to assist placement and/or alignment on the wearer.

FIGS. 26A-C are illustrations of circumferential collar type device of the present invention comprising one or more discernible graphic or tactile reference points on an exterior surface of the device to assist placement and/or alignment on the wearer. As described above, the graphic or tactile reference points may be of any suitable design and/or material. In the exemplary embodiments shown in FIGS. 26A-C, the graphic or tactile reference points may be placed so as to indicate the mid-point of the device for alignment at the center of the front of the neck (e.g., shown with fabric patch 130), indicate the location of the protuberances (e.g., shown with fabric patches 132), or both (shown with fabric trace 131).

FIG. 27 is an illustration of another embodiment of the present invention wherein the device 135 further comprises a sensor (not numbered) configured to detect pulse, blood pressure, or other indicia of proper placement and pressure of a protuberance above a neck vein, and means to transmit a signal from the sensor to an external device 136.

FIGS. 28A-C are illustrations of another embodiment of the present system wherein one or more protuberances 103 are integral with a garment 137. The protuberances 103 may be incorporated into a portion of a garment 138 that covers a portion of the neck of a wearer. Preferably, the portion of the garment 138 covering the portion of the neck of the wearer comprises an elastic material such that the collar of the garment exerts sufficient pressure on the protuberances 103 so as to reduce venous blood flow from the head. While not intending to be limiting, it is envisioned that garments designed for various specialized purposes, such as components of military uniforms or sporting apparel, may be constructed according to these embodiments. Optionally, the garment 137 is open at the laryngeal prominence and the upper portion of the garment is rigid or semi-rigid to exert pressure on the neck veins via the protuberances 103. Alternatively, the garment 137 covers the laryngeal prominence (e.g., as a turtleneck), wherein the upper portion of the garment is rigid or semi-rigid to exert pressure on the neck veins via the protuberances 103 or contains a closure device that, when closed, is capable of exerting pressure on the neck veins via the protuberances 103.

Figure 29:
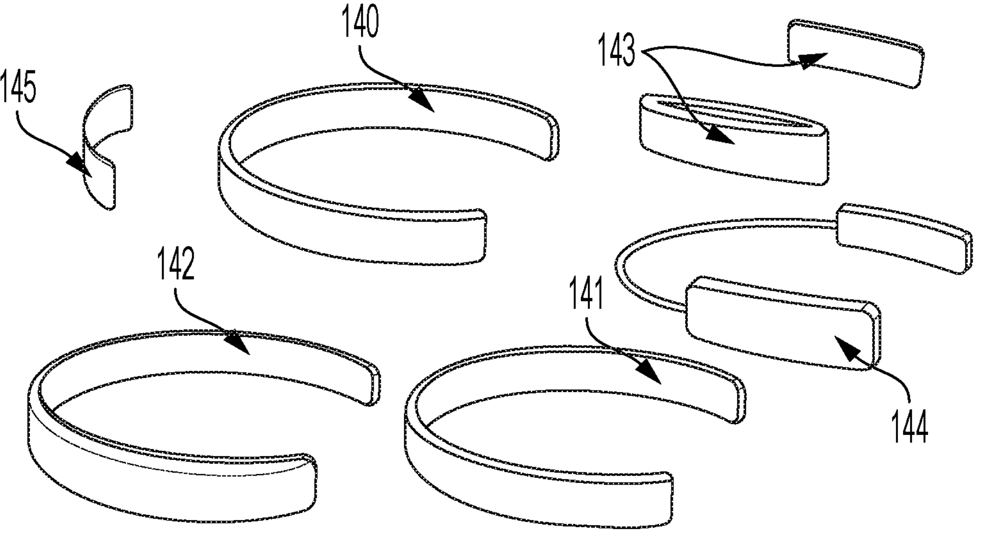
FIG. 29 is an illustration of embodiment of the present system components.

FIG. 29 is an illustration of another aspect of the present system which is comprised of a circumferential or semi-circumferential collar 140. In one embodiment the collar 140 is a solid band. In one embodiment of the present system, the collar is comprised of an inner housing 141 and outer housing 142, internal band. In either embodiment, pads 143 may be removeably attached to the ends of the collar 140 whereby the collar is sized such that the pads 143 are spaced to be disposed above the one or more neck veins of the subject when the collar 140 is worn by on the neck of the subject. In one embodiment the collar 140 is configured to apply pressure within a range of 5 mmHg to 80 mmHg on the one or more neck veins. In one embodiment the collar 140 is configured to apply pressure within a range of 5 mmHg to 25 mmHg on the one or more neck veins. In one embodiment, the one or more neck veins comprise the internal jugular vein and the external jugular vein. In one embodiment, the system comprises a plurality of pairs of pads 143. For example, the system may comprise a collar 140 and three pairs of pads wherein each pair of pads is differently sized or shaped in order to provide a more customized fit to the user. Differences among the pairs of pads may include the shape or dimension of the protuberance. For example, each pair of pads may comprise protuberances having different heights such that greater heights to apply increasing pressures to the neck veins and/or to account for individuals having a greater or lesser amount of subcutaneous adipose tissue overlying the neck veins. Alternatively or in addition, each pair of pads may have a different shape or differently-shaped protuberances, particularly in the longitudinal direction (i.e., directed around the circumference of the neck) in order to account for anatomical variations in the location of the neck veins of individuals having necks of similar circumference. The removable pads may be designed to attach to the collar by any appropriate mechanism which insures that the pads remain in place. For example, the ends of the collar may be configured as a tab and the pads may contain a slot which accepts the collar tab. Alternatively, the collar may contain a groove on the anterior-facing surface which accepts and holds the pad in place.

In an alternative embodiment the pads 143, each pad comprises an inflatable bladder 144. In one embodiment, each pad of pads 143 is in fluid communication with the other pad of the pair. In one embodiment, a tube 145 allows fluid communication between each of the pair of pads 143. In one embodiment, the system further comprises a pump element in fluid communication with a bladder 144, whereby the fill level of the bladder 144 can be adjusted by the subject. In one embodiment the collar 140 is comprised of a band which provides the basic force mechanism, the inner 141 and outer 142 housing is provided for comfort of the subject. The system can also include optional electronics 146 which can measure various conditions of the system such as the pressure on the subject or the pressure in the bladder 144.

In one embodiment for all aspects of the system the collar 140 is encased in a cover. In one embodiment the cover may be open at both ends. In one embodiment the cover may be closed at one end and open at the other end. In one embodiment the cover may have a closing mechanism at one or both ends to include a hook and pile or similar system to close one or both ends of the cover. The cover can also be completed closed. The cover can also have openings around the protuberances. The cover can be manufactured from one or more of textiles, films (wovens, non-wovens and nettings), foams and rubber (synthetics and natural), polychloroprene (e.g. NEOPRENE®), elastane and other polyurethane-polyurea copolymerss (e.g. SPANDEX®, LYCRA®), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. The cover can also be manufactured from a moisture wicking fabric made from a polyester blend. The use of a non-chaffing fabric for the cover is also a consideration. The cover can be manufactured in a variety of colors and have a multitude of designs or logos imprinted on the cover.

Figure 30:
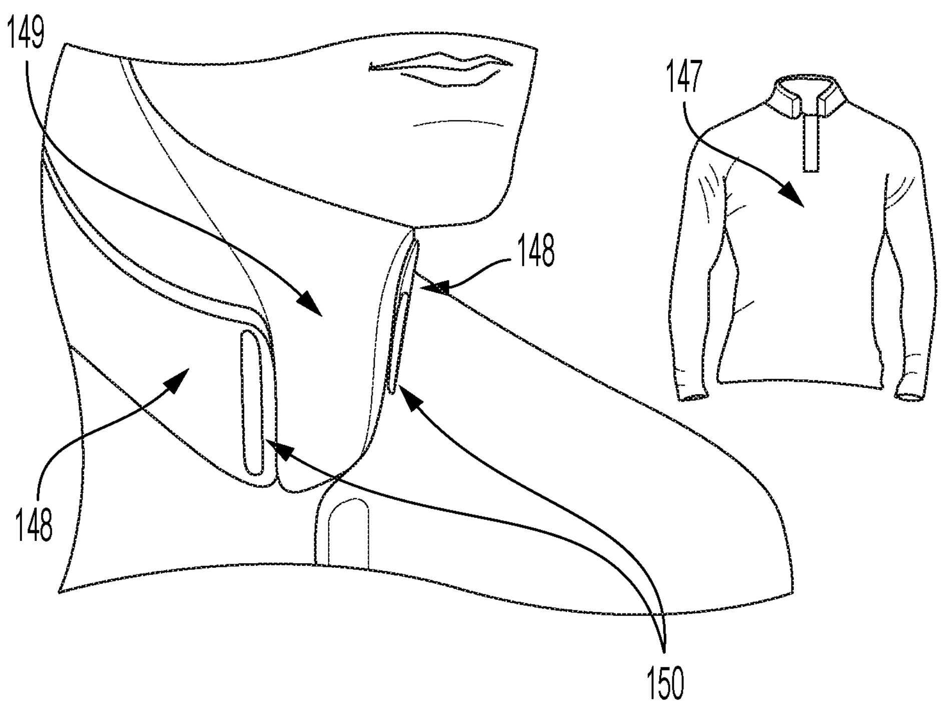
FIG. 30 is an illustration of embodiment of the present system incorporated into a wearable garment.
Figure 30:
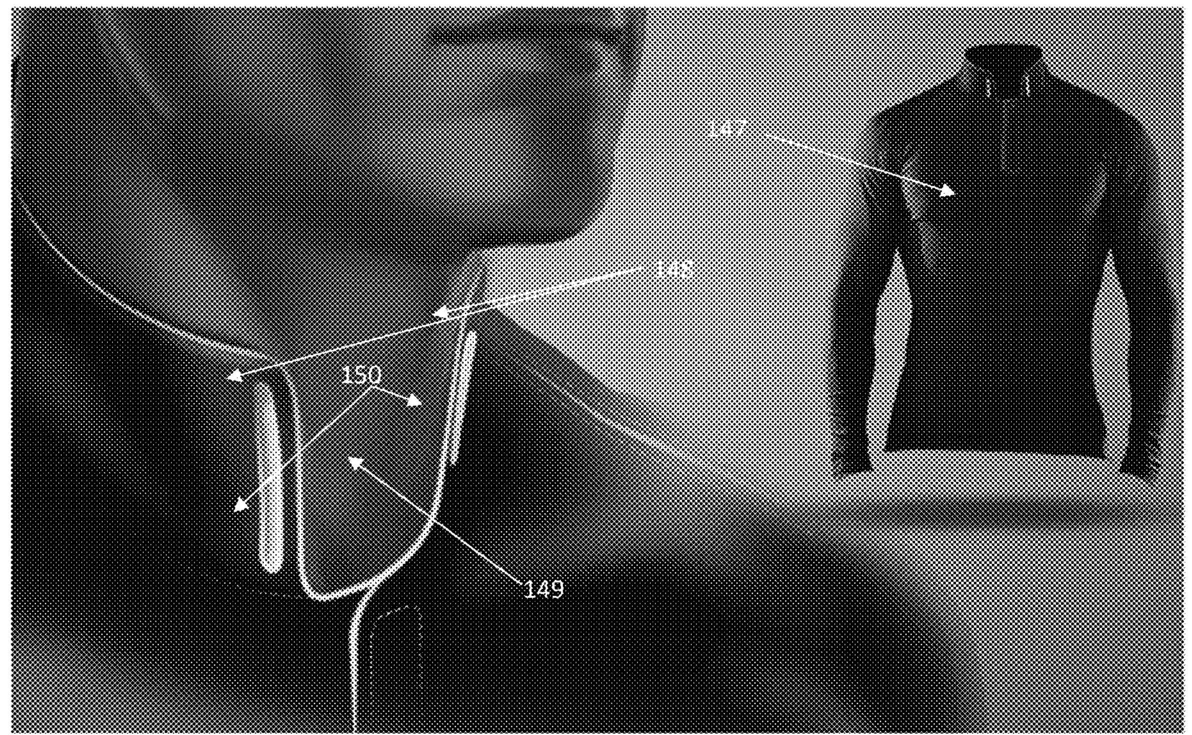

FIG. 30 is an illustration of another aspect of the present system which is comprised of a garment 147, which contains a semi-circumferential flap 148 which is open at the laryngeal prominence 149, wherein the flap contains a sleeve 150 which in one embodiment is sewn into the fabric of the garment 147 and is open at both ends of the laryngeal prominence 149. In one embodiment, the flap 148 may be attached separately to the top of the garment 147 at the opening for the neck. The system also includes a circumferential or a semi-circumferential collar to be worn on the neck of a subject which is designed to fit at least partially within the sleeve 150 of the garment 147. In this way various sized garments 147 can accommodate various neck sizes using variable sized collars. The garment 147 can be comprised of various elastic fabrics. Elastic materials can be any material which when stretched will attempt to return to the natural state. Exemplary materials may include one or more of textiles, films (wovens, non-wovens and nettings), foams and rubber (synthetics and natural), polychloroprene (e.g. NEOPRENE®), elastane and other polyurethane-polyurea copolymerss (e.g. SPANDEX®, LYCRA®), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. There are also a number of elastic materials which are breathable or moisture wicking which may be preferable during extended wearing periods or wearing during periods of exercise. As indicated above, elastic materials may confer the benefit of increased comfort for the wearer by providing sufficient compressive pressure, yet remaining flexible to accommodate a full range of motion and/or muscle flex in the wearer.

Figure 31:
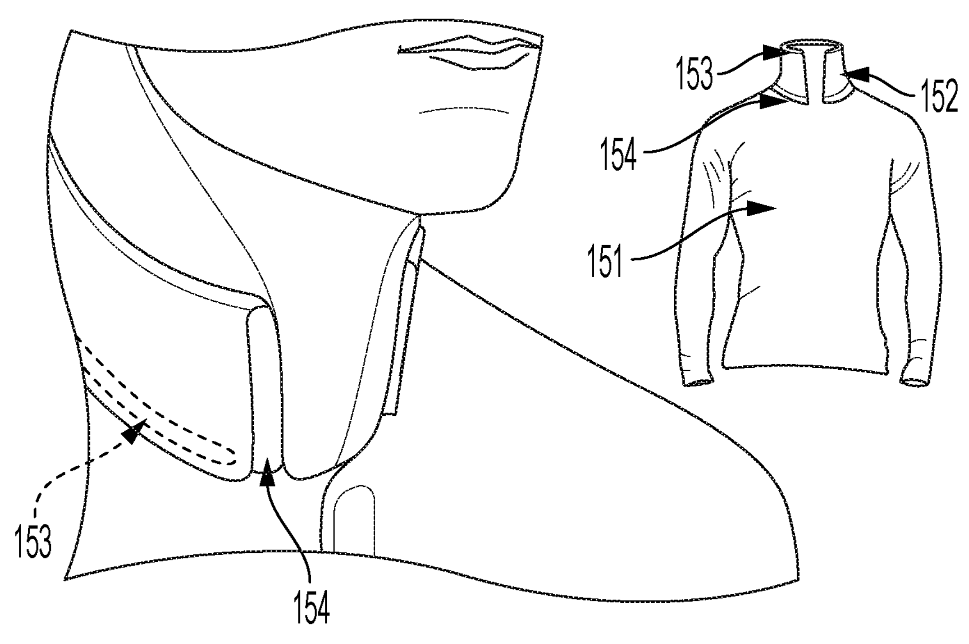
FIG. 31 is an illustration of another embodiment of the present system incorporated into a wearable garment.

FIG. 31 is an illustration of another embodiment of the present system which is comprised of a garment 151, which comprises a semi-circumferential flap 152. In one embodiment, the semi-circumferential flap 152 is further comprised of an upper attachment means 153 and a lower attachment means 154. The attachment means may be comprised of a hook and pile system, magnetic bands or other means used to hold connect the upper and lower portions of the flap 152. The flap 152 can be folded down with the upper attachment means 153 and lower attachment means 154 in approximate alignment.

Figure 32:
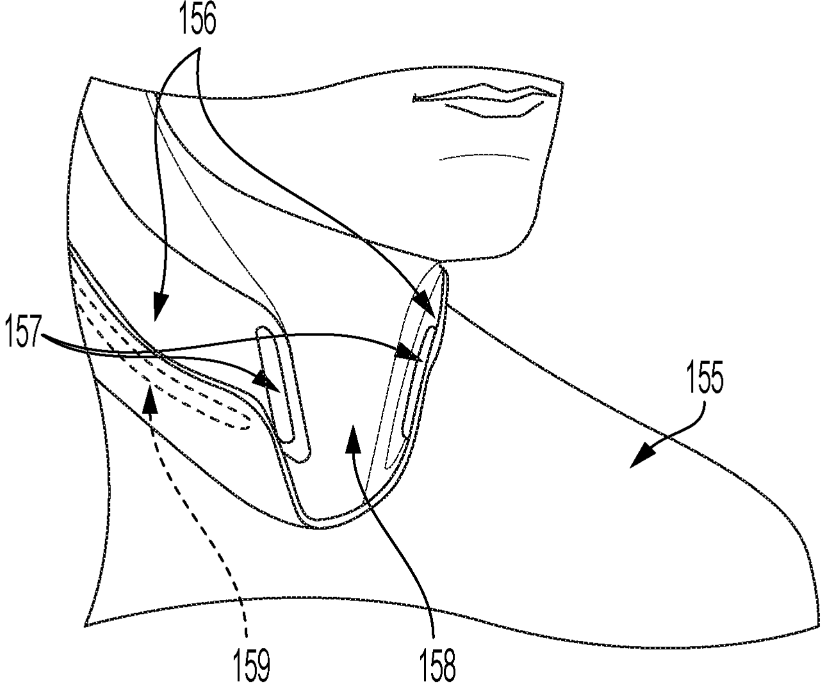
FIG. 32 is an illustration of another embodiment of the present system incorporated into a wearable garment.

FIG. 32 is an illustration of another embodiment of the present system which comprised of a garment 155 and a semi-circumferential collar 156 wherein the collar 156 comprises a plurality of protuberances 157, and wherein both the garment 155 and collar 156 is open at the laryngeal prominence 158. In one embodiment the collar 156 is affixed to the upper portion of the garment 155 by an appropriate fastening system including, for example, a hook-and-pile system (VELCRO®), adhesive, etc. such that the collar 156 is removeably affixed to the garment 155. Optionally, the collar 156 may be fully circumferential (i.e., not open at the laryngeal prominence 158) and the garment 155 may be either open or closed at the laryngeal prominence 158.

Figures 33, 34:
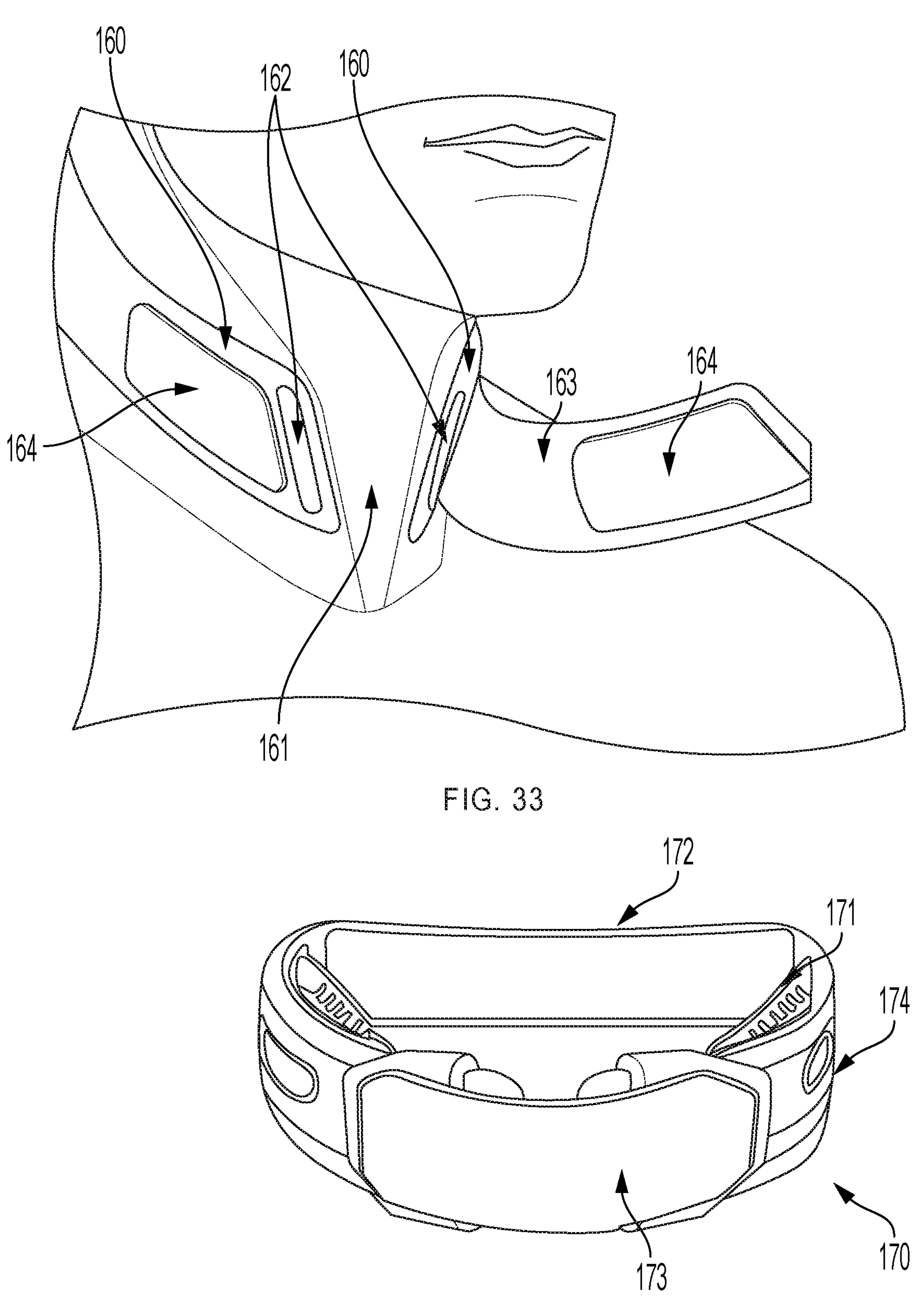
FIG. 33 is an illustration of another embodiment of the collar used in an embodiment of the present system.
FIG. 34 is an illustration of another embodiment of the collar in which the collar has a rigid or semi-rigid front member which, inter alia, provides protection to the laryngeal prominence and/or throat region of the wearer.

FIG. 33 is an illustration of another aspect of the present system which may be used in any of the foregoing systems or as a stand-alone device. In this system the functional aspect of the collar 160 is semi-circumferential, comprising a plurality of protuberances 162, and open at the laryngeal prominence 161, and further comprises a flexible or rigid strap 163 which is affixed to one side of the collar 160. The strap 163 can be connected across the laryngeal prominence 161 and removeably attached to the opposite side of the collar 160 by a hook and pile type or other quick-release connection means 164. The strap 163 may be used to secure the collar 160 about the neck of the subject either as a stand-alone device or in conjunction with a garment system described herein. In one embodiment, the strap 163, provides the force which causes the collar 160 to generate pressure on one or more of the neck veins. In one embodiment for this aspect of the system, the system further comprises a cover which encases the collar 140 as previously disclosed.

FIG. 34 is an illustration of another aspect of the invention which comprises a collar, as described above, with a rigid bridge across the laryngeal prominence and throat which may be used, for example, in sports and other activities including ice hockey, in which throat protection is desired. In the illustrated embodiment, the collar 170 is fully circumferential and comprises protuberances 171, illustrated as pads or thickenings in the region adapted to overly the neck veins, rigid or semi-rigid side members 174, a back member 172, which is optionally made of an elastic material and is adapted to contact the back of the neck, and a rigid front member 173 which is adapted to protect the laryngeal prominence and/or throat of the subject. In accordance with the other aspects and principles described herein, the protuberances 171 may be inflatable or fixed, may comprise a rigid, semi-rigid, or memory foam material, and may be configured as a stud, pad, or other type of protuberance. The back member 172 is illustrated as a elastic material which facilitates application of the collar 170 by stretching over the subject's head and/or applies force to the side members 174, thereby applying neck vein pressure via the protuberances 171. Alternatively, the back member 172 may have a detachable closure mechanism such as a hook-and-pile system, buckle, snap, latch, hinge and/or other closure and/or fitting device which facilitates collar 170 application by sliding around the neck of the subject from the front when in the open configuration followed by closure and fitting using the closure mechanism. In another embodiment, the back member 172 comprises a ratcheting tensioning device to adjust the circumference of the collar 170 when in place on the neck. In another embodiment, the back member 172 is rigid or semi-rigid and the rigid front member 173 comprises a hinge and fastening mechanism (e.g., snap) such that the collar 170 is adapted to be applied from the back of the neck toward the front. In another embodiment, the rigid front member 173 is fully detachable such that the collar 170 may be worn as a semi-circumferential configuration when the additional protection of the laryngeal prominence and/or throat of the subject is not desired. In another embodiment, a fit adjustment system (e.g., a ratcheting tensioning device) is located on the rigid front member 173 instead of, or in addition to, a fit adjustment system on the back member 172. In this configuration, the fit adjustment system optionally may reduce the circumference of the collar 170 by moving the side members 174 such that they the ends are disposed closer to the laryngeal prominence. In one embodiment, the side members 174 and back member 172 contact the neck of the subject when the device is worn, but the front member 173 does not. In another embodiment, the back member 172 is absent such that the collar 170 encircles a majority of the neck with the discontinuous region at the back of the neck.

Figure 35:
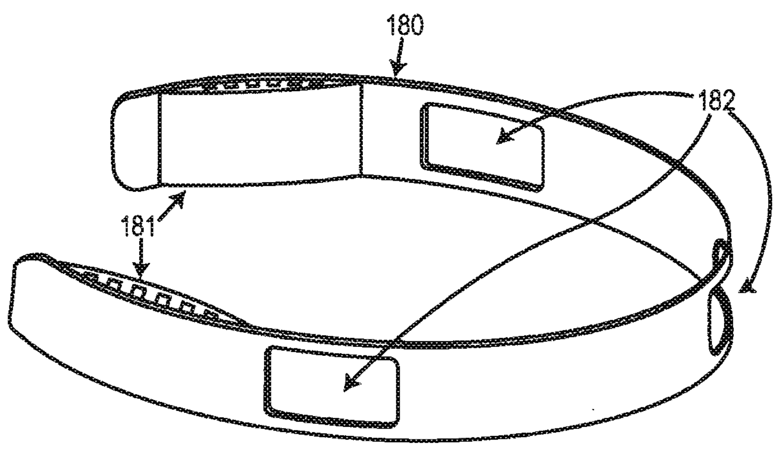
FIG. 35 is an illustration of another embodiment of the collar in which the collar has a plurality of holes adapted to receive fastening straps affixed to a garment (e.g., a shirt or jersey) which are used to secure the collar to the garment.
Figure 36:
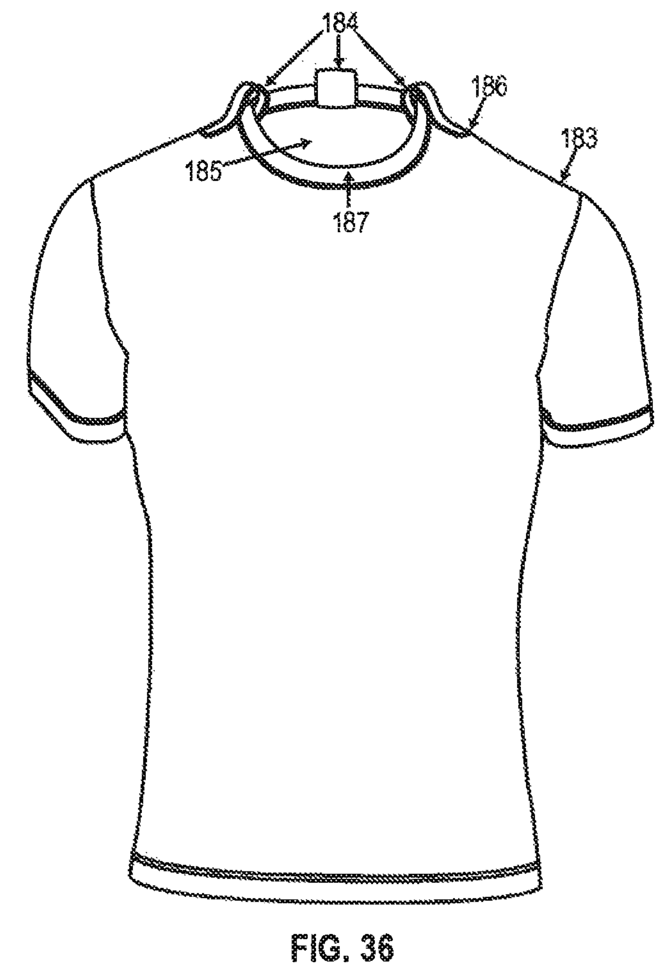
FIG. 36 is an illustration of a shirt having a plurality of straps located about the neck opening, wherein the straps are configured to pass through holes in the collar shown in FIG. 35 for securing the collar to the garment. The ends of the straps may be fastened to the body of the garment.
Figure 37:
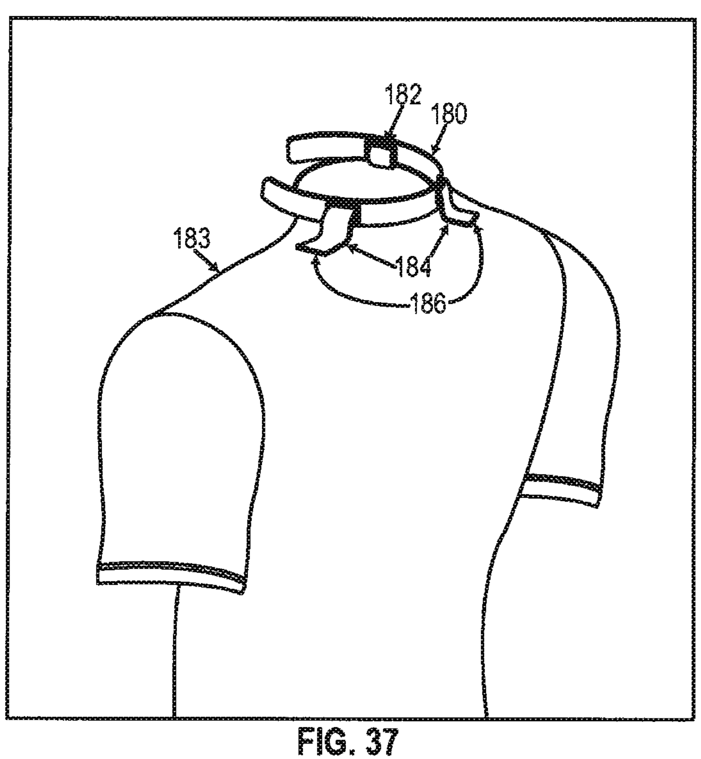
FIG. 37 is an illustration a system in which the collar shown in FIG. 35 is secured to a shirt shown in FIG. 36 and in which the straps are aligned with the holes when the collar is properly positioned about the neck of the subject. The straps on the shirt pass through the holes in the collar and are fastened to the body of the shirt in order to secure the collar to the shirt.

FIGS. 35-37 are illustrations of a garment system of the invention. The system contains at least a garment (e.g., shirt, jersey, jacket, etc.) and a circumferential or semi-circumferential collar constructed in accordance with the principles of the invention. FIG. 35 illustrates a semi-circumferential collar 180, having protuberances shaped as pads 181, adapted for use in the system. The collar 180 has a plurality of holes 182 adapted to receives securing straps affixed to a garment. This collar 180 is shown as having three holes 182, however, any convenient number of holes 182 may be present including, for example, 1, 2, 3, 4, 5, or more holes 182. FIG. 36 illustrates a shirt 183 of the inventive system. The shirt 183 has a plurality of straps 184 affixed about the neck opening 185. The straps 184 are positioned to align with the holes 182 (see, FIG. 35) and adapted to fit conveniently through the holes 182. In one embodiment, the straps 184 and the shirt 185 have fasteners 186 so that the end of the strap 184 may be secured to the body of the shirt 185. Any convenient fasteners 186 may be used including, for example, snaps, adhesives, or a hook-and-pile system (e.g., VELCRO®). Optionally, the shirt comprises a rim 187 around the neck opening 185 such that the rim 187 provides a layer of fabric between the collar 180 and the neck of the subject when the collar 180 is properly positioned on the neck and secured to the shirt 183. FIG. 37 illustrates the assembled system in which the collar 180 is secured to the shirt 183 using the straps 184 which are passed through the holes 182, the loose ends of which are affixed to the body of the shirt 183 using fasteners 186.

Figure 38:
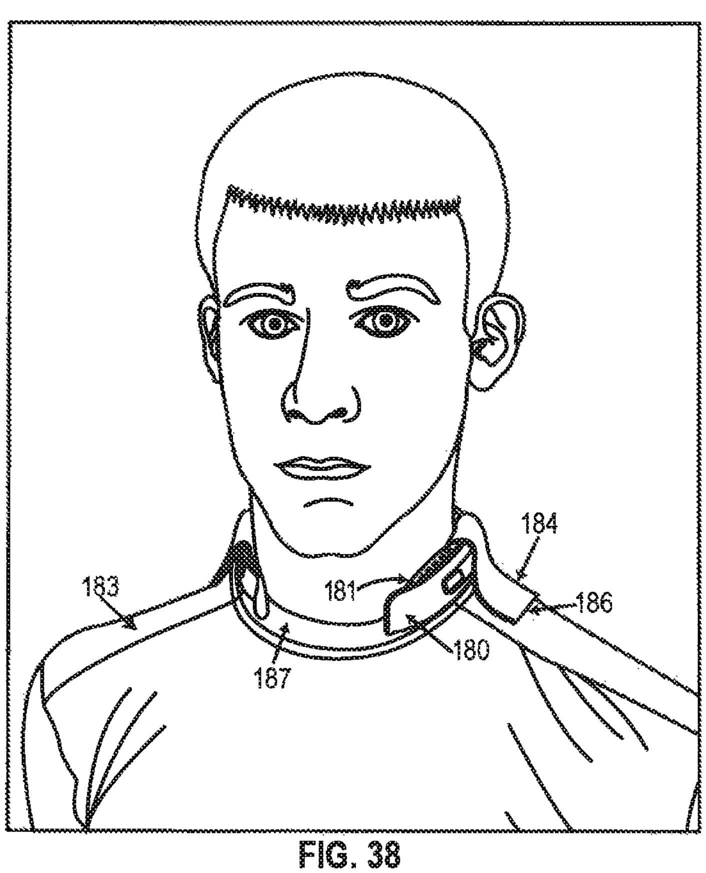
FIG. 38 illustrates another embodiment of the system in which the straps are adapted to pass over the collar and are fastened to the body of the shirt. The collar in this system is illustrated as lacking holes adapted to receive the straps; however, the system may be effected using any suitably designed collar, including a collar containing holes (but in which the holes are not used or are not aligned with the straps when the collar is properly positioned about the neck of the subject).
Figure 31:
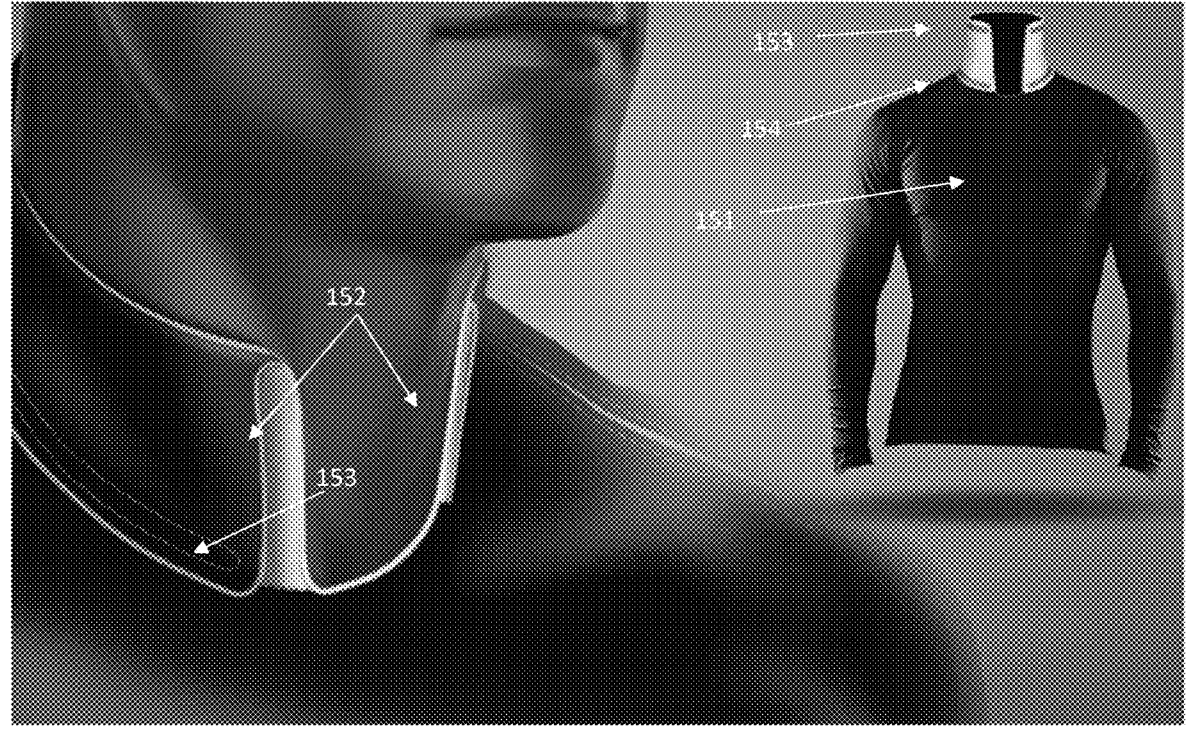
Figure 32:
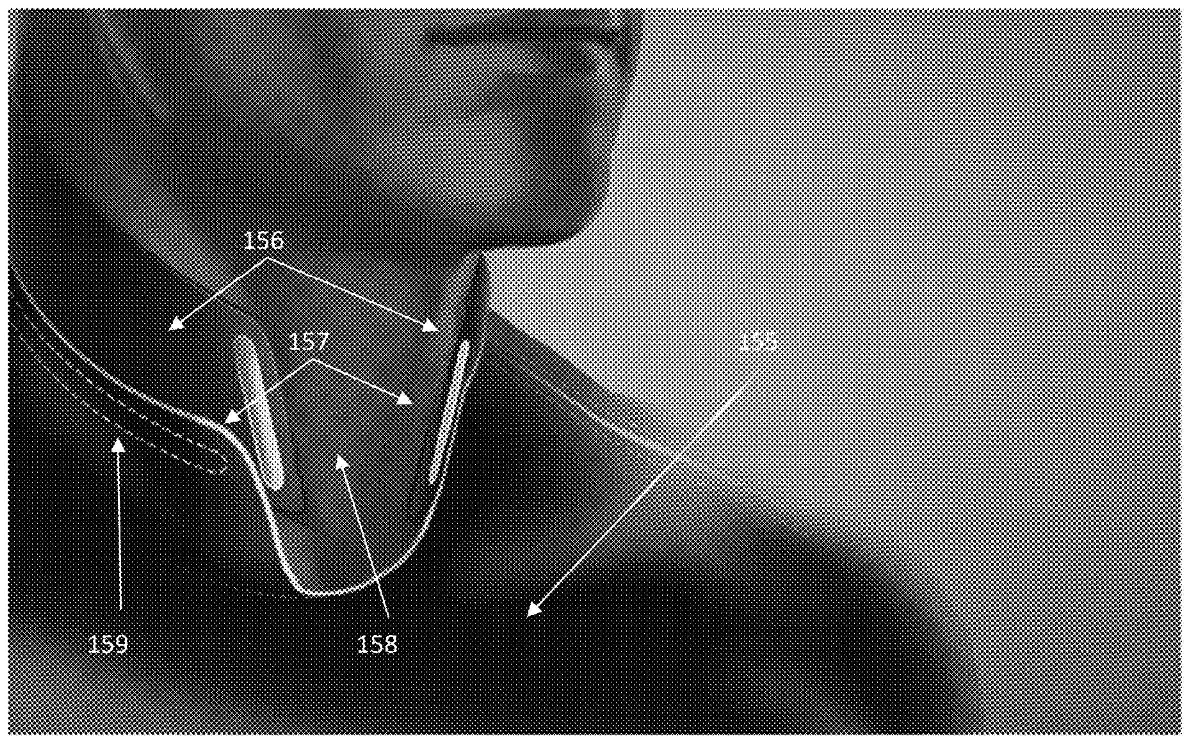
Figure 33:
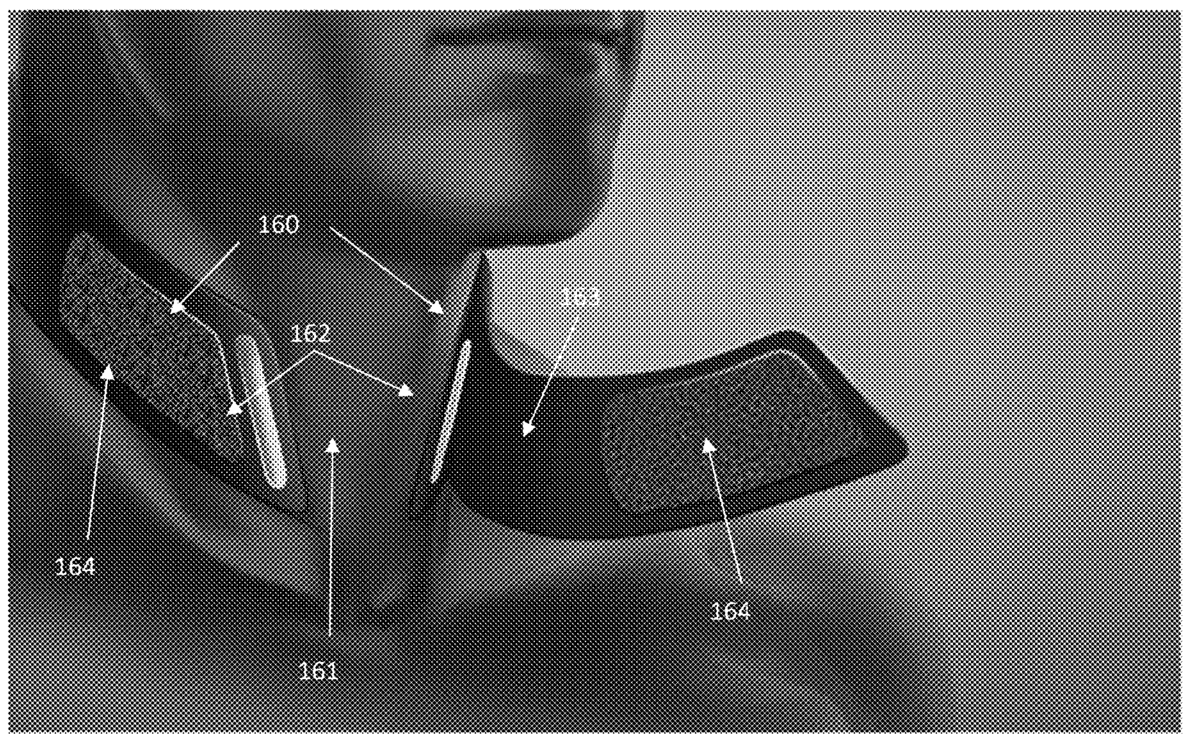

FIG. 38 is an illustration of another garment system of the invention. In this embodiment, the collar 180 optionally may contain or lack holes 182. The collar 180 is secured to the shirt 183 using the straps 184 but the straps 184 do not pass through holes 182. Instead, the straps pass over the top of the collar 180 and the loose ends are fastened to the body of the shirt 183 with fasteners 186.

Example 1

Materials and Methods

Two groups of ten (total of 20) male Sprague-Dawley rats weighing between 350 and 400 grams were used. Animals were housed under 12 hour light/12 hour dark conditions with rat chow and water available ad libitum.

Marmarou Impact Acceleration Injury Model in Rats:

Anesthesia was induced and maintained with isoflurane using a modified medical anesthesia machine. Body temperature was controlled during the approximately 10 min. procedures using a homeothermic heating blanket with rectal probe, and adequate sedation was confirmed by evaluation of response to heel tendon pinch. The animals were shaved and prepared in sterile fashion for surgery, followed by subcutaneous injection of 1% lidocaine local anesthetic into the planned incision site. A 3 cm midline incision in the scalp was made and periosteal membranes separated, exposing bregma and lambda. A metal disk 10 mm in diameter and 3 mm thick was attached to the skull with cyanoacrylate and centered between bregma and lambda.

The animal was placed prone on a foam bed with the metal disk directly under a Plexiglas tube. A 450-g brass weight was dropped a single time through the tube from a height of 2 meters, striking the disk. The animal was then ventilated on 100% oxygen while the skull was inspected, the disk removed, and the incision repaired. When the animal recovered spontaneous respirations, anesthesia was discontinued and the animal was returned to its cage for post-operative observation. Buprenorphine was used for post-operative analgesia.

Example 2

Experimental Protocol

This work involved two groups, each consisting of 10 animals for a total of 20 animals. Two groups were utilized, a control injury group and an experimental injury group. In the experimental injury group the rats were fitted with a 15 mm wide collar, with two compressive beads designed to overlay the IJVs and was tightened sufficiently to provide mild compression of the veins without compromising the airway. The collar was then fixed in circumference with a Velcro fastener. The collar was left in position for three minutes prior to administrating experimental brain injury.

Assessment of Intracranial Reserve Volume Intracranial Pressure (ICP) Measurement:

ICP was measured in five animals using the FOP-MIV pressure sensor (FISO Technologies, Quebec, Canada) as described by Chavko, et al. The head of the rat was shaved and prepped in sterile fashion for surgery. The rat was fixed in a stereotaxic apparatus (model962; Dual Ultra Precise Small Animal Stereotaxic Instrument, Kopf Instruments, Germany) and a 3 cm mid-line incision in the scalp was made. Periosteal membranes were separated, exposing both bregma and lambda. A 2 mm burr hole was drilled 0.9 mm caudal from bregma and 1.5 mm from the midline. The fiber optic probe was then inserted to a depth of 3 mm into the cerebral parenchyma.

Intraocular Pressure (TOP) Measurement:

IOP was measured in all animals using the TonoLab rebound tonometer (Colonial Medical Supply, Franconia, NH) as described in the literature, IOP measurements were taken after induction of anesthesia in all animals and a second time in the experimental group following application of the UV compression device. Following application of the IJV compression device in the experimental injury group, IOP readings were taken every 30 secs while the compression device was in place.

Tissue Preparation and Immunohistochemical Labeling:

At 7 days post-injury all animals (n=20) were anesthetized and immediately perfused transcardially with 200 ml cold 0.9% saline to wash out all blood. This was followed by 4% paraformaldehyde infusion in Millings buffer for 40 mins. The entire brain, brainstem, and rostral spinal cord were removed and immediately placed in 4% paraformaldehyde for 24 hours. Following 24 hours fixation, the brain was blocked by cutting the brainstem above the pons, cutting the cerebellar peduncles, and then making sagittal cuts lateral to the pyramids. The resulting tissue, containing the corticospinal tracts and the mediallenmisci, areas shown previously to yield traumatically injured axons, was then sagitally cut on a vibratome into 50 micron thick sections.

The tissue underwent temperature controlled microwave antigen retrieval using previously described techniques. The tissue was pre-incubated in a solution containing 10% normal serum and 0.2% Triton X in PBS for 40 mins. For amyloid precursor protein (APP) labeling, the tissue was incubated in polyclonal antibody raised in rabbit against beta APP (#51-2700, Zymed, Inc., San Francisco, CA) at a dilution of 1:200 in 1% NGS in PBS overnight. Following incubation in primary antibody, the tissue was washed 3 times in 1% NGS in PBS, then incubated in a secondary anti-rabbit IgG antibody conjugated with Alexa 488 fluorophore (Molecular Probes, Eugene, OR), diluted at 1:200 for two hours. The tissue underwent a final wash in 0.1M phosphate buffer, and then was mounted using an antifade agent and cover-slipped. The slides were sealed with acrylic and stored in the dark in a laboratory refrigerator.

Fluorescent Microscopy and Image Analysis:

The tissue was examined and images acquired using a Olympus AX70 fluorescence microscope system (Olympus; Tokyo, Japan). Ten digital images were obtained from the tissue of each animal and images were then randomized. Individual injured axons were independently counted and data was stored in a spreadsheet (Microsoft Corp., Redmond, WA). Differences between group means were determined using paired t-tests and considered significant if the probability value was less than 0.05.

Stereological Quantification of Axonal Injury:

A stereo logical method was used to determine an unbiased estimate of the number of APP positive axons per cubic mm in the corticospinal tract and medial lemniscus. The optical Fractionator technique utilizing a Stereoinvestigator 9.0 (MBF Bioscience, Inc., Williston, VT) and a Olympus AX70 microscope with 4× and 40× objectives was performed. Sagittal APP stained specimens were examined with low magnification and regions of interest were drawn incorporating the corticospinal tract and medial lemniscus. The software then selected random 50 micron counting frames with depth of 15 microns, and APP positive axons were marked. The volume of the region of interest (ROI) was determined using the Cavalieri method, the volume of the sum of the counting frames was calculated, the sum total of injured axons within the counting frames was calculated, and an estimate of the number of APP positive axons per cubic mm was calculated.

Example 3

Volume Intracranial Pressure (ICP) Measurement

Figure 8:
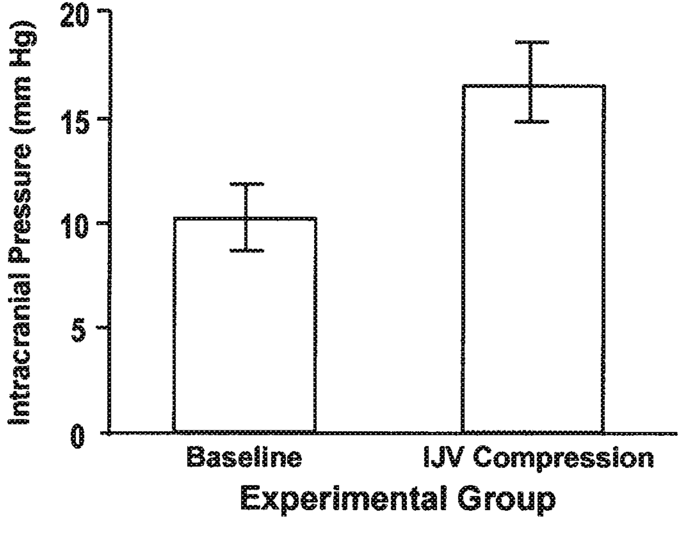
FIG. 8 is a graph illustrating the change in intracranial pressure (ICP) as a consequence of IJV compression, p-value <0.01.
Figure 9:
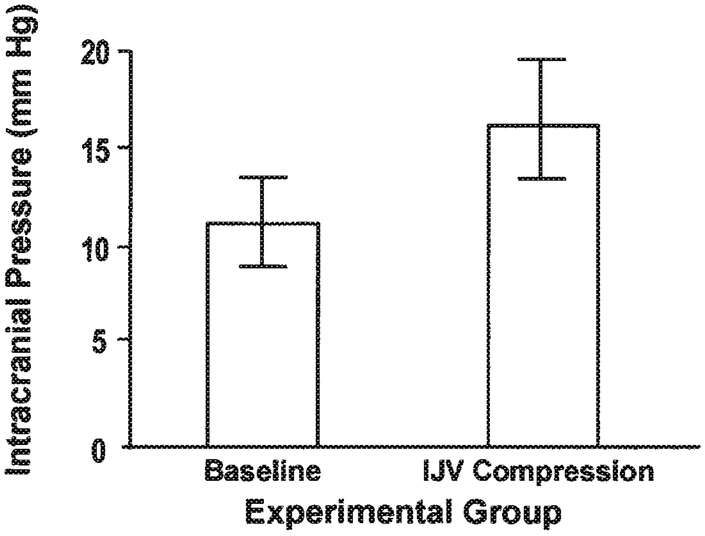
FIG. 9 is a graph illustrating the change in intraocular pressure (TOP) as a consequence of IJV compression, p-value 0.01.

ICP was assessed both prior to and after application of the IJV compression device. The baseline ICP was 10.23±1.68 mm Hg and was increased to 16.63±2.00 mm Hg following IJV compression (FIG. 8: $p<0.01$). Notably, this increase of greater than 30% from baseline occurred within seconds following IJV compression. Intraocular Pressure (TOP) Measurement: IOP measurements were taken both before and after application of the IJV compression device, similar to ICP recordings. The baseline IOP was 11.18±2.27 mm Hg and was elevated to 16.27±3.20 mm Hg following IJV compression (FIG. 9: $p<0.01$).

Figure 10:
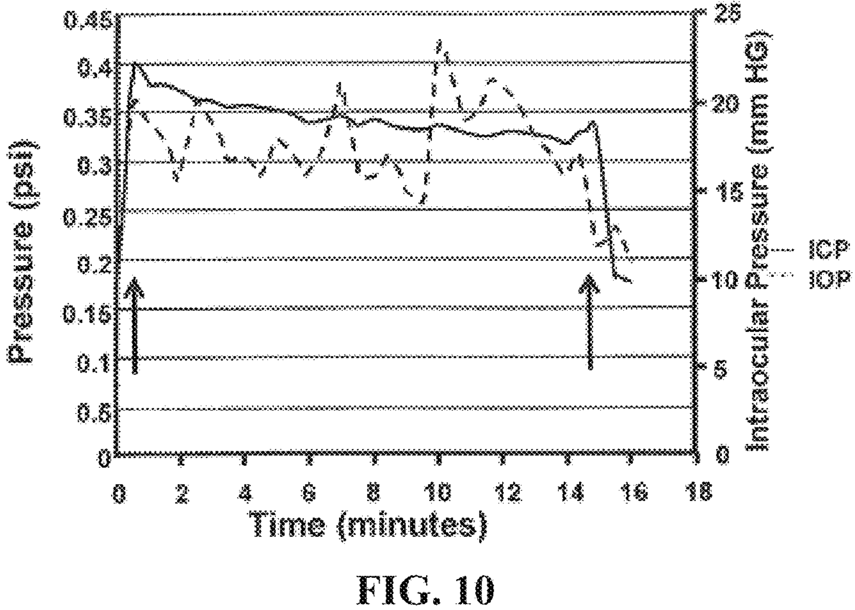
FIG. 10 is a graph showing a representative tracing of physiologic change seen in intracranial pressure (ICP) and intraocular pressure (TOP) over a fifteen minute period caused by the application (arrow on left) and removal of IJV compression (arrow on right). Of note is the rapid response seen in both ICP and IOP and corresponding volumes following IJV compression as well as the duration for which these changes are sustained.

The increase of 31% seen in IOP following IJV compression is strikingly similar to that seen in ICP following IJV compression, both in magnitude and rapidity of response (FIG. 10).

TBI-Impact Acceleration Model:

None of the animals died from the head trauma. Animals tolerated collar application without any observed untoward effects for the duration of the experiment. Specifically, there were no outward or visible signs of discomfort, intolerance, or respiratory difficulty. All recovered without complication and exhibited normal behavioral and feeding habits up until the day of sacrifice. At necropsy, the brains were grossly normal in appearance.

Stereologic Analysis of APP Positive Axons

Figure 11A:
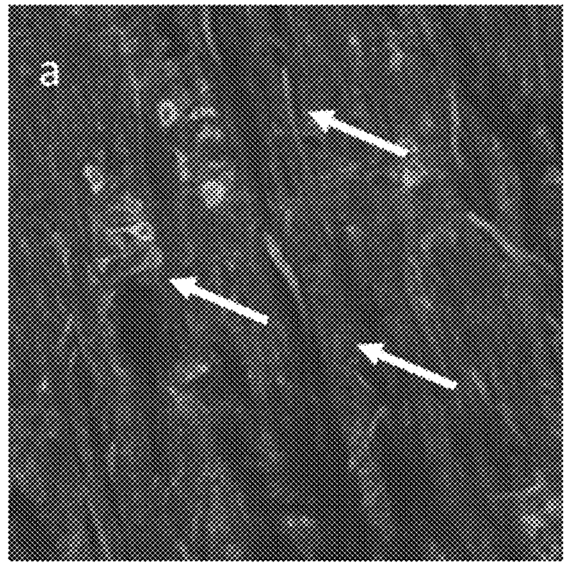
FIG. 11A is a digital image of corticospinal tracts stained for APP post-injury without application of the IJV compression device according to the disclosure.
Figure 11B:
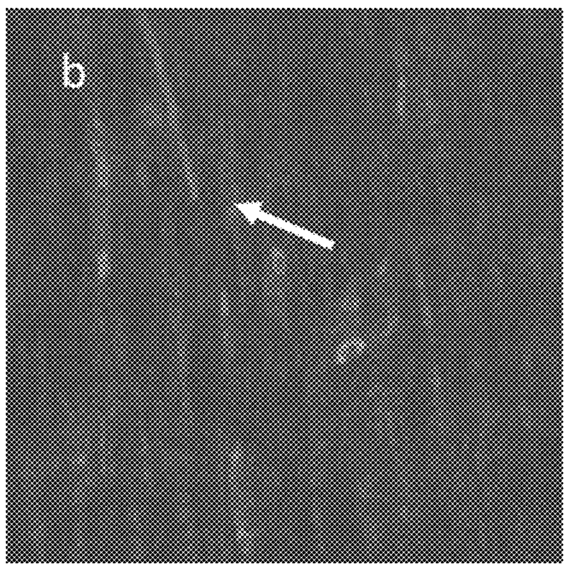
FIG. 11B is a digital image of corticospinal tracts stained for APP post-injury with application of the IJV compression device according to the disclosure.
Figure 12:
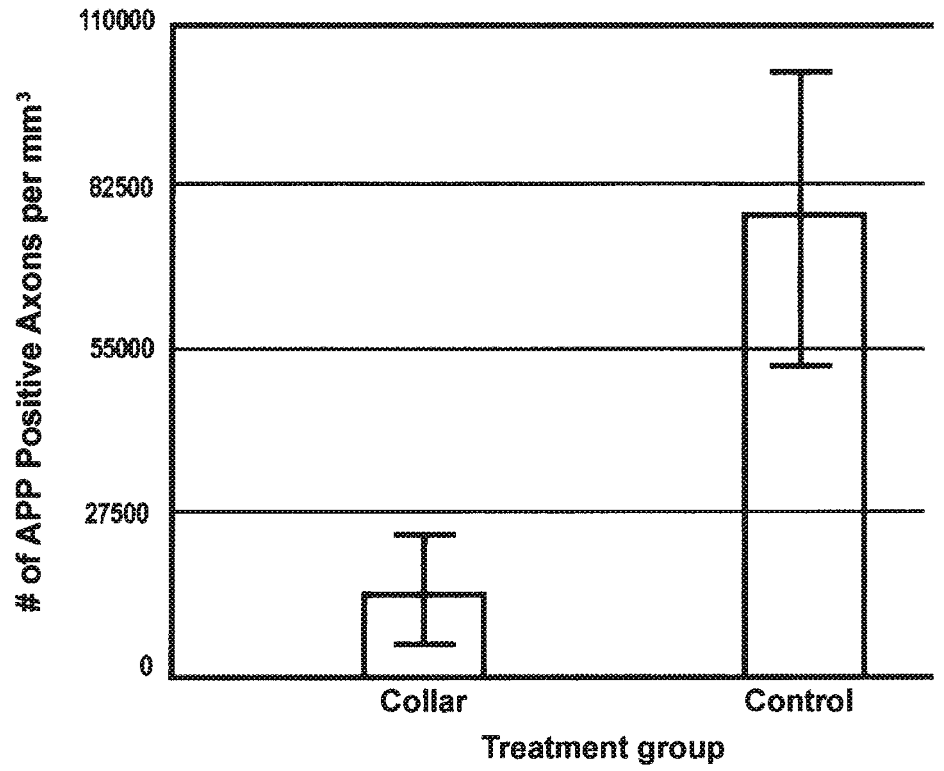
FIG. 12 is a graph illustrating the effect of IJV compression on axonal injury as indicated by APP staining, p-value <001.

To determine the density of injured axons in the corticospinal tracts and medial lenmisci, the stereo logical optical fractionator method was used. Compared to the normal anatomy found in previous experiments with sham animals, control animals without the collar demonstrated focal labeling of APP within many swollen contiguous and terminal axon segments, consistent with impaired axoplasmic transport in traumatic axonal injury. Following microscopic digital image acquisition from multiple areas within the corticospinal tract and medial lenmisci from multiple tissue slices, counting of APP positive axons in animals who received the IJV compression collar demonstrated much fewer APP positive axons, at a frequency much more similar to sham animals, compared to those undergoing injury without UV compression (FIGS. 11A and 11B). These abnormal axons demonstrated typical morphological characteristics of traumatic injury, primarily swelling and disconnection. By qualitative analysis, the experimental group showed (m±sd) 13,540±9808 vs. 77,474±25,325 ($p<0.01$) APP positive axons/$mm^3$ in the control group (FIG. 12).

Example 4

Two groups of 10 adult male Sprague-Dawley rats were subjected to an impact acceleration traumatic brain injury. Prior to the injury, the experimental group had application of a 15 mm wide cervical collar, which had two compressive beads over the internal jugular veins (IJVs). The control group had the experimental injury only. Intracranial pressure (ICP) and intraocular pressure (TOP) were measured before and after IJV compression to assess collar performance. All rats were sacrificed after a 7-day recovery period, and brainstem white matter tracts underwent fluorescent immunohistochemical processing and labeling of beta amyloid precursor protein (APP), a marker of axonal injury. Digital imaging and statistical analyses were used to determine if IN compression resulted in a diminished number of injured axons.

Example 5

All animals survived the experimental paradigm and there were no adverse reactions noted following application of the collar. In the experimental group, IJV compression resulted in an immediate and reversible elevation of ICP and IOP, by approximately 30%, demonstrating physiologic changes secondary to collar application. Most notably, quantitative analysis showed 13,540 APP positive axons in the experimental group versus 77,474 in the control group ($p<0.0$), a marked reduction of greater than 80%.

Using a standard acceleration-deceleration impact laboratory model of mild TBI, a reduction of axonal injury following IJV compression as indicated by immunohistochemical staining of APP was shown. IJV compression reduces SLOSH-mediated brain injury by increasing intracranial blood volume and reducing the compliance and potential for brain movement within the confines of the skull.

Example 6

Internal Versus External Brain Protection

Compression of the IJV for 3 min prior to head trauma led to physiological alterations in intracranial compliance, as evidenced by modest increases in ICP and IOP, while simultaneously and markedly reducing the pathologic index of primary neuronal injury in the standardized rat model of TBI. Reduction in brain volume compliance could prevent the differential motions between the cranium and the brain that lead to energy absorption and neuronal primary and secondary injuries. These pathological changes include axonal tearing that disrupt axoplasmic transport resulting in axonal swelling and activation of the apoptotic cascades, as evidenced in this model by a statistically significant reduction in APP counts of injured axons.

In the animal model of the present disclosure, applying the collar increased ICP and IOP by 30% and 31%, respectively. The effect of compression of jugular veins on ICP is clinically well known. The Queckenstadt test is used to indicate the continuity of CSF between the skull and spinal cord. In this test, ICP is increased by compression of the IJVs while the CSF pressure is measured in the spine through a lumbar puncture. Increases in ICP have also been shown to occur with placement of tight fitting neck stabilization collars that likely compress the IJVs. Compression of the IJVs, which can occur when wearing shirts with tight collars or neckties, has also been shown to increase IOP. Notably, only mild compressive pressure is required to partially occlude the IJVs as they are a low pressure system. As the inflow of cerebral arterial blood continues after partial cerebral venous outlet obstruction, the intracerebral and venous pressure increases until the jugular venous resistance is overcome or the blood drainage is redirected to other venous channels. In either case there is a reduction in intracranial compliance and a modest increase in ICP.

The immunohistochemical assay used in the studies of the present disclosure is specific for axonal damage and results in a reliable range of measured damaged neurons. In addition, the Marmarou model of acceleration-deceleration injury is an accepted and well-studied methodology by which to quantify the extent of TBI. The reduction in damaged axons, as evidenced by a marked reduction in APP counts, in the experimental group with the IJV compression device is highly statistically significant ($p<0.01$). Additionally, the change in ICP was measured after applying the collar in five rats. The results show that every study rat had a reduction in axonal injury greater than the 95% confidence interval of the control group.

In a further aspect of the present invention it has been found that applying compression to the internal jugular vein not only reduces the risk of TBI, but also the risk of damage to the inner ear (specifically Noise Induced Hearing Loss or Blast Induced Hearing Loss), spinal cord and structures of the eye. With respect to the ear, reducing IJV outflow will congest the cochlear vein and thereby take up the compliance of the inner ear or more particularly the fluid within the inner ear. Since the auditory hair cells react directly to the vibrations in the cochlear fluid they are particularly susceptible to SLOSH energy absorption. Increasing the pressure of the fluid within the inner ear reduces the compressibility of the fluid within the inner ear structure so that blast energy is transmitted mechanically through the inner ear rather than absorbed by it in the form of vibration of the fluid. It is noted that increase the fluid pressure does not generally reduce transverse vibrations of the cochlear duct so the transmission of blast energy through the inner ear may still lead to perforation of the eardrum. But in many cases ruptured ear drums will heal or can be repaired. On the other hand, SLOSH-related damage to the fine auditory hair cells does not heal and cannot be repaired.

With respect to the spinal cord, it has been found that applying the IJV pressure techniques described herein reduces the compliance of fluid along the spinal axis and thus reduces the risk of blast-related spinal injury. The spinal injury mode is similar to the inner ear damage mode in that the spinal cord tracts may be regarded as the sensitive filaments in a fluid environment. Fluid vibration due to SLOSH can damage and may even sever spinal cord tissue. Increasing the CSF pressure by compression of the IJV according to the procedure disclosed herein will significantly reduce the CSF vibration due to blast energy. Moreover, increasing the CSF pressure increase the axial load-bearing capacity of the spinal column which can reduce the likelihood of collapse of the spinal column due to blast energy.

With respect to the structure of the eye, the injury mode is similar to that of the inner ear and spine in that vibrations (inelastic collisions) of the vitreous humor can lead to permanent damage to the internal structure of the eye. As demonstrated by a woodpecker's pectin apparatus's increasing intraocular volume and pressure which protects the internal structure of the eye; using the compression band to apply pressure to the IJV as disclosed herein the intra-ocular pressure can be increased 36-60%. Safely and reversibly increasing CSF and thereby intra-ocular pressure using the compression band disclosed herein can prevent or at a minimum significantly reduce the vibration and energy absorption of the vitreous humor within the eye, thereby reducing the risk of blast-related damage.

Finally, as discussed above, the concussive events leading to TBI, has also been found to be a leading cause of anosmia (loss or impairment of olfactory function, i.e., sense of smell). Increasing intracranial pressure as described above can reduce the risk of TBI and the associated impairment of olfactory function. In the case of Breecher or bomb-sniffing dogs the collar may be sized to fit the neck of the animal and the pressure adjusted to account for the greater thickness of the neck at the IJV over that of a human subject.

The foregoing description addresses blast-related traumatic injuries to the intracranial cavity, such as TBI, and injuries to the inner ear, spinal cord and ocular structure. The compression devices disclosed herein may thus be worn by military personnel during battle and removed when not in combat. Although certainly less dramatic, certain sports can expose the intracranial cavity to concussive forces that create the risk of these same traumatic injuries, most notably football. The compression collar disclosed herein would be worn by the sports participant in the field of play as well as a multitude of industrial or other potential TBI risky avocations or professions. The embodiments of the collar disclosed herein are relatively non-intrusive and the "break away" feature described above eliminates the risk of the collar being inadvertently pulled.

What is claimed is:

1. A system comprising:

a semi-circumferential collar adapted to be worn on a neck of a human subject, wherein the semi-circumferential collar comprises a resilient arcuate band having a general C, V, or U-shape and sized to encircle a majority of the neck of the subject and a pair of rigid or semi-rigid side members integral to the resilient arcuate band and having two or more inwardly-directed protuberances that are integral to the semi-circumferential collar; and a garment with a semi-circumferential flap around a neck opening, wherein the semi-circumferential flap is adapted to fold over the semi-circumferential collar to conceal the semi-circumferential collar with the inwardly-directed protuberances positioned to apply pressure to one or more neck veins of the subject, wherein the semi-circumferential flap and the semi-circumferential collar are both adapted to be open at the laryngeal prominence when the garment and collar are worn by the subject and the semi-circumferential flap is folded over the collar, and wherein the resilient arcuate band is configured so that when the collar is applied to the neck, the resilient arcuate band is expanded and spring tension from the expanded resilient arcuate band causes a compressive force that maintains the collar in place on the neck and applies sufficient pressure via the inwardly-directed protuberances to the one or more neck veins of the subject to restrict blood flow egressing from the head of the subject through the one or more neck veins.

2. The system of claim 1, wherein the semi-circumferential flap has an upper attachment device and lower attachment device, wherein the semi-circumferential flap forms a sleeve enclosing the collar when the upper attachment device and the lower attachment device are engaged with each other.

3. The system of claim 2, wherein the upper attachment device and the lower attachment device comprise a hook-and-pile system.

4. The system of claim 1, wherein the one or more neck veins comprises an internal jugular vein.

5. The system of claim 1, wherein the one or more neck veins comprise an external jugular vein.

6. The system of claim 1, wherein the collar is adapted to exert a pressure on the one or more neck veins equivalent to a fluid pressure within the range of 10 mm Hg to 80 mm Hg.

7. A system comprising:

a semi-circumferential collar adapted to be worn on the neck of a human subject, wherein the semi-circumferential collar comprises a resilient arcuate band having a general C, V, or U-shape and sized to encircle a majority of the neck of the subject and a pair of rigid or semi-rigid side members integral to the resilient arcuate band and having two or more inwardly-directed protuberances that are integral to the semi-circumferential collar; and a garment with a semi-circumferential sleeve around a neck opening of the garment, wherein the semi-circumferential sleeve is adapted to removably receive the semi-circumferential collar to conceal the semi-circumferential collar in the semi-circumferential sleeve with the inwardly-directed protuberances positioned to apply pressure to one or more neck veins of the subject, wherein the semi-circumferential sleeve and the semi-circumferential collar are both open at the laryngeal prominence when worn by the subject and when the semi-circumferential sleeve removably receives the semi-circumferential collar, and wherein the resilient arcuate band is configured so that when the semi- circumferential collar is applied to the neck, the resilient arcuate band is expanded and spring tension from the expanded resilient arcuate band causes a compressive force that maintains the semi-circumferential collar in place on the neck and applies sufficient pressure via the inwardly-directed protuberances to the one or more neck veins of the subject to restrict blood flow egressing from the head of the subject through the one or more neck veins.

8. The system of claim 7, wherein the one or more neck veins comprises an internal jugular vein.

9. The system of claim 7, wherein the one or more neck veins comprise an external jugular vein.

10. The system of claim 7, wherein the semi-circumferential collar is adapted to exert a pressure on the one or more neck veins equivalent to a fluid pressure within the range of 10 mm Hg to 480 mm Hg.

11. A system comprising:

a garment having a neck opening and a flap around the neck opening, the garment being configured to be worn by a user so that a neck of a user passes through the neck opening; and a semi-circumferential collar adapted to be worn on the neck over a layer of fabric of the flap with a remaining portion of the flap being adapted to fold over the semi-circumferential collar to conceal the semi-circumferential collar, wherein the semi-circumferential collar comprises a resilient arcuate band having a general C, V, or U-shape and sized to encircle a majority of the neck of the subject and a pair of rigid or semi-rigid side members integral to the resilient arcuate band and having two or more inwardly-directed protuberances that are integral to the semi-circumferential collar, wherein the flap and the semi-circumferential collar are both open at a laryngeal prominence of the user when worn by the subject and when the flap is folded over the semi-circumferential collar, and wherein the resilient arcuate band is configured so that when the semi-circumferential collar is applied to the resilient arcuate band is expanded and spring tension from the expanded resilient arcuate band causes a compressive force that maintains the semi-circumferential collar in place on the neck and applies sufficient pressure via the inwardly-directed protuberances to the one or more neck veins of the subject to restrict blood flow egressing from the head of the subject through the one or more neck veins.

12. The system of claim 11, further comprising an attachment device that secures the flap in position folded over the semi-circumferential collar.

13. The system of claim 11, wherein the flap forms a sleeve enclosing the semi-circumferential collar.

* * * * *